United States Patent
Brennan et al.

(10) Patent No.: US 7,655,622 B2
(45) Date of Patent: *__Feb. 2, 2010__

(54) COMPOSITION AND METHOD FOR REGULATION OF BODY WEIGHT AND ASSOCIATED CONDITIONS

(75) Inventors: Miles B. Brennan, Denver, CO (US); Ute Hochgeschwender, Oklahoma City, OK (US)

(73) Assignees: Eleanor Roosevelt Institute, Denver, CO (US); Oklahoma Medical Research Foundation, Oklahoma, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/752,960

(22) Filed: Jan. 6, 2004

(65) Prior Publication Data

US 2005/0032678 A1    Feb. 10, 2005

Related U.S. Application Data

(63) Continuation of application No. 09/458,580, filed on Dec. 9, 1999, now Pat. No. 6,716,810.

(60) Provisional application No. 60/111,581, filed on Dec. 9, 1998, provisional application No. 60/146,306, filed on Jul. 29, 1999, provisional application No. 60/146,305, filed on Jul. 29, 1999, provisional application No. 60/146,304, filed on Jul. 29, 1999, provisional application No. 60/146,303, filed on Jul. 29, 1999, provisional application No. 60/146,302, filed on Jul. 29, 1999, provisional application No. 60/146,301, filed on Jul. 29, 1999, provisional application No. 60/146,300, filed on Jul. 29, 1999, provisional application No. 60/146,299, filed on Jul. 29, 1999.

(51) Int. Cl.
*A61K 38/00* (2006.01)

(52) U.S. Cl. ............................................. 514/9; 514/15

(58) Field of Classification Search ........................ None
See application file for complete search history.

(56) References Cited

U.S. PATENT DOCUMENTS

| | | | |
|---|---|---|---|
| 4,485,039 A | 11/1984 | Hruby et al. |
| 4,649,191 A | 3/1987 | Hruby |
| 4,874,744 A | 10/1989 | Norlund et al. |
| 4,918,055 A | 4/1990 | Hruby et al. |
| 5,420,109 A | 5/1995 | Suto et al. |
| 5,532,347 A | 7/1996 | Cone et al. |
| 5,580,859 A | 12/1996 | Felgner et al. |
| 5,589,466 A | 12/1996 | Felgner et al. |
| 5,593,972 A | 1/1997 | Weiner et al. |
| 5,641,662 A | 6/1997 | Debs et al. |
| 5,674,839 A | 10/1997 | Hruby et al. |
| 5,676,954 A | 10/1997 | Brigham |
| 5,683,981 A | 11/1997 | Hadley et al. |
| 5,691,309 A | 11/1997 | Basinski et al. |
| 5,703,220 A | 12/1997 | Yamada et al. |
| 5,710,265 A | 1/1998 | Yamada et al. |
| 5,714,576 A | 2/1998 | Hruby et al. |
| 5,726,156 A | 3/1998 | Girten et al. |
| 5,731,408 A | 3/1998 | Hadley et al. |
| 5,756,461 A | 5/1998 | Stephens |
| 5,760,001 A | 6/1998 | Girten et al. |
| 5,766,877 A | 6/1998 | Stark et al. |
| 5,773,416 A | 6/1998 | Chehab |
| 5,780,258 A | 7/1998 | de la Brousse et al. |
| 5,786,332 A | 7/1998 | Girten et al. |
| 5,830,450 A | 11/1998 | Lallone |
| 5,830,994 A | 11/1998 | D'Hinterland et al. |
| 5,831,017 A | 11/1998 | Hoffmann |
| 5,843,652 A | 12/1998 | Woychik |
| 5,846,734 A | 12/1998 | Serrero |
| 5,849,708 A | 12/1998 | Maratos-Flier |
| 5,851,995 A | 12/1998 | Basinski et al. |
| 5,866,547 A | 2/1999 | Flier et al. |
| 5,869,452 A | 2/1999 | Ng et al. |
| 5,908,609 A | 6/1999 | Lee et al. |
| 5,932,779 A | 8/1999 | Lee et al. |
| 6,127,381 A | 10/2000 | Basu et al. |
| 6,245,738 B1 | 6/2001 | Suto et al. |

(Continued)

FOREIGN PATENT DOCUMENTS

| EP | 0 292 291 | * | 5/1988 |
|---|---|---|---|
| WO | WO95/13086 | | 5/1995 |
| WO | WO96/27386 | | 9/1996 |
| WO | WO 97/47316 | | 12/1997 |
| WO | WO 98/10068 | | 3/1998 |
| WO | WO 99/21571 A1 | | 5/1999 |
| WO | WO 99/55679 A1 | | 11/1999 |
| WO | WO 00/35952 | | 6/2000 |

OTHER PUBLICATIONS

Sawyer et al. [half-Cys4,half-Cys10]-a-Melanocyte-stimulating hormone: A cyclic a-melanotropin exhibiting superagonist biological activity. Proc Natl Acad Sci USA 1982, vol. 79, pp. 1751-1755.*

(Continued)

*Primary Examiner*—Cecilia Tsang
*Assistant Examiner*—Marcela M Cordero Garcia
(74) *Attorney, Agent, or Firm*—Brinks Hofer Gilson & Lione

(57) ABSTRACT

Methods for regulating body weight and/or regulating weight gain are provided herein. The methods are useful, for instance, for treating or preventing obesity. Specifically, methods of administering varying levels of various alpha melanocyte stimulating hormone (α-MSH) analog compounds to an animal are provided for reducing body weight and/or reducing the rate of body weight gain.

19 Claims, 14 Drawing Sheets

U.S. PATENT DOCUMENTS

| | | | |
|---|---|---|---|
| 6,278,038 | B1 | 8/2001 | Cone et al. |
| 6,344,481 | B1 * | 2/2002 | Cornelius et al. ............ 514/539 |
| 6,350,430 | B1 | 2/2002 | Dooley et al. |
| 6,376,509 | B1 | 4/2002 | Bakshi et al. |
| 6,603,058 | B1 * | 8/2003 | Brennan et al. ............... 800/18 |
| 6,608,082 | B1 | 8/2003 | Basu et al. |
| 6,689,938 | B2 | 2/2004 | Brennan et al. |
| 6,716,810 | B1 * | 4/2004 | Brennan et al. ................ 514/2 |
| 2006/0063708 | A1 * | 3/2006 | Brennan et al. ................ 514/9 |

OTHER PUBLICATIONS

Considine et al. Serum Immunoreactive-Leptin Concentrations in Normal-Weight and Obese Humans. The New England Journal of Medicine. Feb. 1, 1996. pp. 292-295.*

Fisher et al. Melanocortin-4 receptor: A novel signalling pathway involved in body weight regulation. International Journal of Obesity. 1999. Vo.. 23, Suppl 1, pp. 54-58.*

California Peptide Research, MW of Alpha MSH Ac-Nle4 c[Asp5-DPhe7 Lys10] 4-10 amide. Accessed online on Jun. 23, 2007 at http://www.californiapeptide.com/catalog.php?page=2&f=&search=&srchfld=&PHPSESSID=191fcdd62dc39e55a377b9906b4c79ae. 3$^{rd}$ compound in p. 1 (1 page).*

Blüher, et al.; "Responsiveness to Peripherally Administered Melanocortins in Lean and Obese Mice;" Diabetes, vol. 53, Jan. 2004, pp. 82-90.

Fan, Wei et al.; Role of melanocortinergic neurons in feeding and the *agouti* obesity syndrome; Nature; vol. 385; pp. 165-168; Jan. 9, 1997.

Friedman, Jeffery M.; The alphabet of weight control; Nature; vol. 385; pp. 119-120; Jan. 9, 1997.

Huszar, Dennis et al.; Targeted Disruption of the Melanocortin-4 Receptor Results in Obesity in Mice; Cell; vol. 88; pp. 131-141; Jan. 10, 1997.

Poggioli, R. et al.; "ACTH- (1-24) and alpha-MSH antagonize feeding behavior stimulated by kappa opiate antagonists;" Peptides, Elsevier, Amsterdam, US, vol. 7, No. 5; 1986; pp. 843-848; XP009018115.

Fan, W. et al.; "Role of Melanocortinergic Neurons in Feeding and the Agouti Obesity Syndrome;" Nature, Macmillan Journals Ltd., London, GB; vol. 385; Jan. 9, 1997; pp. 165-168; XP002072475.

Huszar, D. et al.; "Targeted Disruption of the Melanocortin-4 Receptor Results in Obesity in Mice;" Cell, Cell Press, Cambridge,, NA, US; vol. 88, No. 1; Jan. 10, 1997; pp. 131-141; XP000877328.

"A Frameshift Mutation in Human MC4R is Associated with a Dominant Form of Obesity;" Nature Genetics, New York, NY, US; vol. 20, No. 2; Oct. 1998; pp. 113-114; XP000866527.

"A Frameshift Mutation in MC4R Associated with Dominantly Inherited Human Obesity;" Nature Genetics, New York, NY, US; vol. 20, No. 2; Oct. 1998; pp. 111-112; XP000866528.

Chagnon, Yvon C. et al.; "Linkage and association studies between the melanocortin receptors 4 and 5 genes and obesity-related phenotypes in the Quebec Family Study;" Molecular Medicine, New York; vol. 3, No. 10; Oct. 1997; pp. 663-673; XP009046979.

Jackson, R.S. et al.; "Proopiomelanocortin products and human early-onset obesity;" The Journal of Clinical Endocrinology and Metabolism; Feb. 1999; pp. 819-820; XP002326389.

Mizuno, T.M. et al.; "Hypothalamic Pro-Opiomelanocortin MRNA is Reduced by Fasting in OB/OB and DB/DB Mice, but is Stimulated by Leptin;" Diabetes, New York, NY, US; vol. 47., No. 2; Feb. 1998; pp. 294-297; XP001063909.

Cheung, C.C. et al.; "Proopiomelanocortin Neurons are Direct Targets for Leptin in the Hypothalamus;" Endocrinology; Baltimore, MD, US; vol. 138, No. 10; 1997; pp. 4489-4492; XP009027762.

Boston, Bruce A. et al.; "Characterization of melanocortin receptor subtype expression in murine adipose tissues and in the 3T3-L1 cell line;" Endocrinology; vol. 137, No. 5; 1996; pp. 2043-2050; XP002326390.

Bertagna, Xavier; "Proopiomelanocortin-derived peptides;" Endocrinology and Metabolism Clinics of North America; vol. 23, No. 3; 1994; pp. 467-485; XP009046900.

Abou-Mohamed, G.; Papapetropoulos, A.; Ulrich, D.; Catravas, J.D.; Tuttle, R.R.; and Caldwell, R.W., "HP-228, A Novel Synthetic Peptide, Inhibits the Induction of Nitric Oxide Synthase In Vivo But Not In Vitro," *The Journal of Pharmacology and Experimental Therapeutics*, vol. 275, No. 2, 584-591 (1995).

Corcos, I; Thompson, E.E.; Omholt, P. MD; McPherson, Lee S.; McDowell, R.; Houghten, R.; and Girten, B., "HP 228 is a potential agonist of melanocortin receptor 4, and significantly attenuates obesity and diabetes in Zucker fatty rats," *Society for Neuroscience,* vol. 23, Abstract 267.9 (1997).

Compound May Utilize Newly Discovered Signaling Pathway URL: http://www.pslgroup.com/dg/124DA.htm; Doctor''s Guide; Jan. 17, 1997.

Trega Biosciences Inc; Form: 10-K405 Filing; Mar. 31, 1999.

Rubinstein et al.; *Nucleic Acids Research*; 21(11):2613-2617; 1993.

Mullins et al.; "Perspective Series: Molecular Medicine in Genetically Engineered Animals—Transgenesis in the Rat and Larger Mammals;" Transgenesis in Nonmarine Species; J. Clin. Invest., vol. 97, No. 7, pp. 1557-1560; Apr. 1996.

Moreadith et al.; "Gene Targeting in Embryonic Stem Cells: The New Physiology and Metabolism;" J. Mol. Med.; 75:[pp. 208-216]; 1997.

Krude et al.; Nature Genetics; 19:155-157; 1998.

Yaswen et al.; "Obesity in the Mouse Model of Pro-Opiomelanocortin Deficiency Responds to Peripheral Melanocortin;" Nature Medicine; vol. 5, No. 9, pp. 1066-1070; Sep. 1999.

Pera et al.; "Human Embryonic Stem Cells;" J. Cell Science 113; pp. 5-10; 2000.

* cited by examiner

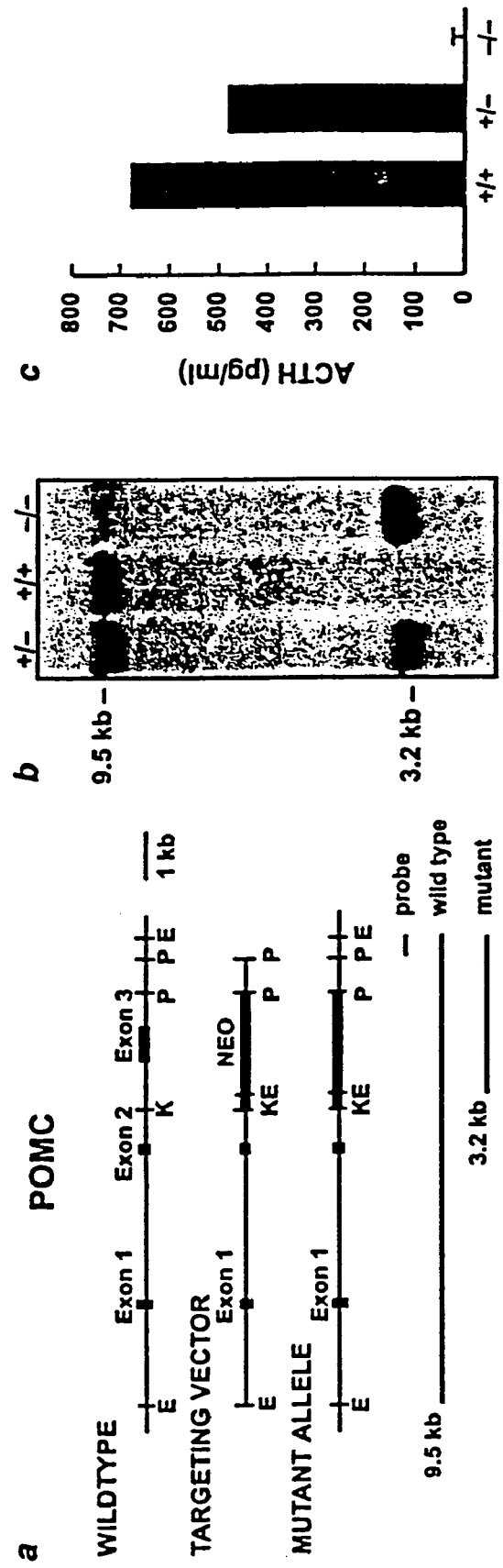

FIG. 3A
FIG. 3B
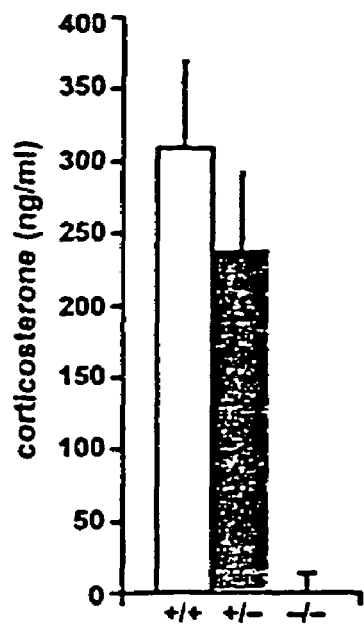
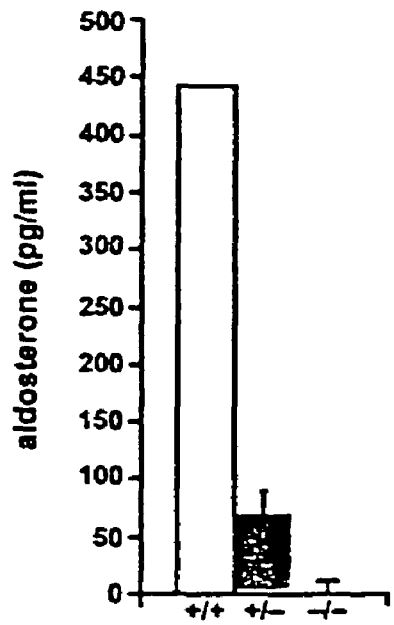
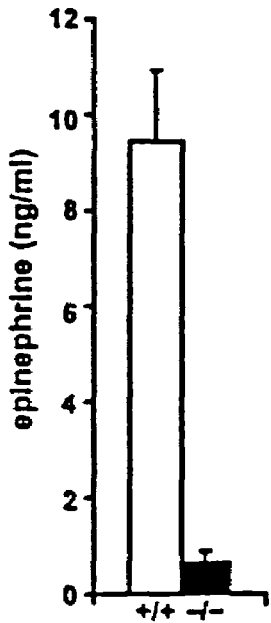
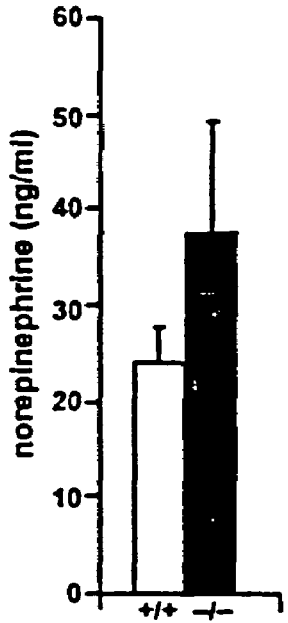
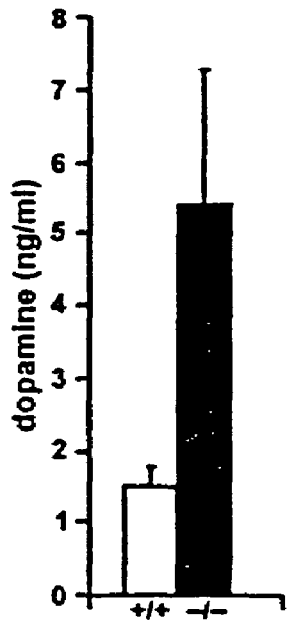
FIG. 3C   FIG. 3D   FIG. 3E

SEQUENCE LISTING

```
<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(5)
<223> OTHER INFORMATION: conserved region, synthetic

<400> SEQUENCE: 1

Glu His Phe Arg Trp
1               5
```

```
<210> SEQ ID NO 2
<211> LENGTH: 13
<212> TYPE: PRT
<213> ORGANISM: Homo sapiens

<400> SEQUENCE: 2

Ser Tyr Ser Met Glu His Phe Arg Trp Gly Lys Pro Val
1               5                   10

<210> SEQ ID NO 3
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: Xaa = Nle
<220> FEATURE:
<221> NAME/KEY: PEPTIDE
<222> LOCATION: (1)..(7)
<223> OTHER INFORMATION: analog
<220> FEATURE:
<221> NAME/KEY: VARIANT
<222> LOCATION: (2)..(2)
<223> OTHER INFORMATION: Xaa = Glu or Asp
<220> FEATURE:
<221> NAME/KEY: VARIANT
<222> LOCATION: (4)..(4)
<223> OTHER INFORMATION: Xaa = Phe or D-Phe
<220> FEATURE:
<221> NAME/KEY: VARIANT
<222> LOCATION: (7)..(7)
<223> OTHER INFORMATION: Xaa = dibasic amino acid; Lys; Orn; Dbu; or Dpr

<400> SEQUENCE: 3

Xaa Xaa His Xaa Arg Trp Xaa
1               5

<210> SEQ ID NO 4
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: PEPTIDE
<222> LOCATION: (1)..(13)
<223> OTHER INFORMATION: analog
<220> FEATURE:
<221> NAME/KEY: VARIANT
<222> LOCATION: (4)..(4)
<223> OTHER INFORMATION: Xaa = Met, Nle, or Cys
<220> FEATURE:
<221> NAME/KEY: MOD_RES
<222> LOCATION: (7)..(7)
<223> OTHER INFORMATION: Phe = D-Phe

<400> SEQUENCE: 4

Ser Tyr Ser Xaa Glu His Phe Arg Trp Gly Lys Pro Val
1               5                   10

<210> SEQ ID NO 5
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: MOD_RES
```

```
<222> LOCATION: (1)..(1)
<223> OTHER INFORMATION: Nle
<220> FEATURE:
<221> NAME/KEY: PEPTIDE
<222> LOCATION: (1)..(7)
<223> OTHER INFORMATION: analog
<220> FEATURE:
<221> NAME/KEY: MOD_RES
<222> LOCATION: (4)..(4)
<223> OTHER INFORMATION: Xaa = D-naphthylalanine

<400> SEQUENCE: 5

Xaa Asp His Xaa Arg Trp Lys
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: Xaa = Nle
<220> FEATURE:
<221> NAME/KEY: PEPTIDE
<222> LOCATION: (1)..(7)
<223> OTHER INFORMATION: analog
<220> FEATURE:
<221> NAME/KEY: MOD_RES
<222> LOCATION: (4)..(4)
<223> OTHER INFORMATION: Phe = D-para-iodo-phenylalanine

<400> SEQUENCE: 6

Xaa Asp His Phe Arg Trp Lys
1               5
```

COMPOSITION AND METHOD FOR REGULATION OF BODY WEIGHT AND ASSOCIATED CONDITIONS

CROSS-REFERENCE TO RELATED APPLICATIONS

This application is a continuation of application Ser. No. 09/458,580, filed Dec. 9, 1999, now U.S. Pat. No. 6,716,810, which is hereby incorporated by reference herein and which claims priority under U.S.C. §119(e) from: U.S. Provisional Application Ser. Nos. 60/111,581, filed Dec. 9, 1998; 60/146, 306, filed Jul. 29, 1999; 60/146,305, filed Jul. 29, 1999; 60/146,304, filed Jul. 29, 1999; 60/146,303, filed Jul. 29, 1999; 60/146,302, filed Jul. 29, 1999; 60/146,301, filed Jul. 29, 1999; 60/146,300, filed Jul. 29, 1999; and 60/146,299, filed Jul. 29, 1999. Each of the above-referenced provisional patent applications is incorporated herein by reference in its entirety.

FIELD OF THE INVENTION

The present invention relates to a composition and method for regulation of body weight and conditions related thereto, and particularly, to uses of proopiomelanocortin (POMC) peptides and analogs thereof to control body weight and conditions related thereto.

BACKGROUND OF THE INVENTION

The regulation of body weight, and particularly, obesity and conditions related thereto, is a major health concern throughout the world, and particularly in the United States, contributing to morbidity and mortality. Obesity is a metabolic disorder characterized by excessive accumulation of fat stores in adipose tissue. In humans, its causes are a complex interplay of genetics, environment and culture. It is well known that a regimen of diet and exercise leading to weight loss is the best approach for treating obesity, but unfortunately, such regimens are frequently unsuccessful. Oftentimes, an individual's inability to lose weight may be due to genetically inherited factors that contribute to increased appetite, a preference for high calorie foods, reduced physical activity and an abnormal metabolism. People inheriting or acquiring such predispositions are prone to obesity regardless of their efforts to combat the condition.

On the other side of the spectrum of body weight problems, other individuals suffer from one or more "wasting" disorders (e.g., wasting syndrome, cachexia, sarcopenia) which cause undesirable and/or unhealthy loss of weight or loss of body cell mass. In the elderly as well as in AIDS and cancer patients, wasting disease can result in undesired loss of body weight, including both the fat and the fat-free compartments. Wasting diseases can be the result of inadequate intake of food and/or metabolic changes related to illness and/or the aging process. Cancer patients and AIDS patients, as well as patients following extensive surgery or having chronic infections, immunologic diseases, hyperthyroidism, extraintestinal Crohn's disease, psychogenic disease, chronic heart failure or other severe trauma, frequently suffer from wasting disease which is sometimes also referred to as cachexia, a metabolic and, sometimes, an eating disorder. Cachexia is additionally characterized by hypermetabolism and hypercatabolism. Although cachexia and wasting disease are frequently used interchangeably to refer to wasting conditions, there is at least one body of research which differentiates cachexia from wasting syndrome as a loss of fat-free mass, and particularly, body cell mass (Mayer, 1999, *J. Nutr.* 129(1S Suppl.): 256S-259S). Sarcopenia, yet another such disorder which can affect the aging individual, is typically characterized by loss of muscle mass. End stage wasting disease as described above can develop in individuals suffering from either cachexia or sarcopenia.

In addition to the obvious health risks associated with being overweight or underweight, the tangential detrimental effects of such conditions are equally troublesome. For the obese individual, health effects can include a myriad of physical conditions related to, or affected by, excess body weight (e.g., cardiovascular disease, diabetes, cancer, hypertension, etc.) as well as physiological damage due to an overweight person's loss of self-esteem, depression, etc. For example, obesity, and particularly upper body obesity, is frequently associated with NIDDM. Non-insulin dependent diabetes mellitus (NIDDM or Type II diabetes) is a metabolic disorder that is characterized by the failure of body tissues to store carbohydrates at a normal rate. Resistance to the action of insulin is the most common characteristic of a Type II diabetic. When this resistance exceeds the capacity of the insulin-producing beta cells of the Islets of Langerhans to produce insulin, clinical diabetes results. In addition to NIDDM, being overweight, even in the absence of clinical obesity, can significantly increase the risk of developing certain other conditions, and/or of exacerbating the symptoms associated with the condition once developed. For example, the risk of inquiring several forms of cancer is increased in obese patients. Such cancers include breast cancer and colon cancer. Moreover, it has been known for years that excess body weight can be a risk factor for cardiovascular disease, hypertension, stroke and gall bladder disease. Obesity can also contribute to the risk of acquiring, or exacerbating, respiratory problems and osteoarthritis.

Other conditions that are frequently associated with excess gain of body weight are affective and mood disorders, including atypical depression or dysthymia. Some patients may alternatively experience undesired loss of body weight. It has previously been shown that in patients with an affective disorder characterized by higher than normal levels of HPA axis activity, leptin levels are also increased from normal levels in the blood of such patients (U.S. Pat. No. 5,866,547 to Flier et al., incorporated herein by reference in its entirety). High cerebrospinal fluid (brain) leptin levels are needed to suppress the increased activity of the HPA axis in these patients.

Another factor which can significantly contribute to an individual's propensity to gain weight and/or an inability to lose weight may be a side effect associated with one or more pharmaceutical compounds that the individual is taking to treat another condition. For example, epilepsy, attention deficit hyperactivity disorder (ADHD), and recently, migraine, are often treated with the drug, valproic acid, also known commercially as Depakote, which has the well known and undesirable side affect of increasing body weight. Other drugs having a similar side effect include lithium, commonly used for bipolar disorder (manic depression) and a several other antidepressants, including tricyclic antidepressants and several selective serotonin reuptake inhibitors (SSRIs) including fluoxetine, also known commercially as Prozac. There are a number of other drugs which have similar side effects, or the opposite side effect (i.e., undesired loss of body weight), including many drugs used for chemotherapy. Indeed, Such side effects can have serious implications for the patient's compliance with the drug therapy, as well as the patient's general well being and health. Indeed, many patients are likely to choose a lower body weight and greater self esteem over the treatment of what can be a disabling and destructive disorder, which reduces the ability of both patient and physician to maintain control over the disorder. When the disorder is a bipolar disorder, for example, non-compliance can be life-threatening.

For the underweight individual, conditions related to or affected by low body weight can include heart failure, susceptibility to infectious disease as a result of immune system weakness, and depression. Moreover, the rise in bulimia and anorexia in the past few decades is alarming, and illustrates the disturbing emphasis on ideal body size and shape regardless of the severe health consequences.

In 1963, Kennedy and Mitra proposed that puberty is linked to body weight and more specifically, to fat storage which is concluded to be one of the signals responsible for the initiation of hypothalamic control of ovarian function (*J. Physiol.* 166:408). Other researchers have proposed that the loss or restoration of menstrual cycles in young girls is related to a minimum weight for height (Frisch and McArthur, 1974, *Science* 185:949). Frisch and McArthur proposed that normal girls become relatively fatter from menarche to reproductive maturity. Taken together, these studies indicate that there is a relationship between the initiation of reproduction and adiposity. In support of this relationship were the observations that very lean young female ballet dancers and college rowers have a delayed puberty (Frisch et al., 1980, *NEJM* 303: 17 and Frisch et al., 1981, *JAMA* 246:1559), whereas obese girls have an acceleration of puberty (Zacharias et al., 1970, *Am. J. Obs. Gyn.* 108:833). The amenorrhea of extremely lean women was attributed to loss of fat and hypothalamic dysfunction (Vigersky et al., 1977, *NEJM* 297:1141). Based on such studies, Frisch et al. formed a hypothesis that a metabolic signal may be responsible for the initiation of reproduction, or the "critical weight" hypothesis (Frisch et al., 1970, *Science* 109:397). Frisch additionally proposed that adipose tissue is a direct regulator of female reproduction since it converts androgens to estrogens via aromatization (R. E. Frisch, 1990, *Adipose Tissue and Reproduction Progress in Reproductive Biology and Medicine*, vol. 14 and Sifteri, 1981, *J. Endocrinol.* 89:119).

Radical treatments to treat obesity include surgical procedures such as liposuction and stomach stapling. In addition, numerous drugs have been utilized in an effort to regulate a person's metabolism and/or to decrease appetite. Many of such drugs, however, have demonstrated harmful effects and have since been taken off of the market. Other replacement drug therapies have proven less effective, and the long term health consequences of such drugs are unknown. For the underweight individual, who may be suffering from undesired weight loss due to a disease such as cancer or AIDS, efforts to maintain or gain weight can be equally problematic.

Faced with such a long felt, but unsolved need for simple and effective methods for regulating body weight and for treating conditions associated with dysregulation of body weight, researchers, over the last several decades, have expended literally hundreds of millions of dollars to investigate compounds that can be used to treat body weight problems such as obesity without the negative implications experienced with other, previously tested, weight regulating drugs. While altering appetite can affect weight, so can the regulation of the fat stores in adipose tissue. This latter approach has been an under-appreciated field relative to regulation of appetite. For instance, compared to the list of compounds directed at inhibition of energy uptake (appetite suppressants), very few compounds have been identified which stimulate fat mobilization or suppress lipid sequestration.

Physiologists have postulated for years that, when a mammal overeats, the resulting excess fat stores signal to the brain that the body is obese which, in turn, causes the body to eat less and burn more dietary fat. G. R. Hervey, Nature (London), 227:629-631 (1969). This model of feedback inhibition is supported by parabiotic experiments, which implicates circulating hormones controlling adiposity. Genetic studies in model organisms, especially the mouse, have allowed the identification of molecules important for the regulation of body weight. These include leptin (Zhang et al., 1995, *Nature* 372:425-432, incorporated herein by reference in its entirety), a leptin receptor (Tartaglia et al., 1995, *Cell* 83:1263-1271) and a melanocortin receptor (Huszar et al., 1997, *Cell* 88:131-141).

Findings from several lines of investigations have placed proopiomelanocortin (POMC) and the peptides derived from it at a pivotal position in the central pathways for energy homeostasis. Obesity in the autosomal dominant lethal yellow ($A^y$/a) mouse, for example, is caused by ectopic expression of the agouti protein in the brain, where it antagonizes the melanocortin receptor 4 (MC4-R), a receptor found within the central nervous system (Lu et al., 1994, *Nature* 371:799-802). Agouti-related protein (AgRP) is normally expressed in the brain and antagonizes MC4-R. In transgenic mice, overexpression of AgRP results in obesity (Graham et al, 1997, *Nat. Genet.* 17:273-274 and Ollmann et al., 1997, *Science* 278:135-138). Targeted deletion of the MC4-R produces obesity similar to that of $A^y$ mice, which is characterized by both adult onset obesity and increased linear growth (Huszar et al., 1997, *Cell* 88:131-141). Pharmacological evidence has further suggested the importance of a melanocortinergic pathway in the central regulation (i.e., via the central nervous system) of energy balance: decreased feeding was observed after central administration of an MC4-R agonist ($\alpha$-MSH analog) to normal mice and increased feeding after central administration of a synthetic MC4-R antagonist to normal mice when measured for 12 hours (Fan et al., 1997, *Nature* 385:165-168). Further demonstrating the focus of previous investigators on the central pathways of energy homeostasis, PCT Publication WO 97/47316 and corresponding U.S. Pat. Nos. 5,908,609 and 5,932,779 to Lee et al., which are incorporated herein by reference in their entireties, disclose drug screening assays and diagnostic and therapeutic methods for treating body weight disorders by targeting the MC4R. Lee et al. describe identifying compounds that target MC4-R and describe administering such compounds so that delivery to the brain is optimized.

Understanding of the regulation of fat stores was greatly advanced by the discovery of leptin, the gene affected in the obese (ob) mutation. Leptin is secreted by adipose tissue, and its levels increase with increasing fat stores. Leptin is known to have both central and peripheral effects. There are high affinity receptors for leptin in the hypothalamus. Absence of either leptin or the leptin receptor leads to morbid obesity, presumably because the hypothalamus receives no fat signal, and accordingly acts as if the animal is completely without fat stores, and in some manner directs adipocytes to accumulate fat. The use of leptin to treat obesity in mice, however, requires very high, non-physiological doses. Thus, leptin alone has not been found to be a particularly useful anti-obesity agent.

To treat wasting and cachexia in patients such as the elderly, AIDS patients and cancer patients, anabolic steroids, growth hormone, dietary regimens, erythropoietin, cytokine therapy and anti-cytokine therapy, among other therapies, have been used to try to improve the condition of such patients. Such therapies cross a wide range of target cells, may have undesirable systemic side effects, may require toxic doses to work, and may not be sufficient to completely address the complex biological dysfunction related to different types of wasting disorders, however, and therefore, research is ongoing in the effort to find additional solutions to this problem.

Therefore, there remains a need in the art for a simple, safe and effective method for controlling body weight and for treating conditions related to or caused by undesired and/or health-compromising body weight.

SUMMARY OF THE INVENTION

While a majority of the prior art methods to regulate body weight have involved the regulation of appetite (i.e., by regulation of central pathways of energy homeostasis), the present invention is primarily directed to the regulation of the fat stores in adipose tissue (i.e., peripheral pathways of energy homeostasis). The present invention is specifically directed to a method and compound for controlling body weight (i.e., decreasing body weight, reducing weight gain, increasing body weight, or reducing weight loss) and conditions associated with or caused by undesirable body weight. Such a method comprises administering to an animal that is at risk for or has undesired body weight and/or a detrimental condition related thereto a therapeutic composition that regulates the peripheral melanocortinergic pathway and/or the leptinergic pathway of energy homeostasis.

One embodiment of the present invention relates to a method to regulate body weight in an animal, comprising administering to the animal a therapeutic composition comprising a proopiomelanocortin (POMC) compound, wherein the POMC compound is administered to the periphery of the animal in an amount effective to measurably regulate body weight in the animal, whereby administration of the compound minimizes delivery of the compound to the central nervous system of the animal. The POMC compound can include, but is not limited to, a melanocortin compound and a lipocortin compound. In a preferred embodiment, the compound is a melanocortin compound. Melanocortin compounds can include, for example, melanocyte stimulating hormone (MSH), a fragment of MSH, a is homologue of MSH, a peptide mimetic of MSH, a non-peptide mimetic of MSH, and a fusion protein comprising an MSH protein or fragment thereof. In one embodiment, the compound is selected from the group of α-MSH, β-MSH and γ-MSH. In another embodiment, the compound is a peptide mimetic of MSH. In a preferred embodiment, the compound is an analog of a peptide having an amino acid sequence represented herein by SEQ ID NO:2.

In one embodiment, the POMC compound is an α-MSH analog selected from the group of:
a. [Ac-Cys$^4$, D-Phe$^7$, Cys$^{10}$] α-MSH, wherein the Cys residues are connected by a disulfide bond;
b. Ac-[Nle$^4$, X$_{aa}^5$, His$^6$, X$_{aa}^7$, Arg$^7$, Trp$^9$, X$_{aa}^{10}$]-NH$_2$, (SEQ ID NO:3)
   wherein X$_{aa}^5$ is Glu or Asp, X$_{aa}^7$ is Phe or D-Phe and X$_{aa}^{10}$ is a dibasic amino acid; Lys; ornithine; 2,4,-diaminobutyric acid; or 2,3 diaminopropionic acid (Dpr);
c. Ac-[Cys$^4$, Cys$^{10}$]α-MSH$_{1-13}$NH$_2$;
d. R$_1$-W-X-Y-Z-R$_2$,
   wherein R$_1$ is selected from the group consisting of Ac-Gly-, Ac-Met-Glu-, Ac-Nle-Glu- and Ac-Tyr-Glu-;
   W is selected from the group consisting of -His- and -D-His-;
   X is selected from the group consisting of -Phe-, -D-Phe-, -Tyr-, -D-Tyr-, (-pNO$_2$)D-Phe$^7$-;
   Y is selected from the group consisting of -Arg- and -D-Arg-;
   Z is selected from the group consisting of -Trp- and -D-Trp-; and,
   R$_2$ is selected from the group consisting of —NH$_2$, -Gly-NH$_2$, and -Gly-Lys-NH$_2$;
e. Ac-Ser-Tyr-Ser-M-Glu-His-D-Phe-Arg-Trp-Gly-Lys-Pro-Val-NH$_2$ (SEQ ID NO:4),
   wherein M is selected from the group consisting of Met, Nle, and Cys;
f [Nle$^4$, D-Phe$^7$]-α-MSH;
g. [Nle$^4$, D-Phe$^7$]-α-MSH$_{4-10}$;
h. [Nle$^4$, D-Phe$^7$]-α-MSH$_{4-11}$;
i. [Nle$^4$, D-Phe$^7$, D-Trp$^9$]-α-MSH$_{4-11}$;
j. [Nle$^4$, D-Phe$^7$]-α-MSH$_{4-9}$;
k. Ac-[Nle$^4$, AA$^5$, D-Phe$^7$, AA$^{10}$]-R$_1$ or Ac-[Nle$^4$, AA$^5$, D-Phe$^7$, AA$^{11}$]-R$_2$;
   wherein AA$^5$ may be either a L- or D-amino acid having an omega amino or carboxyl group in the side chain, e.g., α,γ-diaminopropionic acid, α,γ-diaminobutyric acid, Orn, Lys, α,β-aminoadipic acid, α-aminopimelic acid, or higher homologs, Glu or Asp;
   wherein AA$^{10}$ may be diaminopropionic acid, α,γ-diaminobutyric acid, Orn, Lys, α,β-aminoadipic acid, α-aminopimelic acid, or higher homologs, Glu or Asp;
   wherein R$_1$ is the designation α-MSH$_{1-13}$NH$_2$, α-MSH$_{1-11}$NH$_2$, α-MSH$_{4-13}$NH$_2$, α-MSH$_{4-13}$NH$_2$, or α-MSH$_{4-10}$NH$_2$;
   wherein AA$^{11}$ may be L- or D-amino acid having an omega-amino or carboxyl group in the side chain, e.g., α,β-diaminopropionic acid; α,γ-diaminobutyric acid, Orn, Lys, α-aminoadipic acid, α-aminopimelic acid, or higher homologs, Glu or Asp;
   wherein R$_2$ is the designation α-MSH$_{1-13}$NH$_2$, α-MSH$_{1-12}$NH$_2$, α-MSH$_{1-11}$ NH$_2$, α-MSH$_{4-13}$NH$_2$, or α-MSH$_{4-10}$NH$_2$; and,
   wherein Xxx may be from 1 to 5 α-amino acid residues each of which may be of L- or D-configuration, or a linear or branched chain spacer;

(SEQ ID NO: 5)

l.

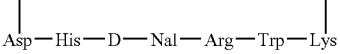

and (SEQ ID NO: 6)

m.

and, n.

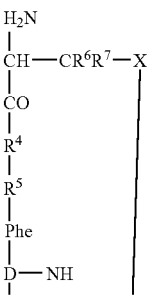

-continued

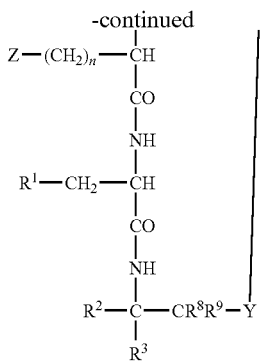

wherein R¹ is a substituted or unsubstituted aromatic radical;

R² is hydrogen or a methyl group;

R³ is a carboxylate, carboxamide, hydroxymethyl, or aldehyde group;

R⁴ is glutamic acid, alanine, -amino butyric acid, valine, leucine or isoleucine;

R⁵ is histidine, glutamic acid, alanine, valine, leucine or isoleucine;

R⁶ and R⁷, which may be the same or different, are hydrogen, methyl or lower alkyl having one to five carbon atoms;

R⁸ and R⁹, which may be the same or different, are hydrogen, methyl or lower alkyl having one to five carbon atoms;

X and Y are sulfur, methylene, SO or SO₂;

Z is —NH₂,

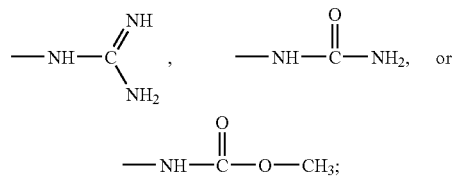

and, n is an integer greater than or equal to 2;

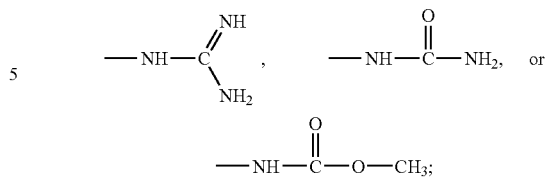

and, n is an integer greater than or equal to 2; and wherein the cyclized portion of the compound is conformationally restricted in a manner which is compatible with the reactivity of the compound with receptors of the central nervous system. In one aspect, the POMC compound is a peptide comprising an amino acid sequence represented by SEQ ID NO:1.

A POMC compound preferably has the following identifying characteristics: (1) an ability to bind to a POMC receptor that is expressed in peripheral tissues; and, (2) a biological activity selected from the group consisting of stimulation of lipolysis and inhibition of the uptake of fatty acids by adipocytes. The POMC receptor is preferably selected from the group of melanocortin 2-receptor (MC2-R) and melanocortin 5-receptor (MC5-R), with MC2-R being more preferred. In one embodiment, the POMC compound binds to a melanocortin receptor selected from the group consisting of MC2-R and melanocortin 5-receptor (MC5-R), with a higher affinity than to melanocortin-4 receptors (MC4-R). In another embodiment, the compound binds to a melanocortin receptor selected from the group consisting of MC2-R and melanocortin 5-receptor (MC5-R), and does not bind to any other melanocortin receptor under physiological conditions. In another embodiment, the compound binds to MC2-R, and does not bind to any other melanocortin receptor under physiological conditions. In yet another embodiment, the compound does not bind to MC4-R under physiological conditions. Preferably, the compound preferentially activates melanocortin-2 receptors (MC2-R) as compared to melanocortin-4 receptors (MC4-R). In one embodiment, compound does not activate MC4-R under physiological conditions. Preferably, administration of the compound is insufficient to cause a statistically significant change in the appetite of the animal as compared to before administration of the compound.

o.

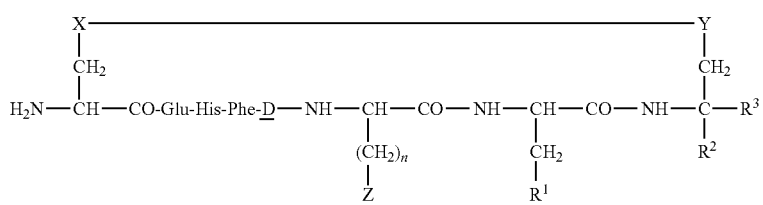

wherein R¹ is phenyl, indole, p-hydroxyphenyl, p-aminophenyl, imidazole, 1-naphthyl adamantyl or alkylphenyl, 2-naphthyl;

R² is hydrogen or a methyl group;

R³ is a carboxylate, carboxamide, hydroxymethyl, or aldehyde group;

X and Y are sulfur, methylene, SO or SO₂;

Z is —NH₂,

The therapeutic composition can be administered by a route selected from the group consisting of transdermally, topically, parenterally and orally. Preferably, the therapeutic composition is not administered directly to the central nervous system of the animal. In one embodiment, the therapeutic composition is administered in a controlled release formulation. A POMC compound is preferably administered in a dose of from about 0.1 μg to about 10 mg per kg body weight of the animal, and in another aspect, in a dose of from about 1 μg to about 10 mg per kg body weight of the animal. In one aspect, the POMC compound is administered in a dose of from about 40 μg to about 1 mg per kg body weight of the animal. Preferably, the POMC compound is from about 0.1% to about 90% of the therapeutic composition by weight, and in one embodiment, the POMC compound is from about 0.1% to about 1% of the therapeutic composition by weight. In one embodiment, the composition further comprises an antagonist of MC4-R. In another aspect, the composition further comprises an agent that inhibits binding of the POMC compound to an MC4-R. In another aspect, the composition further comprises an agent which inhibits the POMC compound from entering the central nervous system of the animal.

In one embodiment, the method is effective to measurably decrease body weight in the animal. A decrease in body weight in the animal can be measured within at least about two weeks of the step of administering the compound, and more preferably at least about one week, and more preferably at least about 3 days, and even more preferably at least about 24 hours of the step of administering the compound.

A preferred animal to which to administer the POMC compound includes an animal that has serum leptin levels between about 0 ng/ml and 50 ng/ml prior to the step of administration, and/or an animal that has serum MSH levels between about 0 ng/ml and 10 ng/ml prior to the step of administration. In one aspect, the animal has a ratio of serum MSH levels to serum leptin levels of greater than about 1:100 prior to the step of administration. In another aspect, the animal is a human having a body mass index (BMI) of greater than 27 kilograms per square meter.

In one embodiment, the composition further comprises another body weight regulating agent. Preferably, the body weight regulating agent is leptin. In this embodiment, the composition comprises a ratio of the POMC compound to leptin of about 1:100. In another aspect, the composition comprises the leptin in a dose of from about 0.1 μg to about 100 mg per kg body weight of the animal.

In another embodiment of the method of the present invention, the therapeutic composition is administered in an amount effective to measurably increase body weight in the animal or to decrease body weight loss in the animal. In one embodiment of this aspect of the present method, the POMC compound is combined with another body weight regulating agent. Such a body weight regulating agent can include, but is not limited to, an anabolic steroid, a growth hormone, erythropoietin, a cytokine, and an anti-cytokine agent. In this embodiment, the POMC compound is a proopiomelanocortin (POMC) antagonist compound. Preferably, the compound has the following identifying characteristics: (I) an ability to bind to a POMC receptor that is expressed in peripheral tissues; and, (2) a biological activity selected from the group consisting of inhibition of lipolysis and stimulation of the uptake of fatty acids by adipocytes. Preferably, the receptor is selected from the group of melanocortin 2-receptor (MC2-R) and melanocortin 5-receptor (MC5-R), with MC2-R being more preferred. Preferably, the antagonist compound is selected from the group consisting of a melanocortin antagonist compound and a lipocortin antagonist compound, with melanocortin antagonist compounds being more preferred. In one aspect, the antagonist compound is selected from the group of a fragment of MSH having MSH antagonist action, a homologue of MSH having MSH antagonist action, a peptide mimetic of MSH having MSH antagonist action, a non-peptide mimetic of MSH having MSH antagonist action, and a fusion protein comprising any of the MSH antagonist compounds. Preferably, the antagonist compound is selected from the group of α-MSH antagonist, β-MSH antagonist and γ-MSH antagonist. In one aspect, the antagonist compound is a peptide mimetic of MSH. In another aspect, the antagonist compound is an MSH analog selected from the group consisting of:

(SEQ ID NO: 5)
a.

Ac—Nle—Asp—His—D—Nal—Arg—Trp—Lys—NH$_2$; and (SEQ ID NO: 6)
b.

Ac—Nle—Asp—His—D-p-1—Phe—Arg—Trp—Lys—NH$_2$; and, c.

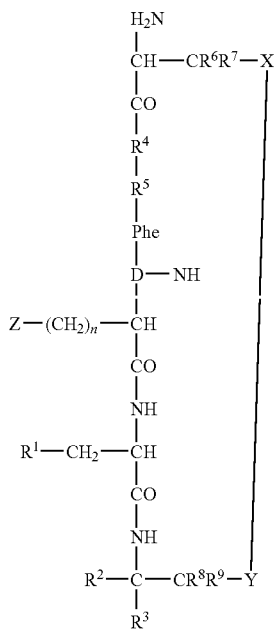

wherein $R^1$ is a substituted or unsubstituted aromatic radical;

$R^2$ is hydrogen or a methyl group;

$R^3$ is a carboxylate, carboxamide, hydroxymethyl, or aldehyde group;

$R^4$ is glutamic acid, alanine, -amino butyric acid, valine, leucine or isoleucine;

$R^5$ is histidine, glutamic acid, alanine, valine, leucine or isoleucine;

$R^6$ and $R^7$, which may be the same or different, are hydrogen, methyl or lower alkyl having one to five carbon atoms;

$R^8$ and $R^9$, which may be the same or different, are hydrogen, methyl or lower alkyl having one to five carbon atoms;

X and Y are sulfur, methylene, SO or SO$_2$;

Z is —NH$_2$,

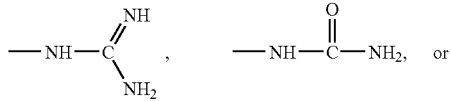

-continued

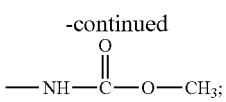

and,
n is an integer greater than or equal to 2; and, d.

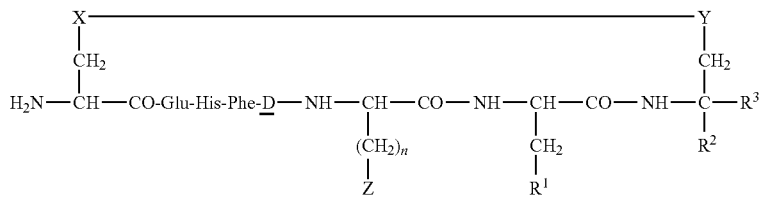

wherein $R^1$ is phenyl, indole, p-hydroxyphenyl, p-aminophenyl, imidazole, 1-naphthyl adamantyl or alkylphenyl, 2-naphthyl;

$R^2$ is hydrogen or a methyl group;

$R^3$ is a carboxylate, carboxamide, hydroxymethyl, or aldehyde group;

X and Y are sulfur, methylene, SO or $SO_2$;

Z is $—NH_2$,

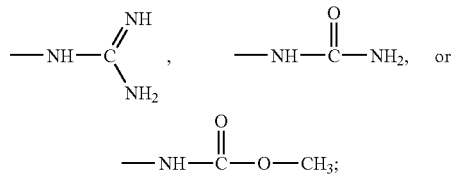

and,
n is an integer greater than or equal to 2; and wherein the cyclized portion of the compound is conformationally restricted in a manner which is compatible with the reactivity of the compound with receptors of the central nervous system.

Preferably, in the method of the present invention, the animal is a human.

Another embodiment of the present invention relates to a method for inhibition of free fatty acid uptake and/or stimulation of lipolysis in an animal, comprising administering to the periphery of an animal a POMC compound in an amount effective to produce a result selected from the group consisting of stimulation of lipolysis and inhibition of fatty acid uptake. In this embodiment, the amount is preferably insufficient to cause a statistically significant change in the appetite of the animal after administration of the compound as compared to before administration of the compound. Various aspects of such a method are as described for the methods above.

Yet another embodiment of the present invention relates to a method of regulating the body weight of an animal, comprising administering to an animal a POMC compound in an amount effective to bind to POMC receptors expressed by the animal in the animal's peripheral tissues, the effective amount: (a) being insufficient to substantially change the appetite of the animal after the step of administering as compared to before the step of administering; (b) being between about 0.1 µg and about 10 mg per kg of body weight of the animal; (c) being sufficient to affect a biological activity selected from the group consisting of: (i) lipolysis; and, (ii) uptake of fatty acids by adipocytes in the animal; and, (d) being effective to measurably increase or decrease the body weight of the animal after the compound has been administered to the animal. Various aspects of such a method are as described for the methods above.

Another embodiment of the present invention relates to a method to regulate body weight in an animal, comprising modulating the activity of a melanocortin receptor selected from the group consisting of melanocortin 2-receptor and melanocortin 5-receptor. In this embodiment, the melanocortin receptor is preferably a melanocortin 2-receptor. The step of modulating can include administering to the periphery of the animal a compound which regulates the melanocortin receptor. The compound can include, but is not limited to a POMC compound, an antibody that selectively binds to the melanocortin receptor, and a soluble melanocortin receptor. The step of modulating can include, in one embodiment, administering an effective amount of a compound that increases expression of the melanocortin 2-receptor and induces weight loss. The step of modulating preferably comprises administering an effective amount of a compound that decreases expression of the melanocortin 2-receptor and induces weight gain. Various aspects of such a method are as described for the methods above.

Yet another embodiment of the present invention relates to a method for regulating metabolic efficiency in an animal, comprising: (a) measuring serum MSH levels in an animal; (b) identifying animals having serum MSH levels of less than about 0.1 ng/ml; and, (c) administering to the periphery of the animals identified in (b) a composition comprising a compound selected from the group consisting of a POMC compound and leptin, wherein the compound is administered in an amount effective to increase serum MSH levels in the animal to level effective to produce a result selected from the group consisting of stimulating lipolysis and inhibiting fatty acid uptake in the animal. Preferably, the compound is administered in an amount effective to produce a measurable decrease in body weight of the animal. Various aspects of such a method are as described for the methods above.

Another embodiment of the present invention relates to a therapeutic composition that regulates the peripheral melanocortinergic and/or leptinergic pathways of energy homeostasis in an animal, comprising: (a) a first body weight regulating agent that is a proopiomelanocortin (POMC) compound; and, (b) a second body weight regulating agent that is not a proopiomelanocortin (POMC) compound. The POMC compound is preferably a POMC compound as described above, preferably provided in the doses and formulated as described above.

In one embodiment, the second body weight regulating agent is leptin. Preferably, the composition comprises a ratio of the POMC compound to leptin of 1:100, and in another aspect, a ratio of the POMC compound to leptin of 1:25, and in another aspect, a ratio of the POMC compound to leptin of 1:10. The dose of leptin is preferably from about 0.1 µg to about 100 mg per kg body weight of the animal, and more preferably, from about 0.1 µg to about 10 mg per kg body weight of the animal, and in another aspect, is from about 1 µg to about 10 mg per kg body weight of the animal. In another embodiment, the second body weight regulating agent is selected from the group consisting of an anabolic steroid, a growth hormone, erythropoietin, a cytokine, and an anti-cytokine agent. The therapeutic composition preferably further comprises a pharmaceutically acceptable excipient. Such a pharmaceutically acceptable excipient can, in one embodiment, prolong the presence of the therapeutic composition in the bloodstream of a animal.

Yet another embodiment of the present invention relates to a method for treating an affective and mood disorder in an animal, comprising administering to an animal at risk for or suffering from an affective mood disorder a therapeutic composition comprising a proopiomelanocortin (POMC) compound, wherein the POMC compound is administered to the periphery of the animal in an amount effective to measurably ameliorate the disorder in the animal, whereby administration of the compound minimizes delivery of the compound to the central nervous system of the animal. The affective and mood disorder can include, but is not limited to, depression and dysthymia. In one aspect, the depression is atypical depression.

Another embodiment of the present invention relates to a method to treat an obesity-associated disorder in an animal, comprising administering to an animal suffering from or at risk for an obesity-associated disorder a therapeutic composition comprising a proopiomelanocortin (POMC) compound, wherein the POMC compound is administered to the periphery of the animal in an amount effective to measurably decrease body weight or weight gain in the animal, whereby administration of the compound minimizes delivery of the compound to the central nervous system of the animal. The obesity-associated disorder can include, but is not limited to, non-insulin dependent diabetes mellitus, cardiovascular disease, cancer, hypertension, osteoarthritis, stroke, respiratory problems, and gall bladder disease.

Another embodiment of the present invention relates to a method for treating a reproductive disorder in an animal, comprising administering to an animal at risk for or suffering from a reproductive disorder a therapeutic composition comprising a proopiomelanocortin (POMC) compound, wherein the POMC compound is administered to the periphery of the animal in an amount effective to prevent or ameliorate the disorder, whereby administration of the compound minimizes delivery of the compound to the central nervous system of the animal. In one embodiment, the reproductive disorder includes, but is not limited to, amenorrhea, an inability or reduced ability to ovulate, an inability to conceive, an inability or reduced ability to maintain a pregnancy, an inability or reduced ability to lactate, an inability or reduced ability to deliver a full-term offspring, and an inability or reduced ability to impregnate a female.

Yet another embodiment of the present invention relates to a method to control undesired body weight which is a side effect resulting from administration of a pharmaceutical compound, comprising administering to an animal at risk of or suffering from undesired body weight which is a side effect resulting from administration of a pharmaceutical compound, a therapeutic composition comprising a proopiomelanocortin (POMC) compound wherein the POMC compound is administered to the periphery of the animal in an amount effective to measurably decrease body weight or weight gain in the animal, whereby administration of the compound minimizes delivery of the compound to the central nervous system of the animal. In one embodiment, the pharmaceutical compound includes, but is not limited to, valproic acid, lithium, tricyclic antidepressants, and selective serotonin reuptake inhibitors (SSRI).

Another embodiment of the present invention relates to a food composition that regulates the peripheral melanocortinergic and/or leptinergic pathways of energy homeostasis, comprising a proopiomelanocortin (POMC) compound. Preferably, the food composition is effective to measurably regulate body weight in the animal, and wherein delivery of the compound to the central nervous system of the animal is minimized.

Yet another embodiment of the present invention relates to a method to increase the body weight and/or mass in an animal having an eating disorder, comprising administering to the animal a therapeutic composition comprising a proopiomelanocortin (POMC) antagonist compound, wherein the POMC compound is administered to the periphery of the animal in an amount effective to measurably increase body weight or reduce body weight loss in the animal, whereby administration of the compound minimizes delivery of the compound to the central nervous system of the animal. In one embodiment, the eating disorder is selected from the group consisting of anorexia and bulimia.

BRIEF DESCRIPTION OF THE DRAWINGS OF THE INVENTION

FIG. 1A is a schematic diagrams and restriction map of the mouse POMC locus, the targeting vector, and the predicted structure of the POMC locus after homologous recombination.

FIG. 1B is a scanned image of a Southern blot analysis of tail DNAs from $F_2$ littermates.

FIG. 1C is a bar graph showing a radioimmunoassay (RIA) analysis of serum ACTH levels in $F_2$ male littermates.

FIG. 3A is a bar graph showing that corticosterone levels in mutant POMC mice were below the detection limit of the RIA.

FIG. 3B is a bar graph showing that aldosterone levels in mutant POMC mice were below the detection limit of the RIA.

FIG. 3C is a bar graph showing that epinephrine levels were significantly lower in mutant POMC mice as compared to wildtype mice.

FIG. 3D is a bar graph showing that norepinephrine levels were not significantly different in mutant POMC mice as compared to wildtype mice.

FIG. 3E is a bar graph showing that dopamine levels were slightly increased in mutant POMC mice as compared to wildtype mice.

DETAILED DESCRIPTION OF THE INVENTION

Figure 2A:
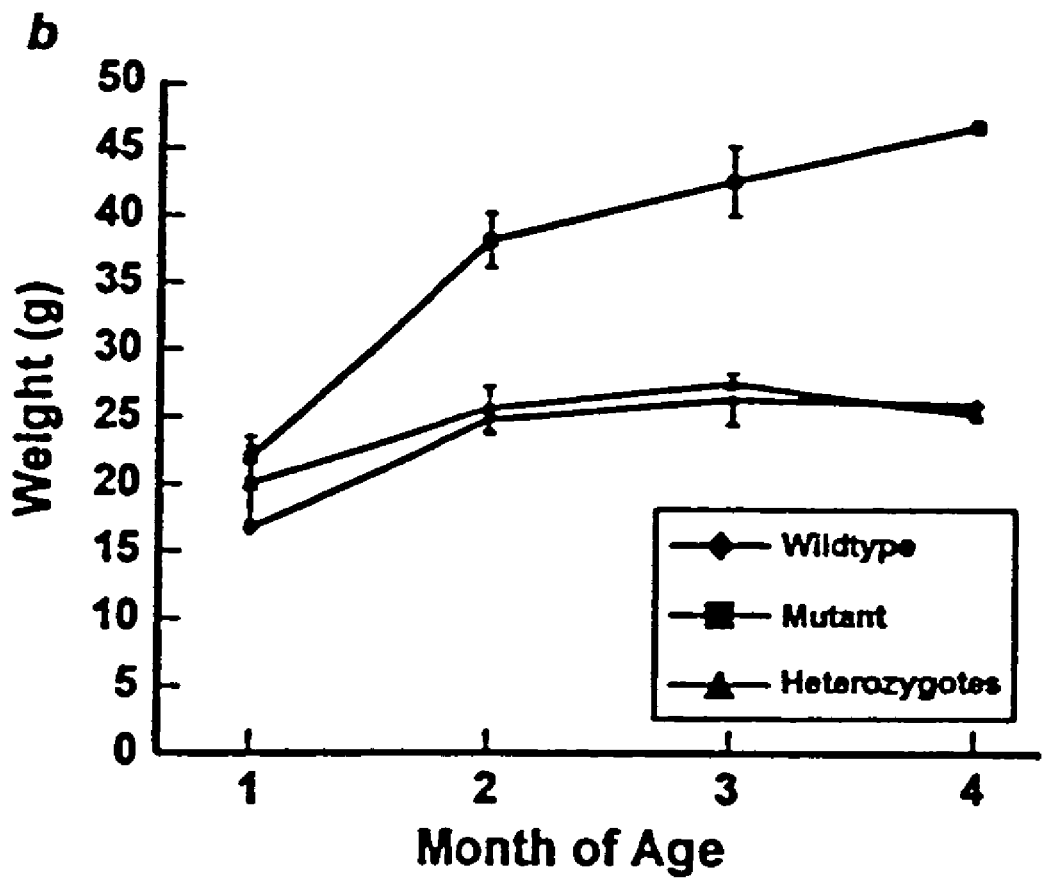
FIG. 2A is a line graph of weight measurements taken from male mice of wildtype and mutant POMC genotype.

The present invention generally relates to compositions and methods for regulating body weight in an animal and for treating or preventing conditions related thereto, and particularly, health-compromising conditions related thereto. According to the present invention, to "control" or "regulate" body weight, can refer to reducing body weight, increasing body weight, reducing the rate of weight gain, or reducing the rate of weight loss, and includes actively maintaining, or not significantly changing body weight (e.g., against external or internal influences which may otherwise increase or decrease body weight). One embodiment of the present invention relates to regulating body weight by administering to the periphery of an animal a proopiomelanocortin (POMC) compound, which can include a POMC peptide, a fragment thereof, a homologue thereof, a peptide or non-peptide mimetic thereof, a fusion protein including such peptide, a pharmaceutically acceptable salt thereof, or a recombinant nucleic acid molecule encoding such a POMC peptide, fragment, homologue, peptide mimetic, or fusion protein thereof, and includes both POMC agonists and antagonists. In a preferred embodiment, the POMC compound is a melanocyte stimulating hormone (MSH) compound. The POMC compound is administered in an amount effective to measurably regulate body weight in the animal, whereby administration of the compound minimizes delivery of the compound to the central nervous system of the animal. These aspects of the invention are discussed in detail below.

In one aspect, the present invention relates to reducing body weight and/or reducing weight gain in an animal, and more particularly, to treating or ameliorating obesity in patients at risk for or suffering from obesity. In another aspect, the present invention is directed to a method and compound for treating an animal that is unable to gain or retain weight (e.g., an animal with a wasting syndrome). Such a method is effective to increase body weight and/or mass, or to reduce weight and/or mass loss, or to improve conditions associated with or caused by undesirably low (e.g., unhealthy) body weight and/or mass. In the former aspect, discussed in detail below, the method comprises administering to an animal a POMC compound having POMC agonist biological activity, including both naturally occurring POMC peptides and homologues or mimetics thereof. In the latter aspect, which is also discussed in detail below, the method comprises administering to an animal that is at risk for developing or has low body weight and/or a detrimental condition related thereto, a POMC antagonist compound, and preferably, a homologue or mimetic of a POMC peptide. Such a compound has antagonistic biological activity (i.e., an antagonist of the prototype peptide) as compared to the naturally occurring POMC peptide (i.e., prototype) upon which the homologue or mimetic is based. The POMC compound is administered peripherally in an amount effective to induce a measurable decrease or increase in the body weight and/or mass of the animal, or minimally, to increase the rate of gain or reduce the rate of loss of body weight and/or mass in the animal. The POMC compound can be administered in conjunction with one or more other compounds that are useful for regulating body weight and/or mass, and particularly, for decreasing or increasing body weight in an animal. Preferably, decreasing or increasing body weight and/or mass and/or increasing or reducing the rate of weight and/or mass loss/gain in an animal is effective for treating or ameliorating undesired and/or health-compromising conditions associated with low or high body weight, such conditions being discussed in detail herein.

More particularly, the present invention relates to the inventors' discovery that administration of a proopiomelanocortin (POMC) peptide agonist to an animal suffering from obesity reduces obesity in the animal. Included in the invention is a method for modifying the peripheral melanocortinergic pathways for controlling obesity in patients at risk of, or suffering from, obesity and/or conditions associated therewith, by administering an effective amount of circulating melanocyte stimulating hormone (MSH) or analogs (e.g., homologues or mimetics) thereof, alone or in combination with leptin or other body weight regulating drugs. Additionally, the present invention relates to a proopiomelanocortin null mutant mouse model for studying the human proopiomelanocortin null syndrome (described in detail in copending U.S. application Ser. No. 09/374,827, filed Aug. 12, 1999, incorporated herein by reference in its entirety).

As discussed in the background section, prior to the present invention, findings from several lines of investigations have placed proopiomelanocortin (POMC) and the peptides derived from it at a pivotal position in the central pathways for energy homeostasis (Lu et al., 1994, supra, Graham et al., 1997, supra, Ollmann et al., 1997, supra, Huzar et al., 1997, supra, Fan et al., 1997, supra, PCT Publication WO 97/47316, supra, U.S. Pat. No. 5,908,609, supra and U.S. Pat. No. 5,932, 779, supra). However, while other investigators have focused on this recognition that proopiomelanocortins (POMC) are involved in the central pathways for energy homeostasis (i.e., regulation through the central nervous system and brain receptors), the present inventors were the first to appreciate the role of POMC peptides in the regulation of peripheral pathways of energy homeostasis (i.e., adipocyte regulation through inhibition of free fatty acid uptake and/or stimulation of lipolysis). The present inventors discovered the role of POMC peptides in the regulation of peripheral energy homeostasis through the development and study of mice with a targeted deletion of the POMC gene and by the administration of an MSH agonist to such mice.

The data from previous investigators which suggested a central nervous system (hypothalamic) effect of melanocortins on appetite, and the present inventors' data which demonstrates a peripheral action of melanocortins on fatty acid metabolism, have led the present inventors to propose the following mechanism for the novel method of the present invention. Without being bound by theory, the present inventors believe that the method of the present invention, while it may have some impact on the central melanocortinergic pathways of energy homeostasis, is primarily effective for regulating adipocyte/fatty acid metabolism. In support of this belief, it is noted that the molar concentration of a melanocortin agonist that would be necessary to effect a transient decrease in food intake (i.e., via the central nervous system and the melanocortin 4-receptor) is one hundred-fold higher than that required to accomplish weight reduction in obese mice or to prevent weight gain in a mouse that is genetically predisposed to obesity. Also without being bound by theory, the present inventors believe that under some physiological conditions, an organism is compelled both to suppress appetite and to metabolize fat stores from peripheral adipose tissue. Secretion of melanocortins in the hypothalamus serves to suppress appetite and, after diffusion to the periphery, melanocortins from the hypothalamus, and possibly elsewhere, stimulate lipolysis from adipocytes. It is significant that the amount of melanocortin agonist necessary to effect a decrease in appetite when applied directly to the hypothalamus is equivalent to the amount necessary to effect a decrease in fatty acid accumulation when applied peripherally. In the normal course of events (i.e., in the endogenous system of a normal animal), melanocortins are produced in the hypothalamus and then diffuse to the periphery. It follows that cells in the hypothalamus should be less sensitive to melanocortins and cells in the periphery more sensitive. Again, this is consistent with the present inventors' findings that the amount of peripherally administered melanocortin agonist needed to effect body weight homeostasis is at least two orders of magnitude lower than that required to effect a change in appetite.

The discovery by the present inventors of the present methods and compositions provides particular advantages compared to previously described methods of weight control, in that when the POMC compounds as described herein are applied peripherally according to the method of the present invention, rather than produced centrally, the effects of the compound will be substantially restricted to the periphery, since the central nervous system concentrations will not approach those necessary to have a significant impact on hyperphagia. Thus, the method of the present invention takes advantage of the differential sensitivities of the central nervous system and peripheral tissues to POMC compounds, such as melanocortins. By applying a POMC compound as described herein peripherally, when the naturally occurring form of such compound is normally produced centrally, peripheral effects are stimulated while central nervous system effects are mitigated. For example, a change in the metabolism of fatty acids may be affected without direct alteration of the appetite of the patient.

Moreover, prior to the present invention, without the discovery by the present inventors that POMC compounds administered peripherally will act peripherally to regulate body weight, it would have been inconceivable to consider using a POMC peptide to control body weight in humans, because, as mentioned above, the concentrations of POMC compound that would be necessary to affect the central nervous system (the only mechanism known prior to the present invention) by peripheral administration are physiologically unreasonable, if not impossible. Furthermore, to administer such compounds directly to the central nervous system would be unthinkable as a therapeutic method for use in humans. Therefore, the present inventors' discovery represents a previously unappreciated frontier in body weight control.

In addition, by taking advantage of the scientific knowledge gained from the discovery regarding weight loss, the present inventors have also discovered a method for modifying the peripheral melanocortinergic pathways for increasing body weight or body mass in patients at risk of, or suffering from, undesirable and/or unhealthy weight and/or mass loss, by administering an effective amount of circulating POMC analogs (e.g., homologues or mimetics) having POMC antagonist action, and particularly, melanocyte stimulating hormone (MSH) analog antagonists, alone or in combination with other body weight regulating drugs (e.g., anabolic steroids, growth hormone, erythropoietin, cytokines, and anti-cytokine agents).

According to the present invention, "undesirable" gain of body weight and/or mass refers to any gain of body weight or body mass (i.e., gain of body mass can occur in the absence of measurable or significant weight gain) in an individual, as compared to a prior weight or body mass of that individual, where such weight and/or mass gain is unintended, unexpected, and/or unhealthy, as determined by the individual or by a medical professional evaluating such individual. Similarly, "unhealthy" or "health-compromising" weight and/or mass gain is referred to herein as any gain of body weight or body mass which is either deemed by the individual or medical professional to be unhealthy, or which results in a symptom that can be associated with poor health, such as diabetes or cardiovascular conditions. Accordingly, "undesirable" loss of body weight and/or mass refers to any loss of body weight or body mass (i.e., loss of body mass can occur in the absence of measurable or significant weight gain) in an individual, as compared to a prior weight or body mass of that individual, where such weight and/or mass loss is unintended, unexpected, and/or unhealthy, as determined by the individual or by a medical professional evaluating such individual. Similarly, "unhealthy" or "health-compromising" weight and/or mass loss is referred to herein as any loss of body weight or body mass which is either deemed by the individual or medical professional to be unhealthy, or which results in a symptom that can be associated with poor health, such as heart problems, weakened immune function, lack of strength or energy, and/or depression.

The method of the present invention is useful for treating any condition or disorder that is characterized by or associated with undesirable or unhealthy body weight or body mass gain or loss. With regard to undesirable or unhealthy body weight or body mass gain, such conditions include, but are not limited to non-insulin dependent diabetes mellitus (NIDDM), cardiovascular disease, cancer, hypertension, osteoarthritis, stroke, respiratory problems and gall bladder disease. Other conditions associated with undesirable or unhealthy body weight or body mass gain, such conditions include but are not limited to depression mood disorders, reproductive dysfunction, and pharmaceutical non-compliance. With regard to undesirable or unhealthy body weight or body mass gain, such conditions, include, but are not limited to wasting syndromes (e.g., wasting disease, cachexia and sarcopenia) and conditions associated with such syndromes, including, but not limited to, aging, cancer, AIDS (or HIV infection), extensive surgery, chronic infections, immunologic diseases, hyperthyroidism, extraintestinal Crohn's disease, psychogenic disease, chronic heart failure or other severe trauma. According to the present invention, the phrase "wasting syndrome" is used generally to refer to any condition characterized by undesirable weight and/or body mass loss. The term "cachexia" is used to refer to a metabolic and sometimes, eating disorder, which is additionally characterized by hypermetabolism and hypercatabolism, and which results in a loss of fat-free mass, and particularly, body cell mass. "Sarcopenia" refers to yet another such disorder which is typically characterized by loss of muscle mass. The term "wasting disease" is used to more specifically refer to loss of body weight, including both the fat and the fat-free compartments, which is typically found in the elderly, or in late stage cachexia or sarcopenia.

In the method of the present invention, therapeutic compositions can be administered to any animal, and preferably, to any member of the Vertebrate class, Mammalia, including, without limitation, primates, rodents, livestock and domestic pets. Livestock include mammals to be consumed or that produce useful products (e.g., sheep for wool production). Preferred mammals to treat include humans. According to the present invention, the term "patient" or "individual" is used to describe both human and non-human animals. In a preferred embodiment, the present method is used for treating obese patients having abnormal (e.g., high or low as compared to a substantially healthy individual of medically normal body weight and/or mass) endogenous levels of circulating MSH or leptin or both.

Proopiomelanocortin (POMC) peptides, including the melanocortins: adrenocorticotrophin (ACTH); $\alpha$-, $\beta$- and $\gamma$-melanocyte stimulating hormones (MSH); and the opioid receptor ligand $\beta$-endorphin, have a diverse array of biological activities, including roles in pigmentation, adrenocortical function, regulation of energy stores, and the immune, central nervous and peripheral circulation system (Smith, A. I. et al., *Endocr Rev* 9, 159-179 (1988); König, "Peptide and protein hormones: structure, regulation, activity, a reference manual" (Weinheim; NY 1993)).

The POMC mutant mouse developed by the present inventors and described herein is a model of obesity that was engineered to carry an autosomal recessive null allele of the POMC gene. This mutant lacks all of the peptide hormones encoded by this locus. The present inventors have discovered that mice lacking the POMC peptides have obesity, a defect in adrenal development, and altered pigmentation. This phenotype is similar to the recently identified human POMC mutants (Krude, et al., 1998, *Nat Genet* 19, 155-7). In addition to a disregulation of fat metabolism, the POMC-deficient mice showed increased food intake. When the inventors treated the mutant mice peripherally with a stable α-MSH agonist, these mice lost over 40% of their excess weight after two weeks, whereas wildtype non-obese mice did not lose significant weight. The present inventors have shown that the weight changes in POMC null mice are not simply regulated through feeding behavior, but rather through both central and peripheral actions of melanocortins. Based on in vivo experiments described herein, the present inventors have shown MSH to be an adiposity regulating hormone. Peripheral treatment of pomc/pomc and ob/ob mutants with an MSH mimetic ameliorated obesity, but did not significantly diminish weight in normal mice. Consequently, these results indicate that certain subpopulations of obese patients will be particularly amenable to treatment with MSH and homologues and mimetics thereof, although the present invention encompasses the use of POMC compounds to treat any patient with undesired body weight. Pharmacological agents which are biologically active and mimic the activity of MSH are therefore useful for treating obese patients, particularly those with abnormal levels of circulating MSH. The present inventors are the first to appreciate that the POMC peptides have both a central and peripheral effect on feeding behavior and on body weight regulation. Similarly, pharmacological agents which are biologically active and antagonize the activity of endogenous MSH are therefore useful for treating patients with undesired weight and/or mass loss conditions, such as cachexia.

Furthermore, the present inventors have demonstrated that the POMC null mutant mouse is a model for studying the human POMC null syndrome. In addition to being a mouse model for the human POMC deficiency, the POMC mutant mouse is a valuable addition to the growing number of murine obesity models, aiding in the dissection of the mechanisms of energy homeostasis, centrally and peripherally, as well as in exploring therapeutic regimens for the human POMC deficient patients and possibly for other, multigenic-multifactorial forms of human obesity. The anti-obesity effects of MSH indicate a therapeutic use in POMC-deficient as well as other forms of obesity.

One embodiment of the present invention relates to a method to regulate body weight in an animal (e.g., a human patient). Such a method includes the step of administering to the animal a therapeutic composition that includes a POMC compound. According to the present invention, the phrase "POMC compound" encompasses any of the following compounds: a POMC peptide (i.e., a peptide encoded by the POMC gene), a fragment of such a peptide (including both biologically active and inactive fragments), a homologue of such a peptide, a mimetic (peptide or non-peptide) of such a peptide, a fusion protein comprising such a peptide, and any pharmaceutical salts of such a peptide. In addition, peptides useful in the present invention may exist, particularly when formulated, as dimers, trimers, tetramers, and other multimers. Such multimers are included within the scope of the present invention. As used herein, the term "analog", as used in connection with a POMC peptide according to the present invention, refers generically to any homologue or mimetic (peptide or non-peptide) of a POMC peptide. Analogs can include both agonists and antagonists of the prototype POMC peptide, unless specifically used in connection with the term "antagonist" or "agonist". The phrase "POMC agonist compound" or "POMC agonist" refers to any fragment, homologue or mimetic (peptide or non-peptide) of a POMC peptide (i.e., a naturally occurring or prototype) which is characterized by its ability to agonize (e.g., stimulate, induce, increase, enhance) the biological activity of the naturally occurring POMC peptide (e.g., interaction/binding with and/or activation of a POMC receptor). The phrase "POMC antagonist compound" or "POMC antagonist" refers to any fragment, homologue or mimetic (peptide or non-peptide) of a POMC peptide (i.e., naturally occurring or prototype) which is characterized by its ability to antagonize (e.g., inhibit, block, decrease, compete against) the biological activity of the naturally occurring POMC peptide (e.g., interaction/binding with and/or activation of a POMC receptor). Terms used herein in connection with POMC genes and proteins (e.g., "compound", "analog", "homologue", "mimetic") can be similarly used with specific POMC genes and proteins (e.g., an MSH peptide, an MSH compound, an MSH analog, etc.). Homologues and mimetics are described in detail below. In one embodiment of the present invention, a POMC compound is an isolated nucleic acid molecule that encodes a POMC peptide, a peptide analog thereof, or a fusion protein comprising such a peptide. In addition, peptides useful in the present invention may exist, particularly when formulated, as dimers, trimers, tetramers, and other multimers. Such multimers are included within the scope of the present invention.

For embodiments of the present invention related to decreasing body weight and/or decreasing the rate of weight gain, preferably, POMC compounds according to the present invention are any compound having one or more of the following properties or identifying characteristics: (1) an ability to bind to a POMC peptide receptor, and particularly, to a POMC receptor that is expressed in peripheral (as opposed to central nervous system) tissues; and, (2) an ability to stimulate lipolysis and/or to inhibit the uptake of fatty acids by adipocytes. Particularly preferred POMC compounds for use in the present method include homologues and mimetics of naturally occurring POMC peptides which have substantially similar, or even more preferably, enhanced, properties or identifying characteristics as compared to the naturally occurring (i.e., prototype) POMC peptide (e.g., agonists). Such properties or identifying characteristics include: (1) enhanced ability to bind to a POMC peptide receptor, and particularly, to a POMC receptor that is expressed in peripheral (as opposed to central nervous system) tissues; (2) enhanced serum half-life (i.e., enhanced stability under physiological conditions); and/or (3) enhanced ability to stimulate lipolysis and/or to inhibit the uptake of fatty acids by adipocytes.

For embodiments of the present invention related to increasing body weight and/or decreasing the rate of weight loss, preferably, POMC compounds according to the present invention are any compound having one or more of the following properties or identifying characteristics: (1) an ability to bind to a POMC peptide receptor, and particularly, to a POMC receptor that is expressed in peripheral (as opposed to central nervous system) tissues; and, (2) an ability to inhibit lipolysis and/or to increase the uptake of fatty acids by adipocytes. Particularly preferred POMC compounds for use in this embodiment include homologues or mimetics of a POMC peptide which block or inhibit the action of a naturally occurring POMC-peptide (i.e., an antagonist), such that a patient's ability to gain weight and/or mass or avoid undesirable weight and/or mass loss is improved (i.e., a POMC antagonist compound). The desirable properties of a POMC antagonist compound include a decreased ability to stimulate lipolysis and/or to inhibit the uptake of fatty acids by adipocytes (or an ability to inhibit lipolysis and/or to stimulate the uptake of fatty acids by adipocytes), while serum half-life and receptor binding abilities (for blocking, but not activating the receptor) are preferably substantially similar or enhanced compared to the naturally occurring peptide.

Peripheral adipocytes are known to express two different melanocortin receptors, melanocortin 2-receptor (MC2-R) and melanocortin 5-receptor (MC5-R). Without being bound by theory, the present inventors believe that of these two peripheral melanocortin receptors, the MC2-R is the most important in controlling the peripheral pathways of energy homeostasis, although both receptors may play roles in this process. Prior to the present invention, other investigators had shown relatively little interest in the properties of the MC2-R, however, the present inventors have provided evidence herein that this receptor, alone and/or in combination with the MC5-R, plays a significant role in the regulation of peripheral metabolic efficiency. Therefore, in a preferred embodiment of the present invention, a POMC compound of the present invention has an ability to bind to (e.g., interact with) the melanocortin 2-receptor and/or the melanocortin 5-receptor, with the melanocortin 2-receptor being more preferred. With regard to the embodiment for decreasing body weight in an animal, preferably, a POMC compound has an ability to activate or increase the activation of the melanocortin 2-receptor and/or the melanocortin 5-receptor. With regard to the embodiment for increasing body weight in an animal, preferably, a POMC compound has an ability to block activation of, inhibit activation of or decrease activation of the melanocortin 2-receptor and/or the melanocortin 5-receptor (i.e., a POMC antagonist, which could also be referred to as an antagonist of a POMC receptor).

As discussed above, it is an advantage of the method of the present invention that the effect of the POMC peptide administration is substantially restricted to the periphery, so that body weight and/or mass of an animal can be regulated in the absence of significantly affecting the appetite of the animal. As the present inventors have discovered, it is not necessary to have a significant, if any, primary effect on appetite to affect weight loss in an anima. As will be discussed in detail below, this advantage of the present invention is most easily achieved by administration of the POMC compound peripherally (i.e., by a route that does not deliver the compound directly or preferentially to the central nervous system and especially the brain). When a POMC compound is administered peripherally in an amount effective to act on peripheral receptors while mitigating effects on central receptors (e.g., the molar concentration of a melanocortin agonist that would be necessary to effect a transient decrease in food intake via the central nervous system and the melanocortin 4-receptor when delivered peripherally is at least one hundred-fold higher than that required to accomplish weight reduction via peripheral receptors, and is likely to be toxic), no additional modification of the POMC peptide is necessary. However, in one embodiment of the invention, the potential for effects on the central nervous system can be further minimized by selecting POMC compounds that preferentially bind to and/or activate/inhibit the peripheral melanocortin receptors as compared to the central melanocortin receptors, and particularly melanocortin 4-receptor (MC4-R). In one embodiment of the present invention, the administration of the POMC compound is insufficient to cause a statistically significant change in the appetite of the animal as compared to the appetite of the animal prior to administration of the compound. According to the present invention, "insufficient to substantially change" or "insufficient to statistically significantly change" the appetite of an animal refers to an inability to produce a measurable change in the appetite of an animal that is statistically different than the measured appetite of the animal prior to a treatment. Appetite changes can be measured, for example, by monitoring food intake and for humans, can include objective or subjective analysis of appetite changes.

In one embodiment, wherein decrease in body weight and/or mass is the goal, a preferred POMC compound: (1) binds to an MC2-R and/or MC5-R with a higher affinity (or avidity) than to an MC4-R; and/or (2) activates an MC2-R and/or MC5-R to a greater degree or preferentially as compared to an MC4-R. In another embodiment, a preferred POMC compound binds to and/or activates an MC2-R and/or an MC5-R, and does not bind to, binds with very low affinity to (i.e., whereby the receptor is not activated or is not activated to a degree to provide a significant biological activity), and/or does not substantially activate, any other melanocortin receptor under physiological conditions. In yet another embodiment, a preferred POMC compound does not bind to, binds with very low affinity to, and/or does not substantially activate an MC4-R under physiological conditions. In another embodiment, wherein an increase in body weight and/or mass is the goal, although the POMC compound preferably binds to an MC2-R and/or MC5-R with a higher affinity (or avidity) than to an MC4-R in order to minimize central nervous system effects, the POMC compound (e.g., an antagonist), preferably inhibits the activation of an MC2-R and/or MC5-R. In addition to POMC antagonist compounds as described above, an antibody that binds to and blocks the receptor and/or a soluble MC2-R or MC5-R that competes with the endogenous receptor can be administered.

Preferably, a POMC compound that binds to an MC2-R or an MC5-R binds to such receptors with at least a 10 fold greater affinity or avidity as compared to binding to an MC4-R, and more preferably, at least a 100 fold greater affinity or avidity, and more preferably, at least a 1000 fold greater affinity or avidity and even more preferably, at least a 10,000 fold greater affinity or avidity as compared to binding of the same compound to an MC4-R. A POMC compound useful for body weight loss or decrease in weight gain (including prevention of weight gain, or maintenance of weight) preferably induces or increases the activity of an MC2-R and/or an MC5-R at least about 10 fold more as compared to the activity of an MC4-R contacted with the same compound, and preferably, at least about 100 fold more, and more preferably, at least about 1000 fold more, and even more preferably, at least about 10,000 fold more as compared to the activity of an MC4-R contacted with the same compound.

In a preferred embodiment, the POMC compound can include any peptide that has an amino acid sequence which includes the amino acid sequence represented herein by SEQ ID NO:1 (EHFRW), or a homologue or mimetic thereof, which, when administered in an effective manner to a patient, has the ability to measurably regulate body weight in such patient. Peptides which have an amino acid sequence that includes SEQ ID NO:1 preferably also have one or more of the identifying characteristics of a POMC compound as described above.

In another embodiment, a preferred POMC compound includes, but is not limited to, a melanocortin and/or a lipocortin, fragments of such peptides, homologues of such peptides, mimetics (peptide or non-peptide) of such peptides, fusion proteins comprising such peptides, and any pharmaceutical salts of such peptides. Melanocortins include, but are not limited to: adrenocorticotrophin (ACTH), α-melanocyte stimulating hormone (α-MSH), β-melanocyte stimulating hormone (β-MSH) and γ-melanocyte stimulating hormone (γ-MSH); and β-endorphin. Preferred melanocortins include melanocyte stimulating hormones (MSH), fragments of such peptides, homologues of such peptides, mimetics (peptide or non-peptide) of such peptides, fusion proteins comprising such peptides, and any pharmaceutical salts of such peptides. Particularly preferred MSH peptides include α-MSH, β-MSH and γ-MSH, fragments of such peptides, homologues of such peptides, mimetics (peptide or non-peptide) of such peptides, fusion proteins comprising such peptides, and any pharmaceutical salts of such peptides.

The nucleic acid and amino acid sequences for the naturally occurring POMC peptides in a large variety of animals (i.e., human, mouse, rat, rabbit, bovine, ovine, macaque, amphibian, etc.) are known in the art. Such sequences can be found, for example, in a protein or nucleic acid database such as GenBank. GenBank accession numbers for such POMC peptide (i.e., amino acid) sequences include, but are not limited to: Accession Nos. NP_000930 or CAA24754 (*Homo sapiens*); Accession No. P06297 (rabbit); Accession No. P01194 (rat); Accession No. P01193 (mouse); Accession No. P01191 (sheep); Accession No. P01190 (bovine); and Accession No. CTMKP (pig-tailed macaque). GenBank accession numbers for such POMC nucleic acid sequences include, but are not limited to: Accession No. NM_000939 (*Homo sapiens*); Accession No. AH005319 (mouse); Accession Nos. J00016, J00019, J00021 (bovine); Accession No. S73519 (swine); S57982 (ovine); and Accession No. AH002232 (rat).

The amino acid sequence of human α-MSH is:

Ac-Ser-Tyr-Ser-Met-Glu-His-Phe-Arg-Trp-Gly-Lys-Pro-Val-NH$_2$;

and is represented herein by SEQ ID NO:2. It should be noted that since amino acid sequencing and nucleic acid sequencing technologies are not entirely error-free, any sequences presented or referenced herein, at best, represent apparent sequences of POMC peptides, homologues, peptide mimetics, and nucleic acid sequences encoding such peptides, useful in the present invention.

As discussed above, particularly preferred POMC compounds for use in decreasing body weight according to the present invention are homologues or mimetics of POMC peptides, also referred to herein collectively as analogs of POMC peptides, which have enhanced properties as compared to the naturally occurring POMC peptide, such properties including: (1) enhanced ability to bind to a POMC peptide receptor, and particularly, to a POMC receptor that is expressed in peripheral (as opposed to central nervous system) tissues; (2) enhanced serum half-life (i.e., enhanced stability under physiological conditions); and/or (3) enhanced ability to stimulate lipolysis and/or to inhibit the uptake of fatty acids by adipocytes. Particularly preferred POMC antagonists for use in increasing body weight according to the present invention are antagonistic homologues or mimetics of POMC peptides, also referred to herein collectively as antagonist analogs of POMC peptides, which have antagonistic properties to the naturally occurring POMC peptides, such properties including: (1) ability to bind to a POMC peptide receptor that is expressed in peripheral (as opposed to central nervous system) tissues, and particularly, to block the binding of a naturally occurring POMC peptide to the receptor and/or to deliver a negative signal to the POMC receptor; (2) enhanced serum half-life (i.e., enhanced stability under physiological conditions); and/or (3) decreased ability to stimulate lipolysis and/or to inhibit the uptake of fatty acids by adipocytes or an ability to inhibit lipolysis and/or to stimulate the uptake of fatty acids by adipocytes.

As used herein, the term "homologue" is used to refer to a peptide which differs from a naturally occurring peptide (i.e., the "prototype") by minor modifications to the naturally occurring peptide, but which maintains the basic peptide and side chain structure of the naturally occurring form. Such changes include, but are not limited to: changes in one or a few amino acid side chains; changes in one or a few amino acids, including deletions (e.g., a truncated version of the peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. Preferably, a homologue has either enhanced or substantially similar properties compared to the naturally occurring POMC peptide as discussed above (i.e., agonists), although peptides with diminished properties (i.e., antagonists) are also encompassed by certain embodiments of the present invention. Preferred fragments include any truncated or internal fragment of a naturally occurring POMC peptide which may or may not be additionally modified as described herein for homologues and/or mimetics. In one embodiment, a preferred POMC fragment is a fragment of MSH, and more preferably, an MSH fragment including amino acid positions 4-9, 4-10 or 4-11 of naturally occurring MSH. Such fragments, including analogs of such fragments, are discussed in detail below. In one embodiment, a homologue of a POMC peptide comprises an amino acid sequence comprising at least about 4, and more preferably at least about 8 and more preferably at least about 16 contiguous amino acid residues of an amino acid sequence of a naturally occurring (i.e., wild-type) POMC peptide. In another embodiment, a POMC peptide homologue is encoded by a nucleic acid sequence comprising at least about 12, and more preferably at least about 24, and even more preferably at least about 48 contiguous nucleotides of a nucleic acid sequence encoding a naturally occurring POMC peptide.

POMC homologues can be the result of natural allelic variation or natural mutation. A naturally occurring allelic variant of a nucleic acid encoding POMC peptide (or a protein comprising a POMC peptide) is a gene that occurs at essentially the same locus (or loci) in the genome as the gene which encodes such POMC peptide, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

As used herein, the term "mimetic" is used to refer to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example.

Such mimetics can be designed, selected and/or otherwise identified using a variety of methods known in the art. Various methods of drug design, useful to design mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety. A POMC mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

Preferred POMC analogs (homologues or mimetics) for use in the method of the present invention include POMC analogs of the melanocortins. Particularly preferred POMC analogs for use in the method of the present invention include analogs of MSH proteins (peptides). Numerous analogs (homologues and mimetics) of POMC peptides, and particularly, of melanocortins, have been previously described in the art, and all are intended to be encompassed for use in the method of the present invention. For example, such analogs are disclosed in Hadley et al., 1986, "α-Melanotropin analogs for Biomedical Applications", *Neural and Endocrine Peptides and Receptors*, T. W. Moody, ed., Plenum Publ. Corp., NY, pp. 45-56; U.S. Pat. No. 4,649,191 to Hruby, U.S. Pat. No. 4,918,055 to Hruby et al., U.S. Pat. No. 5,674,839 to Hruby et al., U.S. Pat. No. 5,683,981 to Hadley et al., U.S. Pat. No. 5,714,576 to Hruby et al., and U.S. Pat. No. 5,731,408 to Hruby et al., each of which is incorporated herein by reference in its entirety, particularly with regard to the structures of analogs of melanocortins and especially, MSH analogs, disclosed therein, as well as to the methods of producing such analogs. An MSH analog suitable for use in the method of the present invention is exemplified in Examples 2-5 (i.e., [Ac-$Cys^4$, D-$Phe^7$, $Cys^{10}$] α-MSH, with the Cys residues being joined by a disulfide bond), although it will be apparent to those of skill in the art that the present invention is not limited to this particular MSH analog.

Preferred MSH analogs include, but are not limited to, the following analogs:

(a) cyclic and linear α-MSH fragment analogs of the core sequence of α-MSH, $Met^4$-$Glu^5$-$His^6$-$Phe^7$-$Arg^8$-$Trp^9$-$Gly^{10}$ (positions 4-10 of SEQ ID NO:2), having modifications including but not limited to: (1) replacement of Met$^4$ with Nle; (2) replacement of L-Phe$^7$ with D-Phe$^7$; (3) cyclization between positions 4 and 10; and/or (4) presence of Lys$^{11}$ in analog at position 10 (See U.S. Pat. Nos. 5,674,839 and 5,714,576 to Hruby et al., supra);

(b) linear and cyclic analogs of α-MSH having the general formula: Ac-[Nle$^4$, X$_{aa}^5$, His$^6$, X$_{aa}^7$, Arg$^7$, Trp$^9$, X$_{aa}^{10}$]-NH$_2$ (SEQ ID NO:3)

wherein X$_{aa}^5$ is either Glu or Asp, X$_{aa}^7$ is Phe or D-Phe and X$_{aa}^{10}$ is a dibasic amino acid, lysine, ornithine, 2,4,-diaminobutyric acid, or 2,3 diaminopropionic acid (Dpr); and, wherein cyclization is between positions 4 and 10 (See U.S. Pat. Nos. 5,674,839 and 5,714,576 to Hruby et al., supra);

(c) cyclic analogs of α-MSH using pseudoisosteric replacement of Met$^4$ and Gly$^{10}$ with Cys amino acids Ac-[Cys$^4$, Cys$^{10}$]α-MSH$_{1-13}$NH$_2$ (See U.S. Pat. Nos. 5,674,839 and 5,714,576 to Hruby et al., supra);

(d) linear analogs of the formula: R$_1$-W-X-Y-Z-R$_2$ (See U.S. Pat. No. 4,918,055 to Hruby et al., supra); wherein R$_1$ is selected from the group consisting of Ac-Gly-, Ac-Met-Glu-, Ac-Nle-Glu- and Ac-Tyr-Glu-;

W is selected from the group consisting of -His- and -D-His-;

X is selected from the group consisting of -Phe-, -D-Phe-, -Tyr, -D-Tyr-, (-pNO$_2$)D-Phe$^7$-;

Y is selected from the group consisting of -Arg- and -D-Arg-;

Z is selected from the group consisting of -Trp- and -D-Trp-; and,

R$_2$ is selected from the group consisting of —NH$_2$, -Gly-NH$_2$, and -Gly-Lys-NH$_2$;

(e) linear α-MSH analogs having the formula: Ac-Ser-Tyr-Ser-M-Glu-His-D-Phe-Arg-Trp-Gly-Lys-Pro-Val-NH$_2$ (SEQ ID NO:4), wherein M is selected from the group consisting of Met, Nle, and Cys (See U.S. Pat. No. 4,918,055 to Hruby et al., supra);

(f) linear α-MSH analogs selected from the group consisting of:
[Nle$^4$, D-Phe$^7$]-α-MSH;
[Nle$^4$, D-Phe$^7$]-α-MSH$_{4-10}$;
[Nle$^4$, D-Phe$^7$]-α-MSH$_{4-11}$;
[Nle$^4$, D-Phe$^7$, D-Trp$^9$]-α-MSH$_{4-11}$; and,
[Nle$^4$, D-Phe$^7$]-α-MSH$_{4-9}$(See U.S. Pat. No. 4,918,055 to Hruby et al., supra); and, (g) cyclic bridged analogs of α-MSH having the general structure (See U.S. Pat. No. 5,683,981 to Hadley et al., supra)

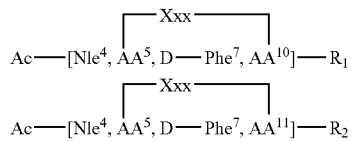

wherein AA$^5$ may be either a L- or D-amino acid having an omega amino or carboxyl group in the side chain, e.g., α,γ-diaminopropionic acid, α,γ-diaminobutyric acid, Orn, Lys, α,β-aminoadipic acid, α-aminopimelic acid, or higher homologs, Glu or Asp;

wherein AA$^{10}$ may be diaminopropionic acid, α,γ-diaminobutyric acid, Orn, Lys, α,β-aminoadipic acid, α-aminopimelic acid, or higher homologs, Glu or Asp;

wherein R$_1$ is the designation α-MSH$_{1-13}$NH$_2$, α-MSH$_{1-12}$NH$_2$, α-MSH$_{1-11}$NH$_2$, α-MSH$_{4-13}$NH$_2$, or α-MSH$_{4-10}$NH$_2$;

wherein AA$^{11}$ may be L- or D-amino acid having an omega-amino or carboxyl group in the side chain, e.g., α,β-diaminopropionic acid; α,γ-diaminobutyric acid, Orn, Lys, α-aminoadipic acid, α-aminopimelic acid, or higher homologs, Glu or Asp;

wherein R$_2$ is the designation α-MSH$_{1-13}$NH$_2$, α-MSH$_{1-12}$NH$_2$, α-MSH$_{1-11}$NH$_2$, α-MSH$_{4-13}$NH$_2$, or α-MSH$_{4-10}$NH$_2$; and, wherein Xxx may be from 1 to 5 α-amino acid residues each of which may be of L- or D-configuration, or a linear or branched chain spacer.

MSH analogs which may be particularly useful as α-MSH antagonists (See U.S. Pat. No. 4,649,191 to Hruby et al., supra) include, but are not limited to:

(a) cyclic analogs having the general formula (See U.S. Pat. No. 5,731,408 to Hadley et al., supra)

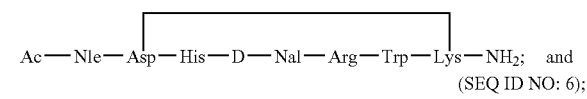

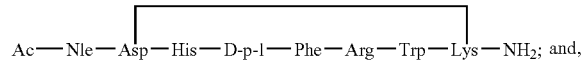

(b) cyclic analogs having the general formula (See U.S. Pat. No. 4,649,191 to Hruby et al., supra):

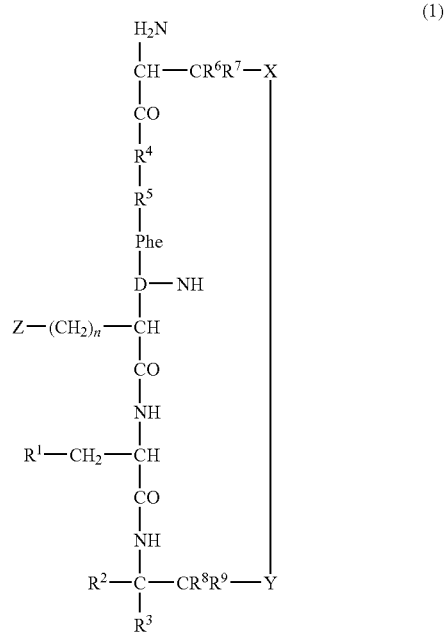

wherein R$^1$ is a substituted or unsubstituted aromatic radical;

R$^2$ is hydrogen or a methyl group;

R$^3$ is a carboxylate, carboxamide, hydroxymethyl, or aldehyde group;

R$^4$ is glutamic acid, alanine, -amino butyric acid, valine, leucine or isoleucine;

R$^5$ is histidine, glutamic acid, alanine, valine, leucine or isoleucine;

$R^6$ and $R^7$, which may be the same or different, are hydrogen, methyl or lower alkyl having one to five carbon atoms;
$R^8$ and $R^9$, which may be the same or different, are hydrogen, methyl or lower alkyl having one to five carbon atoms;
X and Y are sulfur, methylene, SO or $SO_2$;
Z is —$NH_2$,

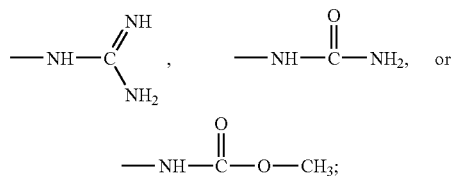

and,
n is an integer greater than or equal to 2;

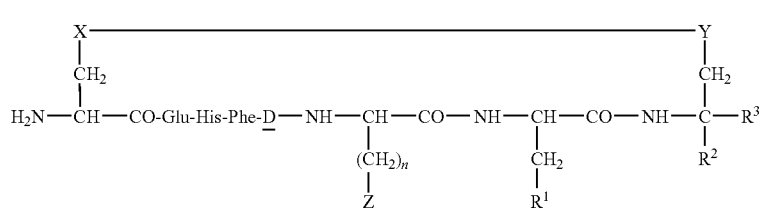

wherein $R^1$ is phenyl, indole, p-hydroxyphenyl, p-aminophenyl, imidazole, 1-naphthyl adamantyl or alkylphenyl, 2-naphthyl;
$R^2$ is hydrogen or a methyl group;
$R^3$ is a carboxylate, carboxamide, hydroxymethyl, or aldehyde group;
X and Y are sulfur, methylene, SO or $SO_2$;
Z is —$NH_2$,

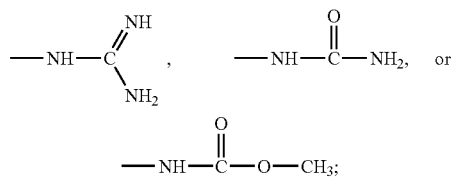

and,
n is an integer greater than or equal to 2; and wherein the cyclized portion of the compound is conformationally restricted in a manner which is compatible with the reactivity of the compound with receptors of the central nervous system.

In one embodiment of the present invention, POMC homologues and mimetics have increased or decreased stability and/or increased or decreased biological activity compared to an unmodified POMC peptide (i.e., a naturally occurring or prototype POMC peptide).

As used herein, the biological activity or biological action of a protein (e.g., a peptide) refers to any function(s) exhibited or performed by a naturally occurring form of the protein as measured or observed in vivo (i.e., in the natural physiological environment of the protein in the organism) or in vitro (i.e., under laboratory conditions, in tissue culture or cell free systems, for example). For example, a biological activity of a protein can include, but is not limited to, hormone activity, protein binding activity, receptor binding activity, calcium binding activity, protein translocation, or DNA binding activity. Modifications of a protein, such as in a homologue or mimetic, which result in a decrease in protein expression or a decrease in the activity of the protein, can be referred to as inactivation (complete or partial), down-regulation, or decreased action of a protein. Similarly, modifications which result in an increase in protein expression or an increase in the activity of the protein, can be referred to as amplification, overproduction, activation, enhancement, up-regulation or increased action of a protein.

In accordance with the present invention, increased stability refers to the property of a POMC homologue or mimetic to have a longer half-life (i.e., have greater stability under physiological conditions, such as in serum), by being more resistant, for example, to proteolytic degradation compared to proteins comprising unmodified POMC peptides, to higher or lower temperature, to more acidic or basic pH, to higher or lower salt concentrations, to oxidation and/or reduction, to deamidation, and to other forms of chemical or biological degradation. Similarly, decreased stability refers to the property of a mimetic to be less resistant, for example, to such conditions.

According to the present invention, an isolated or biologically pure protein, including peptides and analogs thereof, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis. Such methods are described in detail below. It is to be noted that the term "Via" or "an" entity refers to one or more of that entity; for example, a compound refers to one or more compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds.

It will be particularly appreciated by one of skill in the art that by recognizing the benefits of using POMC peptides to regulate body weight in animals, compounds having similar structural characteristics as the POMC peptides of the present invention (e.g., homologues, peptide mimetics and/or non-peptide mimetics) will also be apparent and are intended to be within the scope of the present invention. In other words, one of ordinary skill in the art, without undue experimentation, once they appreciate the role of POMC peptides, and particularly MSH, in the regulation of body weight, are able to isolate and/or synthesize various related compounds and mimetics having the desired, and preferably, improved therapeutic effect as achieved using the particular embodiments of the compounds described herein.

Another POMC compound useful in the method of the present invention includes a fusion protein that includes at least one POMC peptide (or a homologue or peptide mimetic thereof) attached to one or more fusion segments. Suitable fusion segments for use with the present invention include, but are not limited to, segments that can: enhance a protein's stability; act as an enhancer or inhibitor of the biological activity of a POMC peptide; and/or assist with the purification of a POMC peptide (e.g., by affinity chromatography). A suitable fusion segment can be a domain of any size that has the desired function (e.g., imparts increased stability, imparts increased biological activity to a protein, and/or simplifies purification of a protein). Fusion segments can be joined to amino and/or carboxyl termini of the POMC peptide and can also be susceptible to cleavage in order to facilitate recovery of an isolated protein comprising a POMC peptide. Fusion proteins are preferably produced by culturing a recombinant cell transformed with a fusion nucleic acid molecule that encodes a protein including the fusion segment attached to either the carboxyl and/or amino terminal end of a protein comprising a POMC peptide. Preferred fusion segments include a metal binding domain (e.g., a poly-histidine segment); an immunoglobulin binding domain (e.g., Protein A; Protein G; T cell, B cell, or Fc receptor; or complement protein antibody-binding domains); a sugar binding domain (e.g., a maltose binding domain); and/or a "tag" domain (e.g., at least a portion of β-galactosidase, a strep tag peptide, other domains that can be purified using compounds that bind to the domain, such as monoclonal antibodies).

The fusion protein can be used directly in the method of the present invention, or the desired peptide can be isolated for use in the method of the present invention by enzymatic or chemical cleavage. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Ch. 13 in *Protein Purification: from Molecular Mechanisms to Large Scale Processes*, American Chemical Society, Washington, D.C. (1990).

In one embodiment of the present invention, a POMC compound suitable for use in the method of the present invention includes an isolated nucleic acid molecule encoding a POMC peptide, peptide analog thereof, or fusion protein comprising such a peptide, each of which has been described in detail above. Preferably, such an isolated nucleic acid molecule is in the form of a recombinant nucleic acid molecule or as "naked DNA", both of which are described in detail below.

The compounds useful for carrying out the present invention may be produced by any method suitable for the production of peptides and/or non-peptide mimetics, and particularly, for POMC peptides or non-peptide mimetics. For example, such methods include well known chemical procedures, such as solution or solid-phase peptide synthesis, or semi-synthesis in solution beginning with protein fragments coupled through conventional solution methods. Such methods are well known in the art and may be found in general texts and articles in the area such as: Merrifield, 1997, *Methods Enzymol.* 289:3-13; Wade et al., 1993, *Australas Biotechnol.* 3(6):332-336; Wong et al., 1991, *Experientia* 47(11-12): 1123-1129; Carey et al., 1991, *Ciba Found Symp.* 158:187-203; Plaue et al., 1990, *Biologicals* 18(3):147-157; Bodanszky, 1985, *Int. J. Pept. Protein Res.* 25(5):449-474; or H. Dugas and C. Penney, BIOORGANIC CHEMISTRY, (1981) at pages 54-92, all of which are incorporated herein by reference in their entirety. For example, peptides may be synthesized by solid-phase methodology utilizing a commercially available peptide synthesizer and synthesis cycles supplied by the manufacturer. One skilled in the art recognizes that the solid phase synthesis could also be accomplished using the FMOC strategy and a TFA/scavenger cleavage mixture. Methods for synthesizing MSH analogs, for example, are described in detail in U.S. Pat. No. 4,649,191 to Hruby, supra, U.S. Pat. No. 4,918,055 to Hruby et al., supra, U.S. Pat. No. 5,674,839 to Hruby et al., supra, U.S. Pat. No. 5,683,981 to Hadley et al., supra, U.S. Pat. No. 5,714,576 to Hruby et al., supra, and U.S. Pat. No. 5,731,408 to Hruby et al., supra, all of which are incorporated herein by reference in their entirety.

If larger quantities of a POMC peptide are desired, the peptide (or a peptide analog thereof) can be produced using recombinant DNA technology, although for proteins of this small size (i.e., peptides), peptide synthesis is generally preferred. A peptide can be produced recombinantly by culturing a cell capable of expressing the peptide (i.e., by expressing a recombinant nucleic acid molecule encoding the peptide) under conditions effective to produce the peptide, and recovering the peptide. Such techniques are well known in the art and are described, for example, in Sambrook et al., 1988, Molecular Cloning: A Laboratory Manual, Cold Spring Harbor Press, Cold Spring Harbor Laboratory, Cold Spring Harbor, N.Y. or Current Protocols in Molecular Biology (1989) and supplements.

An isolated nucleic acid molecule encoding a POMC peptide or peptide analog thereof (i.e., a homologue or peptide mimetic) can be isolated from its natural source or produced using recombinant DNA technology (e.g., polymerase chain reaction (PCR) amplification, cloning) or chemical synthesis. Methods for producing synthetic nucleic acid molecules are well known in the art. For example, since the POMC peptides are relatively small peptides, the DNA sequence coding for the desired protein may be generated using conventional, commercially available DNA synthesizing apparatus. Alternatively, DNA encoding the desired protein may also be created by using polymerase chain reaction (PCR) techniques or other cloning techniques from genomic DNA of many species. The template also can be a cDNA library or mRNA isolated from central nervous system or pituitary tissue. Such methodologies are well known in the art (Sambrook et al., supra).

Isolated nucleic acid molecules encoding POMC peptides or peptide analogs thereof can be modified from the nucleic acid molecule encoding the prototype peptide by nucleotide insertions, deletions, and substitutions (e.g., nucleic acid homologues) in a manner such that the modifications do not substantially interfere with the nucleic acid molecule's ability to encode a POMC peptide, homologue or mimetic that is useful in the present invention. For example, it may desirable in some applications to modify the coding sequence of the desired protein so as to incorporate a convenient protease sensitive cleavage site, e.g., between the signal peptide and the structural protein facilitating the controlled excision of the signal peptide from the fusion protein construct.

An isolated nucleic acid molecule encoding a POMC peptide can include degeneracies. As used herein, nucleotide degeneracies refers to the phenomenon that one amino acid can be encoded by different nucleotide codons. Thus, the nucleic acid sequence of a nucleic acid molecule that encodes a POMC peptide of the present invention can vary due to degeneracies.

One embodiment of the present invention includes a recombinant nucleic acid molecule, which includes at least one isolated nucleic acid molecule encoding a peptide as described above, inserted into any suitable vector capable of delivering the nucleic acid molecule into a host cell to form a recombinant cell and/or capable of allowing expression of the protein encoded by the nucleic acid molecule. Such a vector typically contains heterologous nucleic acid sequences, that is, nucleic acid sequences that are not naturally found adjacent to nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of POMC peptide-encoding nucleic acid molecules of the present invention.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. As used herein, the phrase "recombinant molecule" primarily refers to a nucleic acid molecule or nucleic acid sequence operatively linked to a transcription control sequence, but can be used interchangeably with the phrase "nucleic acid molecule". It will be appreciated that a double stranded DNA which encodes a given amino acid sequence comprises a single strand DNA and a complementary strand having a sequence that is a complement to the single strand DNA. As such, nucleic acid molecules which encode a POMC peptide of the present invention can be either double-stranded or single-stranded, and include those nucleic acid molecules that encode any of the POMC peptides (including homologues and peptide mimetics) as described herein and as are known in the art.

In order to express the desired peptide, the isolated nucleic acid molecule is operatively linked to one or more transcription control sequences. According to the present invention, the phrase "operatively linked" refers to linking a nucleic acid molecule to a transcription control sequence in a manner such that the molecule is able to be expressed when transfected (i.e., transformed, transduced or transfected) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells useful for expressing a POMC peptide of the present invention. A variety of such transcription control sequences are known to those skilled in the art. Preferred transcription control sequences include those which function in bacterial, yeast, insect or mammalian cells.

Recombinant molecules can also contain additional regulatory sequences, such as translation regulatory sequences, origins of replication, and other regulatory sequences that are compatible with a recombinant cell (i.e., a cell that has been transfected with the recombinant nucleic acid molecule). In one embodiment, a recombinant molecule of the present invention also contains secretory signals (i.e., signal segment nucleic acid sequences) to enable an expressed POMC peptide to be secreted from a cell that produces the protein. Suitable signal segments include a signal segment that is naturally associated with a POMC peptide according to the present invention or any heterologous signal segment capable of directing the secretion of a POMC peptide as is desired according to the present invention. In another embodiment, a recombinant molecule of the present invention comprises a leader sequence to enable an expressed POMC peptide to be delivered to and inserted into the membrane of a host cell. Suitable leader sequences include a leader sequence that is naturally associated with a POMC peptide of the present invention, or any heterologous leader sequence capable of directing the delivery and insertion of a POMC peptide to the membrane of a cell.

Another type of recombinant vector, referred to herein as a recombinant virus, includes a recombinant nucleic acid molecule encoding a POMC peptide or analog thereof that is packaged in a viral coat and that can be expressed in a cell after delivery of the virus to the cell. A number of recombinant virus particles can be used, including, but not limited to, those based on alphaviruses, poxviruses, adenoviruses, herpesviruses, and retroviruses.

Another type of recombinant nucleic acid molecule encompassed by the present invention is a naked nucleic acid molecule, which preferably includes a recombinant molecule as described above that preferably is replication, or otherwise amplification, competent. A naked nucleic acid reagent of the present invention can comprise one or more nucleic acid molecule of the present invention in the form of, for example, a dicistronic recombinant molecule. Preferred naked nucleic acid molecules include at least a portion of a viral genome (i.e., a viral vector).

One or more recombinant molecules of the present invention can be used to produce an encoded product (i.e., a POMC peptide or analog or fusion protein thereof) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include any bacterial, yeast, insect or mammalian cell that can be transfected. Host cells can be either untransfected cells or cells that are already transformed with at least one nucleic acid molecule.

In accordance with the present invention, recombinant cells can be used to produce POMC peptides (including analogs and fusion proteins thereof) by culturing such cells under conditions effective to produce such a protein, and to recover the protein. Effective conditions to produce a protein include, but are not limited to, appropriate media, bioreactor, temperature, pH and oxygen conditions that permit protein production. An appropriate medium refers to any medium in which a cell of the present invention, when cultured, is capable of producing POMC peptides. An effective medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant proteins may either remain within the recombinant cell; be secreted into the culture medium; be secreted into a space between two cellular membranes, such as the periplasmic space in *E. coli*; or be retained on the outer surface of a cell or viral membrane. The phrase "recovering the protein" refers simply to collecting the whole culture medium containing the protein and need not imply additional steps of separation or purification. POMC peptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

In another embodiment of the present invention, a POMC peptide can be expressed by a recombinant nucleic acid molecule or virus encoding the peptide at a desired site in vivo. In this embodiment, a recombinant nucleic acid molecule or virus encoding a POMC peptide, can be administered to an animal as a means of gene therapy. Such a method is particularly useful for animals which have obesity problems related to a POMC-peptide deficiency, although such a method can be used for any patient wherein regulation of body weight is desired. The use of gene therapy vehicles has generally been described in the art (See for example, U.S. Pat. No. 5,593,972, issued Jan. 14, 1997, to Weiner et al.; U.S. Pat. No. 5,580,859, issued Dec. 3, 1996, to Felgner et al.; U.S. Pat. No. 5,589,466, issued Dec. 31, 1996, to Felgner et al.; U.S. Pat. No. 5,641,662, issued Jun. 24, 1997, to Debs et al. and U.S. Pat. No. 5,676,954, issued Oct. 14, 1997, to Brigham, all of which are incorporated herein by reference in their entirety). Such publications have disclosed gene therapy protocols which include administration of nucleic acid molecules (e.g., DNA) encoding any of a variety of other proteins, which are administered to an animal by a variety of administration routes, and using a variety of delivery mechanisms. Preferred methods for delivery of nucleic acid molecules to a patient are discussed in more detail below.

While the present invention, in one embodiment, is directed to the use of POMC compounds alone, it can also be used in combination with other agents, and particularly other body weight regulating agents, including, but not limited to, leptin. Indeed, the present inventors provide evidence herein that the combination of leptin and MSH is has a synergistic effect in treatment of obesity. As used herein, the term "leptin" refers to the protein produced from the obesity (ob) gene following transcription and deletion of introns, translation to a protein and processing to the mature protein with secretory signal peptide, removed, e.g., from the N-terminal valine-proline to the C-terminal cysteine of the mature protein. The amino acid sequences of the mouse obesity protein and human obesity protein are published in Zhang et al., supra. The amino acid sequence of the rat obesity protein is published in Murakami et al., *Biochemical and Biophysical Research Comm* 209(3): 944-52 (1995), incorporated herein by reference in its entirety. Leptin and leptin mimetics are described in detail in U.S. Pat. No. 5,756,461, which is incorporated herein by reference in its entirety. In one embodiment of the invention, leptin is administered in combination with apolipoprotein J (ApoJ). U.S. Pat. No. 5,830,450 to Lallone, incorporated herein by reference in its entirety, describes the use of ApoJ bound to leptin in a composition for the diagnosis and treatment of obesity.

In the embodiment wherein an increase in body weight is desired, while the POMC antagonist compounds can be used alone, they can also be used in combination with other agents, and particularly other body weight regulating agents, including, but not limited to, anabolic steroids, growth hormone, erythropoietin, cytokines, and anti-cytokine agents.

The method of the present invention is useful for treating any animal for the purposes of regulating body weight, including decreasing body weight and/or reducing the rate of weight gain, or increasing body weight and/or decreasing the rate of weight loss. In one embodiment, the method of the present invention is particularly useful for treating obesity. As used herein, the terms "obese" and "obesity" are used to refer to a condition in which an animal (typically human) has a body mass index (BMI) of greater than 27 kilograms per square meter. The phrase, "to treat obesity" in a patient refers to reducing, ameliorating or preventing obesity in a patient that suffers from obesity or is at risk of becoming obese. Therefore, in one embodiment of the present invention, "to treat" a disorder such as obesity can also mean "to prevent" the disorder in a patient. Preferably, the disorder (e.g., obesity), or the potential for developing the disorder, is reduced, optimally, to an extent that the patient no longer suffers from or does not develop the disorder (e.g., excessive accumulation of fat stores in adipose tissue), or the discomfort and/or altered functions and detrimental conditions associated with such disorder. More particularly, "to control" or "to regulate" body weight, or specifically "to treat obesity", includes the administration of POMC compounds as disclosed herein to prevent the onset of the symptoms or complications of undesired body weight, to alleviate the symptoms or complications, or to eliminate the disorder. Treating obese patients, for example, may include but is not limited to, lowering body weight and/or decreasing the rate of weight gain. Individuals having a BMI equal to or less than 27 kilograms per square meter, while not considered to be obese according to the present invention, can also be treated using the method of the present invention to reduce body weight, for example, for cosmetic purposes, athletic training purposes, or for health-associated purposes. The present invention is also useful for treating individuals (e.g., patients) with a percent body fat greater than 20%, and preferably, greater than about 25%, and more preferably, greater than about 30%, and even more preferably, greater than about 35%, 40%, and 45%, in increasing preference. It is to be noted that certain individuals, such as certain athletes, can actually have a BMI greater than 27 kilograms per square meter, while having a relatively low or healthy percent body fat, and therefore, one of skill in the art will appreciate that such individuals may not actually be considered to be obese. Additionally, the present invention is useful for treating patients having undesirable low body weight by administration of POMC antagonists. The method of the present invention relates to protocols for modifying the action of the central and/or peripheral, melanocortinergic and/or leptinergic pathways of energy homeostasis, and particularly, the peripheral pathways.

The methods disclosed herein can also be used in conjunction with other methods related to the treatment of excess body weight or related conditions, including, but not limited to, coadministration of another body weight regulating compound (e.g., leptin), exercise, diet, or liposuction (for example, post-operative or post-dietetic administration of a therapeutic composition of the present invention could be used to reduce the reoccurrence of weight gain, to generally reduce adipose tissue in areas of the patient's body which were not treated or to attempt to reset the metabolic "set point" for weight regulation).

In another embodiment, the method of the present invention is useful for treating any animal for the purposes of increasing body weight and/or mass and/or decreasing the rate of weight and/or mass loss. In particular, this embodiment of the method of the present invention is useful for treating any animal that has a wasting syndrome or other undesirable loss in body weight and/or body mass including, but not limited to, wasting disease, cachexia or sarcopenia. The phrase, "to treat" a condition such as cachexia in a patient refers to reducing, ameliorating or preventing the condition in a patient that suffers from the condition or is at risk of acquiring the condition. Therefore, in one embodiment of the present invention, "to treat" a disorder can also mean "to prevent" the disorder in a patient. Preferably, the condition, or the potential for developing the condition, is reduced, optimally, to an extent that the patient no longer suffers from the condition or begins to accumulate fat stores in adipose tissue and/or body cell mass, or to decrease the discomfort and/or altered functions and detrimental conditions associated with the loss of fat stores and body cell mass. More particularly, "to treat" a condition associated with undesired weight and/or mass loss includes the administration of POMC antagonist compounds as disclosed herein to prevent the onset of the symptoms or complications of such a condition, to alleviate the symptoms or complications, or to eliminate the condition. Treating patients suffering from undesired weight and/or mass loss, such as cachexia, for example, may include but is not limited to, increasing body weight and/or mass and/or decreasing the rate of weight and/or mass gain. The method of the present invention relates to protocols for modifying the action of the central and/or peripheral, melanocortinergic and/or leptinergic pathways of energy homeostasis, and particularly, the peripheral pathways.

The methods disclosed herein can also be used in conjunction with other methods related to the treatment of undesired body weight and/or mass loss or related conditions, including, but not limited to, coadministration of another body weight regulating compound (e.g., anabolic steroids, growth hormone, erythropoietin, cytokines, and anti-cytokine agents) and diet.

In a preferred embodiment, the present invention provides a method for treating patients having low MSH and/or leptin levels, although patients with high endogenous leptin and or MSH levels may also benefit from the present methods. Methods for assaying serum and plasma leptin and MSH levels may be accomplished using standard antibody-based methodologies. Leptin assay kits are also commercially available from Linco Research, Inc. (14 Research Park Dr., St Louis, Mo. 63304). MSH assay antibodies are commercially available from ICN BioMedicals, Inc. and MSH assay kits are commercially available from IBL (Hamburg, Germany). Serum MSH levels typically average about 0.15 ng/ml in humans and are about 10 fold higher in other animals, such as mice (average 2 ng/ml). Treating patients having MSH levels between 0 and 10 ng/ml is preferred. More highly preferred is to treat patients having MSH levels between 0 and 1 ng/ml. Most preferred is to treat patients having MSH levels between 0 and 0.1 ng/ml. More preferred is to treat patients having leptin levels between 0 and 50 ng/ml. More highly preferred is to treat patients having leptin levels between 0 and 30 ng/ml. Most preferred is to treat patients having leptin levels between 0 and 15 ng/ml. Preferably, a patient to be treated has a mass to mass ratio of serum MSH to serum leptin of greater than 1:100 prior to the step of administration. In one embodiment of the present invention, the method includes administering to a patient in whom body weight regulation is desired a composition comprising both a POMC compound according to the present invention and leptin, wherein the ratio of MSH to leptin to be administered is effective to regulate body weight in the patient. Preferably, the ratio of MSH to leptin in the composition is about 1:100, and more preferably, about 1:25 and even more preferably, about 1:10.

In the practice of the present invention, it is useful, although not essential, to prepare therapeutic compositions (i.e., pharmaceutical formulations) comprising an effective amount of at least one POMC compound according to the present invention, either alone or in combination with one or more other body weight regulating formulations or compounds as previously described herein (i.e., leptin). Such compositions, preferably in the form of a pharmaceutically acceptable salt and/or complexed with another suitable pharmaceutically acceptable carrier (described below), can be formulated for any route of administration, including, but not limited to, parenteral administration and transdermal administration. In one embodiment, the therapeutic composition comprises an agent which further minimizes delivery of the POMC compound to the central nervous system, such an agent including, but not limited to an antagonist of MC4-R, an agent that inhibits the binding of a POMC peptide to MC4-R (e.g., an antibody against MC4-R or a competitive inhibitor for MC4-R binding), and/or an agent that inhibits the POMC compound from entering the central nervous system (e.g., by preventing the compound from crossing the blood-brain barrier).

According to the present invention, to "minimize" delivery of a POMC compound to the central nervous system or to minimize effects of the methods of the present invention on the central nervous system, means that biological activities which result from the action of a POMC compound on a receptor and/or cell in the central nervous system are intentionally (preferentially) reduced, inhibited, blocked, decreased, mitigated, or avoided as compared to the biological activities which result from the action of the POMC compound on the peripheral receptors and cells. Various means by which such minimization is accomplished are discussed in detail herein, and include, but are not limited to, peripheral routes of administration (no direct administration to the central nervous system), selection of doses which are insufficient to have a significant effect on central receptor biological activity and/or appetite in the animal, selection of POMC compounds which preferentially bind to and/or activate peripheral receptors as compared to central receptors.

In a preferred embodiment of the present invention, a therapeutic composition comprising a POMC compound, alone or in combination with one or more additional body weight regulating compounds, is formulated to be administered in a manner which extends the time the composition remains in the bloodstream of an animal. As such, a therapeutic composition of the present invention typically includes a pharmaceutically acceptable carrier, and preferably, one which is capable of delivering the composition of the present invention to the peripheral circulation of the animal, and in some cases, is capable of prolonging the action of the composition in the bloodstream of the animal.

For example, therapeutic compositions (i.e., formulations) of the present invention can be formulated in an excipient that the animal to be treated can tolerate. In one embodiment, such an excipient is suitable for use in a composition which is to be administered for delivery to the peripheral circulation. Examples of such excipients include water, saline, phosphate buffered solutions, Ringer's solution, dextrose solution, Harik's solution, polyethylene glycol-containing physiologically balanced salt solutions, and other aqueous, physiologically balanced, salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability or buffers. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

The compositions comprising one or more desired compounds typically contain from about 0.1% to 90% by weight of the active compound, preferably in a soluble form, and more preferably, from about 0.1% to about 50%, and more preferably from about 0.1% to about 25%, and even more preferably, from about 0.1% to about 10%, and even more preferably, from about 0.1% to 1.0%.

In one embodiment of the present invention, a pharmaceutically acceptable carrier can include additional compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

In one embodiment of the present invention, a therapeutic composition can include a controlled release composition that is capable of slowly releasing the formulation into a patient. As used herein, a controlled release composition comprises a POMC compound as described herein in a controlled release vehicle. Suitable controlled release vehicles include, but are not limited to, biocompatible polymers, polymeric matrices, capsules, microcapsules, microparticles, bolus preparations, osmotic pumps, diffusion devices, liposomes, liposheres, and transdermal delivery systems. Other controlled release compositions of the present invention include liquids that, upon administration to an animal, form a solid or a gel in situ. Preferred controlled release compositions are biodegradable (i.e., bioerodible).

One embodiment of the present invention relates to a transdermal patch for delivering the therapeutic composition of the present invention. Such a patch can include additional compounds for enhancing the delivery (i.e., transfer) of components across the epidermal surface of the skin and into the peripheral circulation (e.g., DMSO).

A preferred controlled release composition of the present invention is capable of releasing a formulation of the present invention into the blood of an animal at a constant rate sufficient to maintain therapeutic levels of the formulation to control body weight over a period of time ranging from days to months based on toxicity parameters. A controlled release formulation of the present invention is capable of effecting control over body weight for preferably at least about 6 hours, more preferably at least about 24 hours, and even more preferably for at least about 7 days.

According to the present invention, an effective administration protocol (i.e., administering a POMC compound or a therapeutic composition comprising such a compound in an effective manner) comprises suitable dose parameters and modes of administration that result in regulation of body weight in the animal when administered one or more times over a suitable time period. In one embodiment, an effective administration protocol results in a measurable regulation of body weight and/or body mass of an animal within at least about 2 weeks after the first administration of POMC compound, and more preferably, within at least one week, and more preferably, within at least 3 days, and even more preferably, within at least 24 hours of the first administration of a POMC compound.

Effective dose parameters can be determined using methods standard in the art for a particular animal and condition. Such methods include, for example, determination of survival rates, side effects (i.e., toxicity) and other health factors associated with, or in addition to the amount of body weight loss or gain desired in the animal. In particular, the effectiveness of dose parameters of a therapeutic composition of the present invention when used to control body weight can be determined by assessing response rates. Such response rates refer to the percentage of treated patients in a population of patients that respond with either partial or complete loss of excess weight, or a reduction in the rate of weight gain, or alternatively, to a partial or complete gain of lost weight or a reduction in the rate of weight loss, as compared to a previous, healthy or normal weight and/or mass for the patient prior to the onset of the disorder or as compared to a population normalized healthy or normal weight and/or mass, to a level which is considered by those of skill in the art to be sufficient to address the needs of the particular patient and/or not present health risks to the patient. Response can be determined by, for example, measuring weight loss over time and/or measuring changes in levels of hormones and other biological indicators of obesity and metabolic control in the animal, for example, leptin.

In one embodiment, a response can be evaluated by determining whether the animal's leptin and/or MSH levels in serum are more similar to a "normal population control" than prior to the treatment. As discussed elsewhere herein, an average human serum MSH level is about 0.15 ng/ml, with lower levels being indicative of a metabolic dysfunction which may lead to weight gain. An average serum leptin level for humans is about 10 ng/ml, with higher levels being indicative of a metabolic dysfunction and/or obesity. In a patient who may have a metabolic dysfunction, the levels of MSH may be lower than normal and/or the levels of leptin may be higher than normal, resulting in a change in the ratio of MSH to leptin. Therefore, as another means of comparison, a "normal human" ratio of MSH to leptin is typically about 1:100 (mass to mass), whereas variations in this ratio may indicate a metabolic dysfunction (e.g., an increase in the ratio of MSH to leptin to 1:500 may indicate a propensity for weight gain). In one embodiment of the present invention, a POMC peptide is administered to an animal in an amount effective to restore the ratio of MSH to leptin to about normal levels (e.g., nearer to MSH:leptin=1:100).

Modes of administration of a therapeutic composition of the present invention include any method of administration which results in delivery of the composition to the peripheral circulation of the animal. According to the present invention, the phrase "peripheral administration" or "peripheral delivery" refers to any route of administration which delivers a composition of the present invention to the peripheral circulation, cells and/or tissues of an animal. Peripheral administration is distinguished from routes of administration which are specifically intended to deliver a composition directly to the central nervous system (e.g., by direct injection into the brain or other central nervous system tissues), although it is to be understood that a peripheral route of administration may result in some composition reaching the cells and tissues of the central nervous system. Such modes of administration can include, but are not limited to, oral, nasal, topical, transdermal, rectal, and parenteral routes, as well as direct injection into a tissue and delivery by a catheter. Parenteral routes can include, but are not limited to subcutaneous, intradermal, intravenous, intraperitoneal and intramuscular routes. In one embodiment, the route of administration is by topical or transdermal administration, such as by a lotion, cream, a patch, an injection, an implanted device (e.g., similar to Norplant), or other controlled release carrier. Preferred routes of administration include transdermal delivery and delivery via an implanted device or other controlled release carrier. Particularly preferred routes of administration include any route which directly delivers the composition to the systemic circulation (e.g., by injection), including any parenteral route. It is noted that one of skill in the art will be able to use the guidance provided herein regarding route of administration, pharmaceutical carriers or excipients, and dosage, to select an administration protocol which delivers the composition of the present invention to the peripheral circulation, as opposed to, for example, merely delivering the composition to the dermal tissue as has been previously described for MSH for the use in the treatment of dermal conditions (e.g., vitaligo or dermatitis). Although topical and transdermal delivery of MSH and analogs thereof has been described prior to the present invention (e.g., U.S. Pat. No. 4,874,744 to Nordlund or U.S. Pat. No. 4,649,191 to Hruby et al.), such methods were directed to the treatment of conditions at the dermis, and therefore these methods taught dosage protocols, carriers and administration methods which were suitable for delivering MSH to the dermis for action at the skin, but failed to describe doses, carriers and/or administration methods that are suitable for delivery of MSH to the peripheral circulation, which is where the method of the present invention acts. For example, these methods typically suggested concentration ranges for MSH (e.g., $10^{-10}$, $10^{-11}$) which are well below the level which would be expected to provide a significant effect in the method of the present invention.

In the embodiment where the POMC compound is to be delivered to a patient in the form of a nucleic acid molecule encoding a POMC peptide or peptide analog thereof, the nucleic acid molecules can be delivered to a patient by a variety of methods including, but not limited to, (a) administering a naked (i.e., not packaged in a viral coat or cellular membrane) nucleic acid molecule (e.g., as naked DNA or RNA molecules, such as is taught, for example in Wolff et al., 1990, Science 247, 1465-1468); (b) administering a nucleic acid molecule packaged as a recombinant virus, in a liposome delivery vehicle, or in a recombinant cell (i.e., the nucleic acid molecule is delivered by a viral or cellular vehicle); or (c) administering a recombinant nucleic acid molecule encapsulated within a liposome delivery vehicle.

Naked nucleic acid molecules can be administered in a variety of ways, with intramuscular, subcutaneous, intradermal, transdermal, intranasal and oral routes of administration being preferred. A preferred single dose of a naked nucleic acid molecule ranges from about 1 nanogram (ng) to about 100 µg, depending on the route of administration and/or method of delivery, as can be determined by those skilled in the art. Suitable delivery methods include, for example, by injection, as drops, aerosolized and/or topically. Naked DNA can be contained in an aqueous excipient (e.g., phosphate buffered saline) alone or a carrier (e.g., lipid-based vehicles).

Suitable liposomes for use with the present invention include any liposome. Preferred liposomes of the present invention include those liposomes commonly used in, for example, gene delivery or protein delivery methods known to those of skill in the art, including, but not limited to, multilamellar vesicle (MLV) lipids, extruded lipids and small unilamellar vesicle (SUV) lipids.

Complexing a liposome with a nucleic acid molecule encoding a POMC peptide compound of the present invention can be achieved using methods standard in the art (See, for example, U.S. Pat. No. 5,593,972, issued Jan. 14, 1997, to Weiner et al.; U.S. Pat. No. 5,580,859, issued Dec. 3, 1996, to Felgner et al.; U.S. Pat. No. 5,589,466, issued Dec. 31, 1996, to Feigner et al.; U.S. Pat. No. 5,641,662, issued Jun. 24, 1997, to Debs et al. and U.S. Pat. No. 5,676,954, issued Oct. 14, 1997, to Brigham, all of which are incorporated herein by reference in their entirety.) A suitable concentration of a nucleic acid molecule encoding a POMC peptide compound of the present invention to add to a liposome includes a concentration effective for delivering a sufficient amount of nucleic acid molecule into a mammal such that the POMC peptide compound can be expressed and have the desired biological effect. Preferably, the ratio of nucleic acids to lipids (µg nucleic acid:nmol lipids) in a composition of the present invention is preferably from about 6:1 to about 1:1 nucleic acid:lipid by weight; and more preferably, from about 6:1 to 1:10. Complexing a POMC peptide or analog thereof with a liposome is similarly achieved using methods standard in the art.

An appropriate single dose of a nucleic acid:liposome complex of the present invention is from about 0.1 µg to about 100 µg per kg body weight of the mammal to which the complex is being administered. Preferably, an appropriate single dose of a nucleic acid:liposome complex of the present invention results in at least about 1 pg of protein expressed per mg of total tissue protein per µg of nucleic acid delivered. More preferably, an appropriate single dose of a nucleic acid: liposome complex of the present invention is a dose which results in at least about 10 pg of protein expressed per mg of total tissue protein per µg of nucleic acid delivered; and even more preferably, at least about 50 pg of protein expressed per mg of total tissue protein per µg of nucleic acid delivered; and most preferably, at least about 100 pg of protein expressed per mg of total tissue protein per µg of nucleic acid delivered.

In accordance with the present invention, a suitable or effective single dose size is a dose that is capable of causing a measurable change in the body weight (e.g., a decrease in body weight) of a patient when administered one or more times over a suitable time period. A suitable or effective single dose size can also be a dose that is capable of causing a measurable change in the rate of weight gain or loss in a patient as compared to the rate established prior to initiation of the treatment, when administered one or more times over a suitable time period. In addition, a suitable or effective single dose size is a dose that is capable of preventing or effecting a measurable improvement in a condition in the patient that is associated with or caused by undesirable (e.g., medically unhealthy) body weight. Such a condition includes, but is not limited to, cachexia, non-insulin dependent diabetes mellitus, cardiovascular disease, cancer, hypertension, osteoarthritis, stroke, respiratory problems, reproductive dysfunction, mood disorders, heart problems, sarcopenia, wasting disease and/or gall bladder disease. According to the present invention, and as described previously herein, to regulate body weight can be any measurable decrease or increase in any factor related to body weight, including, but not limited to actual body weight and/or size and changes in hormone levels or other biological indicators related to weight and metabolic control which indicate a change in body weight control, and particularly in hormone levels or other biological indicators related to central and/or peripheral melanocortinergic and/or leptinergic pathways of energy homeostasis. Doses can vary depending upon the condition of the patient being treated, including the apparent cause of the body weight problem and/or any other related or non-related health factors experienced by a particular patient. In general, a patient who has greater excess body weight relative to another patient, may actually require a smaller dose of a POMC compound to obtain an effect from the treatment. In one embodiment of the present invention, formulations derived from POMC compounds are utilized to either increase or decrease adipose tissue in a nonobese or relatively normal individual (e.g., for cosmetic purposes). This can be accomplished by modifying the normal fat metabolism of an individual through the administration of suitable amounts of modified forms of the present composition (e.g., POMC homologues, mimetics, etc.).

One embodiment of the method of the present invention comprises administering a POMC compound, and particularly, a POMC homologue or mimetic, in a dose, concentration and for a time sufficient to effect a measurable change in the body weight or mass of a patient. Such a compound is administered in a dose between a minimum amount sufficient to reach the systemic circulation in the patient and to obtain a measurable effect on body weight or mass in a patient, a dose which minimizes delivery to the central nervous system, and a maximum amount which is effective to obtain a measurable effect on body weight or mass in a patient without inducing deleterious effects (e.g., unmanageable toxicity) in the patient. More particularly, the method of the present invention comprises administering a POMC compound, and particularly, a POMC homologue or mimetic, in a dose between about 0.1 µg and about 100 mg per kilogram body weight of the patient, and preferably, between about 0.1 µg and about 10 mg per kilogram body weight of the patient, and more preferably, between about 0.1 µg and about 1 µg per kilogram body weight of the patient, and even more preferably, between about 1 µg and about 10 mg per kilogram body weight of the patient. A more preferred single dose is from about 40 µg to about 1 mg per kilogram body weight of the patient. A typical daily dose for an adult human (i.e., a 75 kg human) is from about 1 milligram to about 100 milligrams. A preferred circulating level of a POMC compound to achieve in a patient regardless of the route of administration is from about 0.1 µg per kilogram body weight to about 10 µg per kilogram body weight, and more preferably, from about 0.1 µg per kilogram body weight to about 1 µg per kilogram body weight of the patient. In practicing this method, the POMC compound or therapeutic composition containing the compound can be administered in a single daily dose or in multiple doses per day. This treatment method may require administration over extended periods of time. The amount per administered dose or the total amount administered will be determined by the physician and will depend on such factors as the mass of the patient, the age and general health of the patient and the tolerance of the patient to the compound. As discussed above, the molar concentration of a melanocortin agonist that would be necessary to effect a transient decrease in food intake (i.e., via the central nervous system and the melanocortin 4-receptor) is one hundred-fold higher than that required to accomplish weight reduction via peripheral mechanisms (lipolysis and fatty acid uptake). The above doses are believed to sufficient to affect the peripheral metabolic efficiency (i.e., peripheral energy homeostasis) while minimizing effects on the central nervous system and particularly, appetite.

One embodiment of the present invention relates to a method to treat a patient who is unable to gain or retain weight. Such a method includes the step of administering to the periphery of a patient a POMC compound, and preferably, a homologue or mimetic of a POMC peptide, such compound having reduced biological activity as compared to the naturally occurring POMC peptide (i.e., prototype) upon which the homologue or mimetic is based. Such a compound, also referred to herein as a POMC peptide antagonist, is effective to increase the body weight of the patient by a mechanism which can include: blocking the action of the endogenous peptide, for example by binding to and blocking the receptor for the endogenous peptide; or by stimulating free fatty acid uptake and/or inhibiting lipolysis. Other aspects of such a method, including compound preparation and administration are as described for other POMC compounds described previously herein.

Yet another embodiment of the present invention relates to a method to selectively increase or decrease adipose tissue in a specific portion of the body of a patient, comprising introducing to said animal by localized and/or targeted delivery a therapeutic composition of the present invention. Other aspects of such a method, including compound preparation and administration are as described for other POMC compounds described previously herein.

Another embodiment of the present invention relates to a method for inhibition of free fatty acid uptake and/or stimulation of lipolysis in an animal, comprising administering to the periphery of an animal a POMC compound in an amount effective to produce a result selected from the group consisting of stimulation of lipolysis and inhibition of fatty acid uptake. Various aspects of such a method, including compound preparation and administration are as described for other POMC compounds described previously herein. Inhibition of free fatty acid uptake and/or stimulation of lipolysis can be measured by methods known in the art. Preferably, free fatty acid uptake is measurably inhibited as compared to the level of free fatty acid uptake prior to administration of the compound and lipolysis is measurably stimulated as compared to the level of lipolysis prior to administration of the compound. Preferably, the amount of POMC compound administered is insufficient to cause a statistically significant change in the appetite of the animal after administration of the compound as compared to before administration of the compound.

Yet another embodiment of the present invention relates to a method of regulating the body weight of an animal, comprising administering to an animal a POMC compound in an amount effective to bind to POMC receptors expressed by the animal in the animal's peripheral tissues. The effective amount is defined as: (a) being insufficient to substantially change the appetite of the animal after the step of administering as compared to before the step of administering; (b) being between about 0.1 µg and about 10 mg per kg of body weight of the animal; (c) being sufficient to affect a biological activity selected from the group consisting of: (i) lipolysis; and, (ii) uptake of fatty acids by adipocytes in the animal; and, (d) being effective to measurably increase or decrease the body weight of the animal after the compound has been administered to the animal. Aspects of such a method, including compound preparation and administration are as described for other POMC compounds described previously herein.

Another embodiment of the present invention relates to a method to regulate body weight in an animal, comprising modulating the activity of a melanocortin receptor selected from the group consisting of melanocortin 2-receptor and melanocortin 5-receptor. Preferably, the melanocortin receptor is melanocortin 2-receptor. In one embodiment, the step of modulating includes, but is not limited to, administering to the periphery of the animal a compound which regulates the melanocortin receptor. The compound can include, but is not limited to, a POMC compound, an antibody that selectively binds to the melanocortin receptor, and a soluble melanocortin receptor. In another aspect, the step of modulating comprises administering an effective amount of a compound that increases expression of the melanocortin 2-receptor and induces weight loss. In another aspect, the step of modulating comprises administering an effective amount of a compound that decreases expression of the melanocortin 2-receptor and induces weight gain. Aspects of such a method, including various types of receptor agonists and antagonists and compound preparation and administration are as described previously herein.

Yet another embodiment of the present invention relates to a method for regulating metabolic efficiency in an animal, comprising: (a) measuring serum MSH levels in an animal; (b) identifying animals having serum MSH levels of less than about 0.1 ng/ml; and, (c) administering to the periphery of the animals identified in (b) a composition comprising a compound selected from the group consisting of a POMC compound and leptin. Preferably, the compound is administered in an amount effective to increase serum MSH levels in the animal to level effective to produce a result selected from the group consisting of stimulating lipolysis and inhibiting fatty acid uptake in the animal. In one embodiment, the compound is administered in an amount effective to produce a measurable decrease in body weight of the animal. In a preferred embodiment, the compound is administered in an amount effective to increase serum MSH levels to those established for a normal population of patients, which for humans, in one embodiment, is about 0.15 ng/ml or higher.

Another embodiment of the present invention relates to a therapeutic composition useful in any of the above-described or below-described embodiments of the method of the present invention. A therapeutic composition of the present invention comprises one or more therapeutic compounds, including at least one POMC compound as described herein, formulated with a pharmaceutically acceptable carrier. In a preferred embodiment, a therapeutic composition of the present invention includes at least one POMC compound and at least one other body weight regulating compound. In one embodiment, such another body weight regulating compound can include, but is not limited to, leptin.

Preferably, if the additional body weight regulating agent is leptin, the method of the present invention includes administering a leptin compound, including a leptin homologue or mimetic, in conjunction with a POMC compound, in a dose, concentration and for a time sufficient to effect a measurable change in the body weight or mass of a patient. Such a compound is administered in a dose between a minimum amount sufficient to reach the systemic circulation in the patient and to obtain a measurable effect on body weight or mass in a patient, and a maximum amount which is effective to obtain a measurable effect on body weight or mass in a patient without inducing deleterious effects (e.g., unmanageable toxicity) in the patient. More particularly, the method of the present invention comprises administering a leptin compound in a dose between about 0.1 µg and about 100 mg per kilogram body weight of the patient, and preferably, between about 0.1 µg and about 10 mg per kilogram body weight of the patient, and more preferably, between about 0.1 µg and about 1 µg per kilogram body weight of the patient, and even more preferably, between about 1 µg and about 10 mg per kilogram body weight of the patient. A more preferred single dose is from about 50 µg to about 1 mg per kilogram body weight of the patient. A typical daily dose for an adult human (i.e., a 75 kg human) is from about 0.5 milligram to about 100 milligrams. In practicing this method, the leptin compound or therapeutic composition containing the POMC compound and the leptin compound can be administered in a single daily dose or in multiple doses per day. This treatment method may require administration over extended periods of time. The amount per administered dose or the total amount administered will be determined by the physician and will depend on such factors as the mass of the patient, the age and general health of the patient and the tolerance of the patient to the compound. As discussed above, preferably, the ratio of MSH to leptin in the composition is about 1:100, and more preferably, about 1:25 and even more preferably, about 1:10.

Another embodiment of the present invention relates to a method to identify POMC compounds, and particularly, homologues and mimetics, for use in a method of the present invention. Such a method includes screening a putative POMC compound for its ability to stimulate lipolysis and/or to inhibit fatty acid uptake by adipocytes, and in particular, to control obesity. Such a method can include selecting compounds which preferentially bind to and/or activate peripheral melanocortin receptors as compared to central nervous system melanocortin receptors, and particularly, MC4-R. Such a method can be performed in vitro or in vivo (e.g., in vivo experiments can be performed using the POMC mutant mouse model of obesity of the present invention, and the compounds identified by such a method can be used in the method to treat obesity according to the present invention).

It is noted that melanocortin receptor genes and proteins, and in vitro assays for determining melanocortin receptor activity are known in the art. For example, U.S. Pat. Nos. 5,703,220 and 5,710,265 to Yamada et al.; U.S. Pat. No. 5,532,347 to Cone et al.; and PCT Publication WO 97/47316 and U.S. Pat. Nos. 5,908,609 and 5,932,779 to Lee et al.; describe known melanocortin receptors and the genes encoding such receptors, including MC2-R, MC4-R and MC-5R, as well as in vitro and in vivo assays for identifying compounds which bind to and/or activate such receptors. Each of these patents and PCT publication is incorporated herein by reference in its entirety, and particularly, with regard to disclosed methods for evaluating the activity of melanocortin receptors and the identification of compounds which bind to such receptors. However, none of the above-referenced patents or PCT publication discloses a method for identifying compounds useful for regulating body weight by identifying compounds which bind to, activate or inhibit activity of peripheral melanocortin receptors, and particularly, which preferentially bind to, activate or inhibit activity over central melanocortin receptors. Prior to the present invention, it was not known that the peripheral melanocortin receptors (and not central melanocortin receptors) and the compounds that bind to such receptors regulate metabolic efficiency. Moreover, the present inventors are the first to disclose an assay for the identification of compounds that preferentially bind to, activate, or inhibit the activity of MC2-R and/or MC5-R as compared to MC4-R, or which bind to, activate, or inhibit the activity of MC2-R and/or MC5-R in the absence of significant MC4-R binding or activation.

According to the present invention, the "activity" or "biological activity" of a melanocortin receptor refers to any function(s) exhibited or performed by a naturally occurring form of the melanocortin receptor as measured or observed in vivo (i.e., in the natural physiological environment of the protein) or in vitro (i.e., under laboratory conditions). For example, a biological activity of a melanocortin receptor can include, but is not limited to, ligand binding activity (e.g., with a melanocortin, such as MSH), interaction with an intracellular signal transduction protein, upregulation of expression of the melanocortin receptor, and induction of biological effects such as lipolysis and/or free fatty acid uptake (for peripheral receptors) and modulation of appetite (in vivo for MC4-R). An increase in melanocortin receptor activity can be referred to as amplification, overproduction, activation, enhancement, up-regulation or increased action of the receptor, as compared to a normal or baseline control or as compared to the activity of the receptor prior to a given treatment (e.g., contact with a putative regulatory compound). Similarly, a decrease in melanocortin receptor activity can be referred to as inactivation (complete or partial), inhibition, down-regulation, or decreased action of the receptor, as compared to a normal or baseline control or as compared to the activity of the receptor prior to a given treatment (e.g., contact with a putative regulatory compound).

Another embodiment of the present invention relates to a method to treat health-compromising conditions associated with excess body weight, and particularly, obesity. Such conditions include, but are not limited to, non-insulin dependent diabetes mellitus (NIDDM), cardiovascular disease, cancer, hypertension, osteoarthritis, stroke, respiratory problems and gall bladder disease. Such a method includes the step of administering to the periphery of an animal suffering from or at risk for developing an obesity-associated condition, a therapeutic composition comprising a POMC compound which can include POMC peptides or fragments, homologues, peptide mimetics, non-peptide mimetics, fusion proteins or pharmaceutically acceptable salts thereof; or, recombinant nucleic acid molecules encoding such POMC peptides, fragments, homologues, peptide mimetics, or fusion proteins. The POMC compound is administered peripherally in an amount effective measurably decrease body weight or the rate of weight gain, and/or to reduce or prevent the deleterious symptoms of the health-compromising condition. The POMC compound of the present invention can be administered with or without one or more additional compounds, including other body weight regulating compounds, such as leptin. Various aspects of such a method, including compounds, administration protocols, and desired effects, have been previously described herein.

As used herein, the an obesity-associated disorder is any disease or condition that is caused by or associated with (e.g., by biochemical or molecular association) obesity or that is caused by or associated with weight gain and/or related biological processes that precede clinical obesity. The phrase, "to treat" a disorder associated with obesity in a patient refers to reducing, ameliorating or preventing the disorder in a patient that suffers from the disorder or is at risk of acquiring the disorder. Therefore, in one embodiment of the present invention, "to treat" a disorder associated with obesity can also mean "to prevent" the disorder in a patient. Preferably, the disorder, or the potential for developing the disorder, is reduced, optimally, to an extent that the patient no longer suffers from or does not develop the disorder or the discomfort and/or altered functions and detrimental conditions associated with such disorder. The method of the present invention includes the administration of POMC compounds as disclosed herein to prevent the onset of the symptoms or complications associated with undesired body weight and the metabolic dysfunction of obesity, to alleviate the symptoms or complications of the obesity-related disorder other than, or in addition to, obesity, or to eliminate the obesity-related disorder. Therefore, treatment of an obesity-associated disorder can also include regulation of body weight for treatment of the obesity itself, which is likely to indirectly concurrently improve the obesity-related disorder.

The method of the present invention, being directed to the treatment of a disorder that is associated with obesity, is intended to be used in conjunction with one or more other treatment protocols that are appropriate for treatment of the given condition. For example, for a patient that has NIDDM, in addition to administering the therapeutic composition of the present invention, the patient may be treated with a regimen of diet and exercise, and in extreme cases, with injections of insulin.

According to the present invention, an effective administration protocol (i.e., administering a POMC compound or a therapeutic composition comprising such a compound in an effective manner) comprises suitable dose parameters and modes of administration that result in a measurable change in one or more symptoms of the condition associated with obesity that is to be treated. For ex ample, a patient with NIDDM, after treatment with a therapeutic composition of the present invention, may experience an increased ability to regulate blood glucose levels, as indicated by an improved score in a standard glucose tolerance test. Preferably, an effective administration protocol comprises suitable dose parameters and modes of administration that also result in the regulation of body weight in the animal when administered one or more times over a suitable time period. Effective dose parameters can be determined using methods standard in the art for a particular animal and condition. Such methods include, for example, determination of survival rates, side effects (i.e., toxicity) and other health factors associated with, or in addition to the amount of body weight loss or gain desired in the animal. In particular, the effectiveness of dose parameters of a therapeutic composition of the present invention when used to control body weight can be determined by assessing response rates. Such response rates refer to the percentage of treated patients in a population of patients that respond with either partial or complete reduction in one or more symptoms of an obesity-associated condition and/or partial or complete loss of excess weight or a reduction in the rate of weight gain, to a level which is considered by those of skill in the art to be sufficient to address the needs of the particular patient and/or not present health risks to the patient. Response can be determined by, for example, measuring weight loss over time and/or measuring changes in levels of hormones and other biological indicators of obesity and the obesity-associated disorder in the animal, for example, leptin.

In a preferred embodiment, a therapeutic composition of the present invention includes at least one POMC compound and at least one other body weight regulating compound. In one embodiment, such another body weight regulating compound can include, but is not limited to, leptin. In another embodiment, a therapeutic composition of the present invention includes at least one POMC compound and at least one other compound that is useful in treating the obesity-associated disorder experienced by a patient. Such an additional compound could include, for example, insulin for an extremely severe case of NIDDM or a beta blocker for a patient with cardiovascular disease.

Another embodiment of the present invention relates to compositions and methods for treating affective and mood disorders in an animal and for treating or preventing health-compromising conditions related thereto, and particularly, to regulate body weight in patients suffering from affective and mood disorders. As used herein, an affective and mood disorder, also referred to as an affective disorder, can be any disorder that is generally characterized by a neuroendocrine dysregulation and a disturbance in the regulation of mood, behavior and affect. Affective disorders can include major depressive disorders, such as depression and dysthymia, which atypical depression and dysthymia being particularly amenable to treatment using the present invention. According to the present invention, "to treat" a disorder such as an affective and mood disorder can also mean "to prevent" the disorder in a patient. Preferably, the disorder, or the potential for developing the disorder, is reduced, optimally, to an extent that the patient no longer suffers from or does not develop the disorder, or the discomfort and/or altered functions and detrimental conditions associated with such disorder (e.g., sleeplessness, lack of energy, excessive accumulation of fat stores in adipose tissue). Such a method includes the step of peripherally administering to the patient a proopiomelanocortin (POMC) compound, which can include a POMC peptide, a fragment thereof, a homologue thereof, a peptide or non-peptide mimetic thereof, a fusion protein including such peptide, a pharmaceutically acceptable salt thereof, or a recombinant nucleic acid molecule encoding such a POMC peptide, fragment, homologue, peptide mimetic, or fusion protein thereof. In a preferred embodiment, the POMC compound is a melanocyte stimulating hormone (MSH) compound. The compound is administered in an amount effective to measurably ameliorate the disorder and/or to measurably regulate body weight in the animal, which minimizing delivery of the compound to the central nervous system. Various aspects of such a method, including compounds, administration protocols, and desired effects, have been previously described herein.

While a majority of the prior art methods to treat affective and mood disorders have involved the use of anti-depressant drugs or other compounds such as leptin (See U.S. Pat. No. 5,866,547, ibid.), which regulate primarily the central nervous system, the present invention is directed to the use of compounds which regulate the peripheral pathways of energy homeostasis to treat affective and mood disorders and conditions related thereto, including dysregulation of body weight. Such a method comprises administering to an animal that is at risk for or has an affective and mood disorder and/or a detrimental condition related thereto a therapeutic composition that primarily regulates the peripheral melanocortinergic pathway and/or the leptinergic pathway of energy homeostasis. The compound and method of the present invention are believed to represent a new approach for the treatment of affective and mood disorders which are expected to have particular advantages for alleviating, eliminating or preventing undesirable symptoms associated with such disorders, such as excess or insufficient body weight.

More particularly, the present invention is derived from the inventors' discovery that administration of a proopiomelanocortin (POMC) peptide agonist to an animal suffering from obesity reduces obesity in the animal, from the present inventors' discovery that MSH and leptin synergize to enhance such a reduction, and from previous research indicating a role for leptin in the treatment of affective and mood disorders (U.S. Pat. No. 5,866,547, ibid.). Included in the present invention is a method for modifying the peripheral melanocortinergic pathways for treating affective and mood disorders (and conditions related thereto) in patients at risk of, or suffering from such disorders, by administering an effective amount of circulating melanocyte stimulating hormone (MSH) or analogs (e.g., homologues or mimetics) thereof, alone or in combination with leptin or other anti-depressant or body weight regulating drugs. In one embodiment of the present invention, POMC compounds, alone or in combination with leptin, are used to enhance the effects of a conventional treatment for affective and mood disorders, such as anti-depressant drugs and psychotherapy.

Affective and mood disorders are characterized by a wide fluctuation of moods, from extreme depression- to elation. Such disorders are typically caused by neuroendocrine dysregulation and can have a deleterious and sometimes, incapacitating, effect on an individual's behavior and the ability of an individual to interact and function in every day life. Examples of such disorders include depression and dysthymia.

One type of depression, referred to herein as atypical depression, is characterized by decreased energy with hypersomnia, hyperphagia, weight gain and mood liability (Licinio et al., 1991, *Bailliere's Clin. Endocrin. Met.* 5(1):51-58. Disregulation of the hypothalamic-pituitary-adrenal (HPA) axis, which regulates physiological responses to stress, is correlated with atypical depression. The hypothalamus releases corticotrophic-releasing hormone (CRH) in response to stress, which in turn stimulates the anterior pituitary to secrete adrenocorticotrophic-releasing hormone (ACTH). ACTH stimulates the adrenal cortex to release cortisol which then signals the hypothalamus to regulate CRH production. In atypical depression, the hypothalamus secretes abnormally low levels of CRH, which in turn causes abnormally low activity in the HPA axis.

Dysthymia is another affective and mood disorder that is characterized by chronic despondency and loss of energy and interest. Additionally, an individual suffering from dysthymia can experience hypophagia or hyperphagia, insomnia or hypersomnia, and lack of ability to concentrate. Dysthymia is often associated with higher than normal CRH levels, resulting in hyperactivity of the HPA axis; however, in individuals that tend to be overweight (i.e., have a higher body mass index (BMI) than normal), the CRH levels in the hypothalamus can be lower in normal.

The association of leptin with both regulation of body weight and with affective disorders suggests that therapeutic strategies including leptin may offer new avenues for the treatment of a variety of disorders involving hypothalamic regulation (or dysregulation). The use of leptin to treat obesity in mice, however, requires very high, non-physiological doses. Thus, leptin alone has not been found to be a particularly useful anti-obesity agent. Similar problems are expected with the use of leptin to treat affective disorders.

Typically, affective and mood disorders are treated with a variety of anti-depressant drugs. Such drugs have not proven to adequately or completely treat the disorders, however, and in some cases, such drugs are lethal when acute overdosage occurs and can cause morbidity even under a physicians supervision. The frequency and severity with which affective and mood disorders occur in the general population emphasize the need for continued development of compounds and treatments to alleviate or prevent some or all of the symptoms associated with such conditions. Therefore, there remains a need in the art for a simple, safe and effective method for the treatment of affective and mood disorders and conditions related to such disorders such as undesirable or health-compromising body weight.

By applying a POMC compound as described herein peripherally, when the naturally occurring form of such compound is normally produced centrally, peripheral effects are stimulated while central nervous system effects can be controlled as desired, depending on the severity of the condition in a particular patient and the desired end result of the treatment. The method of the present invention will prevent patients from relying on psycho-active drugs. For example a depressed patient gaining weight may become dependent on appetite suppressants. The present invention provides a solution to this problem.

In the practice of this embodiment of the present invention, it is useful, although not essential, to prepare therapeutic compositions (i.e., pharmaceutical formulations) comprising an effective amount of at least one POMC compound according to the present invention, either alone or in combination with one or more other anti-depressant and/or body weight regulating formulations or compounds as previously described herein (i.e., leptin). Such compositions, preferably in the form of a pharmaceutically acceptable salt and/or complexed with another suitable carrier (described below), can be formulated for any route of administration, including, but not limited to, parenteral administration and transdermal administration. In a preferred embodiment of the present invention, a therapeutic composition comprising a POMC compound, alone or in combination with one or more additional anti-depressant and/or body weight regulating compounds, is formulated to be administered in a manner which extends the time the composition remains in the bloodstream of an animal. As such, a therapeutic composition of the present invention typically includes a pharmaceutically acceptable carrier, and preferably, one which is capable of delivering the composition of the present invention to the peripheral circulation of the animal, and in some cases, is capable of prolonging the action of the composition in the bloodstream of the animal.

The effectiveness of dose parameters of a therapeutic composition of the present invention when used to control affective and mood disorders can be determined by assessing response rates. Such response rates refer to the percentage of treated patients in a population of patients that respond with either partial or complete improvement in the disorder, in a partial or complete loss of excess weight, or a reduction in the rate of weight gain, or alternatively, to a partial or complete gain of lost weight or a reduction in the rate of weight loss, to a level which is considered by those of skill in the art to be sufficient to address the needs of the particular patient and/or not present health risks to the patient. Response can be determined by, for example, measuring energy, mood, sleeping patterns, and/or weight loss or gain over time and/or measuring changes in levels of hormones and other biological indicators of the disorder in the animal, such as leptin.

Yet another embodiment of the present invention relates to a method to treat a reproductive disorder in an animal. Such a method includes the steps of administering to the periphery of an animal at risk for or suffering from a reproductive disorder a therapeutic composition comprising a POMC compound. The POMC compound is administered in an amount effective to prevent and/or ameliorate the disorder, and/or to measurably regulate body weight in the animal, whereby administration of the compound to the central nervous system of the animal is minimized. Various aspects of such a method, including compounds, administration protocols, and desired effects, have been previously described herein.

In the original report of the ob mutation (Ingalls et al., 1950, *J Hered.* 41:317-318), it was recognized that male and female homozygous ob/ob mice are sterile. Moreover, it was noted that ob/ob females are always sterile, and that ob/ob males can become fertile if maintained on a restricted diet (Lane et al., 1954, *J Hered* 45:56-58). Hummel et al. taught that the ovaries of ob/ob females are capable of producing viable eggs when transplanted into lean female recipients (Hummel et al., 1957, *Anat. Rec.* 128:569). Other research showed that early sexual development is normal in these mice, but ovulation never follows and the mice remain prepuberal indefinitely. FSH, LH and testosterone levels are reduced in ob/ob females (Swerdloff et al., 1976, *Endocrinology* 98:1359-1364), demonstrating the absence of a functional feedback from the hypothalamic-pituitary axis. Hypofunction of the pituitary gland in the female ob/ob mouse was demonstrated by showing that in vivo uterine weights of the mice did not significantly change after bilateral ovariectomy (Runner et al., 1954, *Genetics* 39:990-991; Drasher et al., 1955, *J. Heredity* 46:209-212) but did, however, respond to exogenous estrogen. Pituitary extracts administered to ob/ob females induced ovulation and conception, but no implantation (Runner, 1954, *Rec. Genet. Soc. Am.* 23:63-64) which was achieved following treatment with gonadotropic hormones (Runner et al., 1954, *J. Heredity* 45:51-55) Furthermore, the administration of high doses of progesterone maintained pregnancy for 19 days p.c., but did not enable the mothers to deliver the fetuses except after administration of relaxin which stimulated parturition and lactation (Smithberg et al., 1956, *J. Exp. Zool.* 133:441-458; Smithberg et al., 1957, *J. Heredity* 48:97-100). The above findings demonstrated that the sterility of the ob/ob female is caused by an insufficiency of hormones at the hypothalamic-pituitary level rather than physical hindrance of copulatory activity by excess adipose tissue.

While a majority of the prior art methods to treat reproductive disorders have involved the use of hormones, diet, or other compounds such as leptin (See U.S. Pat. No. 5,866,547, ibid.), which are primarily directed to the regulation the central nervous system, the present invention is directed to the use of compounds which regulate the peripheral pathways of energy homeostasis to treat reproductive disorders and conditions related thereto, including dysregulation of body weight. Such a method comprises administering to an animal that is at risk for or has reproductive dysfunction and/or a detrimental condition related thereto a therapeutic composition that regulates the peripheral melanocortinergic pathway and/or the leptinergic pathway of energy homeostasis. Such a therapeutic composition may also regulate the central melanocortinergic pathway of energy homeostasis. The compound and method of the present invention are believed to represent a new approach for the treatment of reproductive disorders which are expected to have particular advantages for alleviating, eliminating or preventing undesirable symptoms associated with such disorders, such as excess or insufficient body weight.

Without being bound by theory, the present inventors believe that the regulation of other biological activities associated with body weight regulation, including hypothalamic-pituitary-adrenal axis activity suggests that the administration of such peptides and analogs thereof to a patient may affect both body weight regulation and the other biological activities associated therewith (e.g., reproductive function).

As used herein, a reproductive disorder refers to any disorder characterized by hormonal deficiency which negatively affects the initiation of puberty, ovulation, conception, maintenance of pregnancy and/or delivery of offspring, such deficient hormone typically being one or more hypothalamic, pituitary or gonadal hormones. Individuals having a reproductive disorder can include infertile and/or amenorrheic females, and particularly, females incapable of or having a reduced ability to ovulate, conceive, maintain pregnancy, lactate, and/or deliver a full-term offspring. Similarly, male individuals having a reproductive disorder can be characterized by an inability or reduced ability to impregnate females or enter puberty. According to the present invention, "to treat" a disorder such as a reproductive disorder can also mean "to prevent" the disorder in a patient. Preferably, the disorder, or the potential for developing the disorder, is reduced, optimally, to an extent that the patient no longer suffers from or does not develop the disorder (i.e., initiates or accelerates puberty, improves their ability to maintain pregnancy, etc.), or the discomfort and/or altered functions and detrimental conditions associated with such disorder (e.g., inability to ovulate, excessive accumulation of fat stores in adipose tissue, etc.).

In accordance with the present invention, a suitable or effective single dose size is a dose that is capable of causing a measurable change in the symptoms associated with the reproductive disorder (e.g., a decrease in body weight) of a patient when administered one or more times over a suitable time period. A suitable or effective single dose size can also be a dose that is capable of causing a measurable change in the symptom of the reproductive disorder in a patient as compared to the level of the symptom established prior to initiation of the treatment, when administered one or more times over a suitable time period. In addition, a suitable or effective single dose size is a dose that is capable of preventing or effecting a measurable improvement in a condition in the patient that is associated with or caused by the reproductive disorder. Such a condition includes, but is not limited to, ovulation, conception, pregnancy maintenance, lactation, delivery of a full term offspring, onset of menstruation, etc. Doses can vary depending upon the condition of the patient being treated, including the apparent cause of the reproductive disorder and/or any other related or non-related health factors experienced by a particular patient.

In particular, the effectiveness of dose parameters of a therapeutic composition of the present invention when used to control reproductive disorders can be determined by assessing response rates. Such response rates refer to the percentage of treated patients in a population of patients that respond with either partial or complete improvement in the disorder, in a partial or complete loss of excess weight, or a reduction in the rate of weight gain, or alternatively, to a partial or complete gain of lost weight or a reduction in the rate of weight loss, to a level which is considered by those of skill in the art to be sufficient to address the needs of the particular patient and/or not present health risks to the patient. Response can be determined by, for example, onset of menstruation, ability to conceive and/or maintain a pregnancy, and/or weight loss or gain over time and/or measuring changes in levels of hormones and other biological indicators of the disorder in the animal, such as leptin.

In accordance with the present invention, a suitable or effective single dose size is a dose that is capable of causing a measurable change in the symptoms associated with the reproductive disorder (e.g., a decrease in body weight) of a patient when administered one or more times over a suitable time period. A suitable or effective single dose size can also be a dose that is capable of causing a measurable change in the symptom of the reproductive disorder in a patient as compared to the level of the symptom established prior to initiation of the treatment, when administered one or more times over a suitable time period. In addition, a suitable or effective single dose size is a dose that is capable of preventing or effecting a measurable improvement in a condition in the patient that is associated with or caused by the reproductive disorder. Such a condition includes, but is not limited to, ovulation, conception, pregnancy maintenance, lactation, delivery of a full term offspring, onset of menstruation, etc. Doses can vary depending upon the condition of the patient being treated, including the apparent cause of the reproductive disorder and/or any other related or non-related health factors experienced by a particular patient.

In one embodiment of the present invention, POMC compounds, alone or in combination with leptin, are used to enhance the effects of a conventional treatment for reproductive disorders, such as hormone therapy.

Yet another embodiment of the present invention relates to a method and compound for controlling excess or insufficient body weight (i.e., decreasing body weight, reducing weight gain, increasing body weight, or reducing weight loss) that is a side effect of using another pharmaceutical compound. Such a method comprises administering to the periphery of an animal that is at risk for or has undesired body weight due to a side effect of a pharmaceutical compound a therapeutic composition that regulates the peripheral melanocortinergic pathway and/or the leptinergic pathway of energy homeostasis. The composition comprises a POMC compound in an amount effective to measurably decrease body weight or weight gain in said animal, whereby administration of said compound minimizes delivery of said compound to the central nervous system of said animal. Various aspects of such a method, including compounds, administration protocols, and desired effects, have been previously described herein.

In a preferred embodiment, the present invention relates to reducing body weight and/or reducing weight gain in an animal, and more particularly, to treating or ameliorating obesity in patients at risk for or suffering from obesity which is caused as a side effect of using a pharmaceutical. Conditions for which pharmaceuticals are prescribed which can cause undesired body weight include, but are not limited to, epilepsy, attention deficit hyperactivity disorder (ADHD), depression, bipolar disorder, and migraine. Pharmaceuticals (i.e., drugs) which have a well documented side effect of undesired weight gain or loss include, but are not limited to valproic acid (i.e., Depakote), lithium, tricyclic antidepressants (e.g., amitriptyline, nortriptyline or desipramine), and selective serotonin reuptake inhibitors (SSRI) such as fluoxetine (i.e., Prozac).

Yet another embodiment of the present invention relates to a food composition for use with humans or other animals which regulates body weight or the rate of body weight gain or loss. The food composition comprises a proopiomelanocortin (POMC) compound (i.e., the food additive) which can include, but is not limited to: POMC peptides or fragments, homologues, peptide mimetics, non-peptide mimetics, fusion proteins or pharmaceutically acceptable salts thereof. The POMC compound of the present invention can be administered with or without additional compounds, including other body weight regulating compounds, such as leptin, although in the case of compounds such as leptin, the leptin must be protected from the gastrointestinal tract by any suitable means, or be administered by a different route. In a preferred embodiment, the food composition ameliorates obesity in obese animals, but does not significantly diminish weight in normal animals. Therefore, including POMC proteins in foodstuffs is ameliorative to obese individuals who consume such foodstuffs, but does not significantly affect normal individuals who may not have the genetic propensities leading to obese conditions. Various aspects of such a method, including compounds, administration protocols, and desired effects, have been previously described herein.

According to the present invention a food composition useful herein is any food stuff (i.e., consumable, edible material) which can contain a food additive including a POMC compound as described herein, and which is preferably capable of protecting the POMC compound within the gastrointestinal tract and allowing at least a portion of the POMC compound to enter the blood stream. In the practice of the present invention, it is useful, although not essential, to prepare food compositions comprising an effective amount of at least one POMC compound according to the present invention, either alone or in combination with one or more other body weight regulating formulations or compounds as previously described herein (i.e., leptin). Such compositions, preferably in the form of a is pharmaceutically acceptable salt and/or complexed with another suitable carrier (described below), are formulated for use in a food composition (i.e., non-toxic, suitable for use as a food additive). In a preferred embodiment of the present invention, a food composition comprising a POMC compound, alone or in combination with one or more additional body weight regulating compounds, is formulated to protect the compound long enough for the compound to enter the bloodstream, and to extend the time the composition remains in the bloodstream of an animal. As such, a food composition of the present invention typically includes an acceptable carrier, and preferably, one which is capable of protecting the compound in the gastrointestinal tract and/or prolonging the action of the composition in the bloodstream of the animal.

For example, food compositions of the present invention can be formulated in an excipient that the animal to be treated can tolerate. In one embodiment, such an excipient is suitable for use in a composition which is to be administered for delivery to the peripheral circulation. Examples of such excipients include water, saline, phosphate buffered solutions and other aqueous, physiologically balanced, salt solutions. Nonaqueous vehicles, such as fixed oils, sesame oil, ethyl oleate, or triglycerides may also be used.

Yet another embodiment of the present invention relates to a method for increasing body weight and/or mass and/or reducing the rate of weight and/or mass loss in a patient, as a part of a treatment program for eating disorders such as anorexia or bulimia. The method includes the step of administering to an animal a therapeutic composition comprising a proopiomelanocortin (POMC) antagonist compound, wherein the POMC compound is administered to the periphery of the animal in an amount effective to measurably increase body weight or reduce body weight loss in the animal, whereby administration of the compound minimizes delivery of the compound to the central nervous system of the animal. Various aspects of such a method, including compounds, administration protocols, and desired effects, have been previously described herein.

The rise in bulimia and anorexia in the past few decades is alarming, and illustrates the disturbing emphasis on ideal body size and shape regardless of the severe health consequences. The regulation of body weight is a major health concern throughout the world, and particularly in the United States, contributing to morbidity and mortality. For certain individuals, however, regulation of body weight is driven by psychological conditions and an overwhelming desire to be thin. While obesity is a metabolic disorder characterized by excessive accumulation of fat stores in adipose tissue, and is caused by a complex interplay of genetics, environment and culture, eating disorders resulting in unhealthy weight loss are typically psychological problems associated with deeper issues, including depression or lack of self esteem, which drive an individual to participate in unhealthy eating habits. It is well known that a regimen of diet and exercise leading to weight loss is the best approach for reaching a healthy body weight, but unfortunately, such regimens are grossly abused by the individual with an eating disorder.

In addition to the obvious health risks associated with being underweight, the tangential detrimental effects of such conditions are equally troublesome. Conditions related to or affected by low body weight can include heart failure, susceptibility to infectious disease as a result of immune system weakness, and depression. For individuals suffering from an eating disorder, the goal of therapy, in addition to treating the psychological problem, is to increase the body weight of the patient.

The method of the present invention is useful for treating any eating disorder that is characterized by or associated with unhealthy body weight or body mass loss. Such conditions, include, but are not limited to anorexia and bulimia. The present invention is not necessarily intended to be a "cure" for such conditions, but rather, is intended to be used in conjunction with appropriate conventional therapy for eating disorders (e.g., psychotherapy) which addresses the root of the condition itself. More particularly, the present invention relates to a composition and method for increasing body weight which may have certain advantages as discussed below.

The method of the present invention is useful for treating any animal for the purposes of increasing body weight and/or mass and/or decreasing the rate of weight and/or mass loss. In particular, the method of the present invention is useful for treating any animal that has an eating disorder including, but not limited to, anorexia and bulimia. The phrase, "to treat" a condition such as anorexia in a patient refers to reducing, ameliorating or preventing the condition in a patient that suffers from the condition or is at risk of acquiring the condition. Therefore, in one embodiment of the present invention, "to treat" a disorder can also mean "to prevent" the disorder in a patient. Preferably, the condition, or the potential for developing the condition, is reduced, optimally, to an extent that the patient no longer suffers from the condition or begins to accumulate fat stores in adipose tissue and/or body cell mass, or to decrease the discomfort and/or altered functions and detrimental conditions associated with the loss of fat stores and body cell mass. More particularly, "to treat" a condition associated with excessively low weight and/or mass loss includes the administration of POMC antagonist compounds as disclosed herein to prevent the onset of the symptoms or complications of such a condition, to alleviate the symptoms or complications, or to eliminate the condition. In the case of an eating disorder, such treatment is typically only a small portion of an overall therapy which includes a significant amount of psychotherapy.

According to the present invention, an effective administration protocol (i.e., administering a POMC antagonist compound or a therapeutic composition comprising such a compound in an effective manner) comprises suitable dose parameters and modes of administration that result in regulation of body weight and/or mass (i.e., increase in body weight and/or mass or decrease in rate of weight and/or mass loss) in the animal when administered one or more times over a suitable time period. Effective dose parameters can be determined using methods standard in the art for a particular animal and condition. Such methods include, for example, determination of survival rates, side effects (i.e., toxicity) and other health factors associated with, or in addition to the amount of body weight and/or mass gain desired in the animal. In particular, the effectiveness of dose parameters of a therapeutic composition of the present invention when used to control body weight and/or mass can be determined by assessing response rates. Such response rates refer to the percentage of treated patients in a population of patients that respond with either partial or complete gain of lost weight and/or mass (as compared to a previous, healthy or normal weight and/or mass for the patient prior to the onset of the disorder) or a reduction in the rate of weight and/or mass loss, to a level which is considered by those of skill in the art to be sufficient to address the needs of the particular patient and/or not present health risks to the patient. Response can be determined by, for example, measuring weight and/or mass gain over time and/or measuring changes in levels of hormones and other biological indicators of weight loss and metabolic control in the animal, for example, leptin.

Various aspects of the present invention are illustrated in the following examples, which are provided for the purposes of illustration and are not intended to limit the scope of the present invention.

EXAMPLES

Example 1

The following example describes the production of the POMC null mutant mouse of the present invention and demonstrates that POMC peptides are associated with the regulation of body weight through both central and peripheral mechanisms.

To create a mutant mouse strain lacking all proopiomelanocortin (POMC) derived peptides, the present inventors designed a targeting vector in which the entire third exon (Notake et al., 1983, *FEBS Lett* 156:67-71; incorporated herein by reference in its entirety) is replaced by a neomycin resistance cassette. Briefly, EcoRI-digested 129/SvEv genomic DNA was cloned into lambda FixII (Stratagene). The resulting library was screened with a 0.3 kb PCR fragment from exon 3 of the mouse Pomc1 sequence, and a clone carrying a 9.5 kb fragment containing the mouse Pomc1 locus was isolated. For the targeting vector the KnpI-PstI fragment containing the third exon was deleted. This removes all but the first 44 codons for amino acids after the translation start of the pre-pro-protein, or all but the first 18 codons for amino acids of the POMC protein. Targeting vector (20 µg) was used to electroporate $10^7$ RW4 ES cells (Genome Systems). ES cells which homologously integrated the mutated allele were injected into C57BL/6 blastocysts as described (Hogan et al., "Manipulating the Embryo", Cold Spring Harbor Laboratory Press, 1994). Chimeric mice were mated to 129/SvEvTac females. Heterozygous offspring were mated to generate homozygous mutant mice. Genotypes were analyzed by PCR and confirmed by Southern blot analysis as described (Sambrook et al. ibid.).

FIG. 1A shows schematic diagrams and restriction maps of the mouse POMC locus, the targeting vector, and the predicted structure of the POMC locus after homologous recombination. The 0.4 kb probe fragment hybridizes to a 9.5 kb EcoRI fragment in the wildtype allele, and to a 3.2 kb fragment in the mutant allele (see also FIG. 11B). Restriction sites indicated are EcoRI (E), KpnI (K), and PstI (P). FIG. 1B shows Southern blot analyses of tail DNAs from $F_2$ littermates. The probe used was the 0.4 kb PstI-EcoRI fragment (see FIG. 1A). FIG. 1C shows an RIA analysis of serum ACTH levels in $F_2$ male littermates (measurements in triplicates, one mouse per genotype) (discussed in detail below).

The deleted POMC allele construct was introduced into embryonic stem (ES) cells by electroporation and from there into the mouse germline, generating strain Pomc$^{tm2ute}$. When the mutation was backcrossed into the inbred 129/SvEv background, homozygous POMC mutants were born to heterozygous parents at one quarter (39 wildtype, 80 heterozygotes, 10 mutants) of the frequency expected for a recessive mutation, indicating that concurrent lack of all of the embryonic derived POMC peptides is compatible with survival throughout prenatal development in only a fraction of the animals.

Female POMC null mice are fertile and carry heterozygous and wild-type pups to term. When heterozygous POMC males are mated to homozygous POMC mutant females, homozygous mutant, but not heterozygous, offspring die within the first few hours after birth.

Figure 2B:
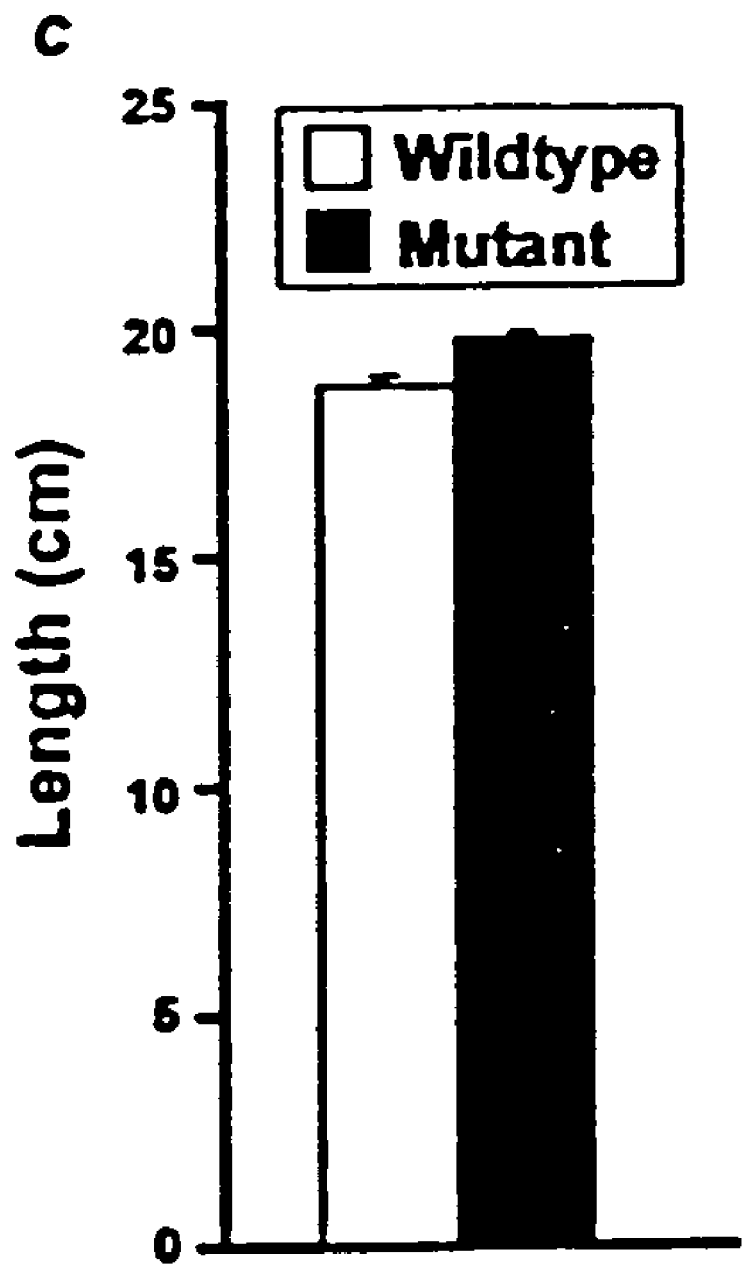
FIG. 2B is a bar graph illustrating that mutant POMC mice show increased linear growth.
Figure 2C:
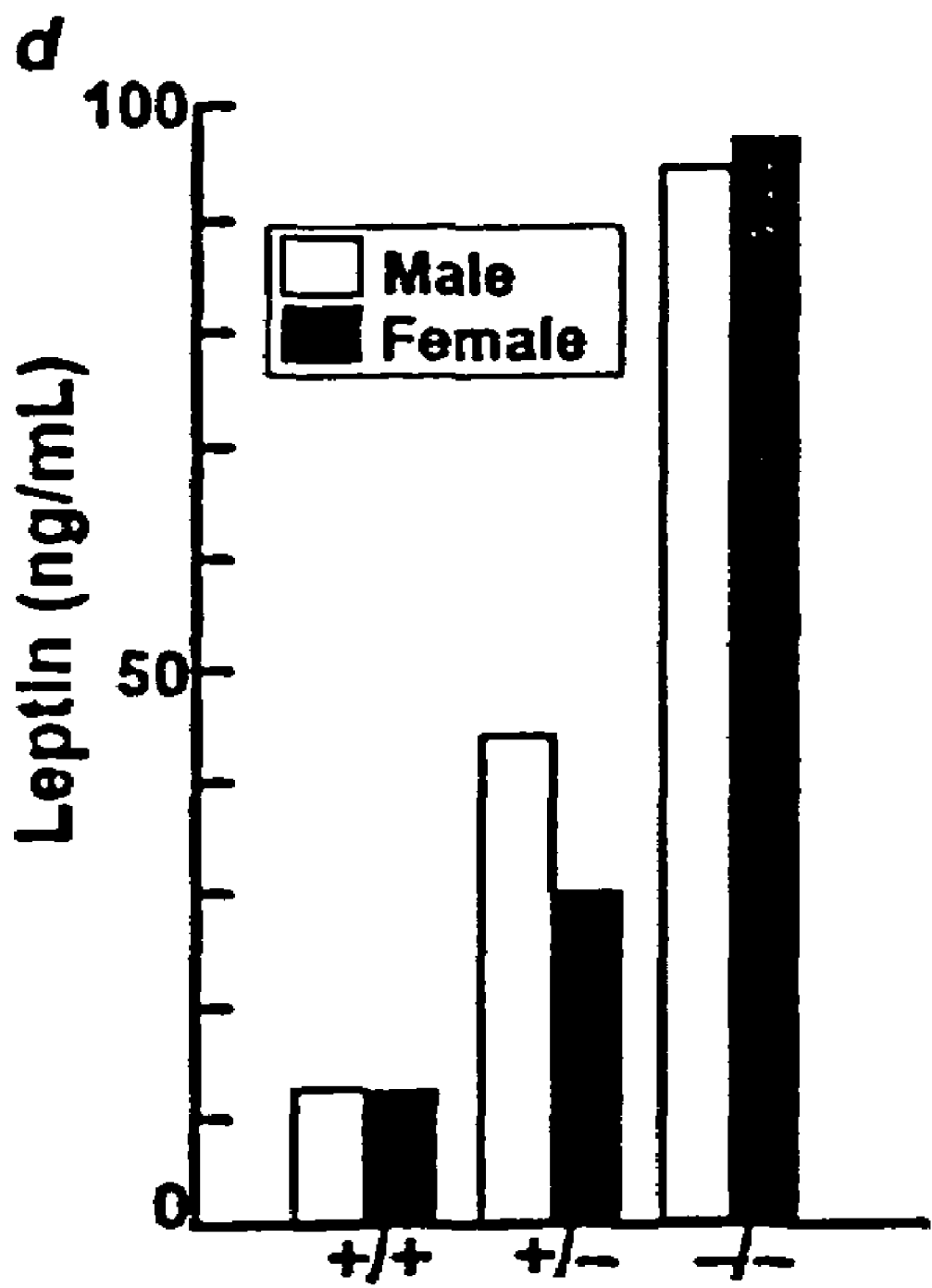
FIG. 2C is a bar graph illustrating that POMC null mice have elevated leptin serum levels.

During the first postnatal month homozygous mutants are superficially indistinguishable from their wildtype littermates. In the second month, mice lacking POMC peptides start to gain weight visibly, and by the third postnatal month their weights are about twice those of their wildtype littermates (FIG. 2A; weight measurements were taken from male mice of each genotype; at 2 months n=4, P<0.0005; at 3 months n=3, P<0.005). The weight gain is accompanied by both a slight, but significant, increase in body length (FIG. 2B; measurements (snout to root of tail) were taken from 3-4 months old female mice, 6 mice per genotype (P<0.001)) and a large increase in serum leptin levels (FIG. 2C). In this latter experiment, serum leptin levels were determined (in duplicates) from blood samples collected retroorbitally from 6-8 months old, individual, male and female mice. Average weights were 30.9 g for wildtype mice, 31.7 g for heterozygotes, and 55.9 g for homozygotes. Interestingly, heterozygote mice show elevated levels of serum leptin, but do not display significantly increased body weight. The elevated leptin levels in the normal weight heterozygotes suggest a homeostatic balance between leptin levels and POMC peptide levels: the decreased POMC peptide levels are compensated by increased leptin. The mechanism and significance of such a relationship suggest a paracrine feed-back loop.

Figure 2D:
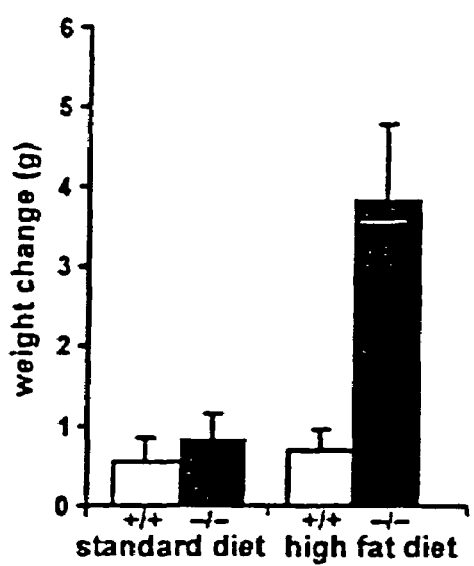
FIG. 2D is a bar graph illustrating weight change for POMC null mice and wildtype mice being fed a standard diet or a high fat diet.
Figure 2E:
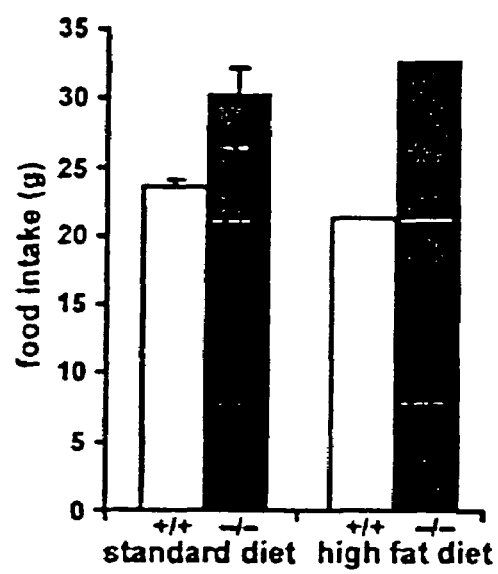
FIG. 2E is a bar graph illustrating food intake for POMC null mice and wildtype mice being fed a standard diet or a high fat diet.

It was also noticed that the POMC mutant mice raised on a high fat breeder chow gained weight faster than mice raised on standard chow. Wildtype and mutant females (3 per test group) were given unlimited access either to standard or to breeder chow (4.5% and 9% fat, respectively). FIGS. 2D and 2E show weight change (2D) and food intake (2E) during one week. Food intake in the "high fat diet" groups was measured in bulk for all three mice. FIG. 2D shows that the mutant mice gained 3 grams more per week on a high fat diet versus a standard diet (3.8 g versus 0.8 g), while wildtype mice gained 0.2 g more on a high fat diet versus a standard diet (0.7 g versus 0.5 g). FIG. 2E shows that the food intake by POMC mutants increased with high fat diet by 2.4 g (30.3 g versus 32.7 g), while the food intake by wildtype littermates decreased with high fat diet by 2.2 g (23.5 g versus 21.3 g). Under either dietary condition mutant mice lacking POMC have an increased food intake compared to wildtype littermates. These results suggest that POMC derived peptides mediate both food intake and bodily food deposit. Wildtype mice regulate their food intake according to the diet, i.e., they decrease intake with a higher caloric supply, and they adjust their metabolism (food deposit versus burning) to keep their body weight constant. In contrast, mice lacking POMC show a deficit in both of these aspects with the result of increased body weight: they have an increased food uptake and they lack the ability to catabolize dietary fat.

Another visible difference between POMC null mutant mice and the wildtype mice is the yellowish pigmentation of mutant mice (data not shown), which is especially pronounced on the belly. MC1-R in melanocytes is normally stimulated by α-MSH, resulting in synthesis of eumelanin (black/brown) pigment (Burchill et al., 1986, *J. Endocrinol.* 109:15-21). Antagonism of MC1-R by the agouti-signaling protein (ASP) overexpressed in $A^y$ mice results in whole body yellow coat color (Lu et al., 1994, *Nature* 371:799-802). A loss-of-function mutation in the Mc1r gene in the recessive yellow mouse (e/e) (Robbins et al., 1993, *Cell* 72:827-834) and in cattle (Joerg et al., 1996, *Mamm. Genome* 7:317-318) causes yellow coat and red coat, respectively. The human patients with POMC null mutations have red hair as well (Krude et al., ibid.). In the POMC null mice, the change in pigmentation is subtle, in that the coat covering the sides and belly is more yellow than in wildtype littermates, and the tips of the hairs at the back have a yellowish tinge. These pigmentation differences in mutants become more pronounced during adulthood. The fact that in the mouse, lack of the ligand (POMC) does not result in a phenotype congruent with lack or antagonism of MC1-R, suggests the presence of other ligands for this melanocortin receptor. Alternatively, this result could be explained if there is a ligand-independent constitutive activity of the receptor.

Next, the effect of a complete lack of ACTH on adrenal function was determined. Serum corticosterone levels (FIG. 3A) were determined by RIA from blood samples collected retroorbitally from 6-7 month old mice (n=7 for wildtypes, n=6 for heterozygotes, n=5 for mutants). Serum aldosterone levels (FIG. 3B) were determined in trunk blood samples from 7-8 month old mice (n=1 for wildtypes, n=2 for heterozygotes, n=3 for mutants). Plasma catecholamine levels (FIGS. 3C-3E) were determined in trunk blood samples from 7-8 month old mice (n=4 for wildtype mice, n=3 for mutant mice).

FIG. 1C shows an RIA analysis of serum ACTH levels in $F_2$ male littermates (measurements in triplicates, one mouse per genotype). Blood was collected retroorbitally and serum was analyzed by RIA following the provider's instructions (ICN, corticosterone; IncStar, ACTH; Linco, Leptin). FIG. 1C shows that ACTH levels in the mutant animal were below the sensitivity of the assay, indicating that the coding region for all POMC peptides had been deleted.

Serum corticosterone and aldosterone levels were below detection (FIGS. 3A and 3B), despite considerable stressing of mice during blood collection, indicating an absolute necessity for POMC derived peptides for adrenal cortical function. Here again, heterozygotes show a gene dosage effect, suggesting fine-tuned regulation by POMC peptides. When plasm catecholamine basal levels were measured (FIGS. 3C-3E), epinephrine was significantly lower in POMC mutants versus wildtype mice (FIG. 3C; p<0.006), while levels of norepinephrine were not significantly altered (FIG. 3D; p<0.27) and dopamine levels were slightly increased in mutants compared to wildtypes (FIG. 3E; p<0.06). In cases of dysfunction of the adrenal medulla, other chromaffine tissues expressing catecholamines increase production to compensate; epinephrine, however, is almost exclusively produced by the adrenal medulla. The significant decrease of epinephrine indicates a severe dysfunction and/or lack of the adrenal medulla in POMC deficient mice. Looking for adrenal glands proved to be impossible: mutant mice had no macroscopically discernible adrenal glands. For histological analysis, tissues from the fat pad surrounding the kidney were collected and immediately placed into formalin. Sectioning (5 µm thickness) and staining were carried out by American Histolab, Inc., Gaithersburg, Md. Histological examination of the fat pad surrounding the kidney and presumably containing adrenal tissue revealed areas of tissue reminiscent of rudimentary adrenal medulla or adrenal cortex (data not shown). However, immunohistochemical staining with antibodies against key enzymes in catecholamine synthesis (PNMT and TH) were negative (data not shown).

The lack of a normal adrenal gland structure in POMC null mice points to a critical role of POMC derived peptide(s) in adrenal development. POMC adrenocorticotropin (ACTH) of pituitary origin is the only known ligand for the MC2-R in the adrenal gland. It is surprising that loss of ligand (ACTH) results in loss of the tissue expressing its receptor (MC2-R). Without being bound by theory, the present inventors believe that it may be more likely that another POMC factor distinct from ACTH plays a role as trophic factor in adrenal gland development. Candidate peptides would be peptides derived from the N-terminal non-γ-MSH region of POMC (N—POMC$_{1-28}$. N-POMC$_{2-59}$), which have been implicated in the physiological control of adrenal growth (Estivariz et al., 1982, Nature 297:419422). This can be tested by reconstituting the POMC null mice with candidate peptides. It may also be possible at that point to determine whether the lack of adrenal medulla is a consequence of the lack of POMC peptides, or of adrenal cortical structure, or of adrenal cortical factors (i.e., corticosterone).

The phenotype of obesity, adrenal insufficiency, and altered pigmentation, makes the POMC null mouse a model for the human POMC null syndrome. In the human POMC deficient patients and in the mouse POMC mutant, homozygotes are born within the normal range of weight and size. Development of obesity starts at 4 to 5 months in the reported cases in humans (Krude et al., 1998, Nat. Genet. 19:155-157), and at 1 month in POMC null mice. This time course of obesity is also similar to that seen in fat/fat mice, which lack carboxypeptidase E, a prohormone processing enzyme (Naggert et al., 1995, Nat. Genet. 10:135-142). A defect in processing of POMC could explain the obesity component of the fat/fat phenotype.

In the human POMC deficient patients, ACTH deficiency results in hypocortisolism and, if untreated, in death. In the POMC null mice, the present inventors were unable to detect corticosterone in serum, even under moderate stress conditions. In contrast to humans, mice that develop with maternal but without endogenous corticosterone are viable. A similar observation has been made in mice lacking corticotropin releasing factor, CRH, which develop normally despite very low levels of corticosterone (Muglia et al., 1995, Nature 373:427432). As in offspring from CRH null females, homozygous offspring from POMC null mutants die within the first hours after birth. This is probably due to defective lung maturation with the lack of corticosterone, as has been demonstrated for the CRH null mutants.

Corticosteroids are known to increase food intake (Tempel et al., 1994, J. Neuroendocrinol. 6:479-501) and to decrease energy expenditure (Strack et al., 1995, Am. J. Physiol. 268: R1209-1206). POMC null mice have no detectable corticosterone, yet they are obese. This is so far the only situation where obesity occurs in the absence of corticosterone. In all other forms of murine obesity, corticosterone is at normal or elevated levels. In fact, the excessive obesity in leptin-deficient mice is largely due to the hypercortisolism in this mouse and adrenalectomy blocks the development of excessive obesity in lep$^{ob}$/lep$^{ob}$ mice (Solomon et al., 1973, Endocrinology 93:510-512 and Tokuyama et al., 1989, Am. J. Physiol. 257: E139-144).

Lack of ligands for the melanocortin receptors in POMC-deficient mice replicate fully or partly the effects seen in mice lacking the receptors MC4-R or MC1-R, respectively. In a preliminary analysis, POMC-deficient mice also replicate the defective water repulsion and thermoregulation seen in mutant mice lacking MC5-R (data not shown). The present results provide a strong indication that POMC peptides are the physiological ligands for at least some MC5-R mediated functions.

Example 2

The following example demonstrates that administration of a POMC peptide analog to a mouse having obesity resulted in significant weight loss.

To test initially for the effect of peripheral melanocortins on weight change, we selected the stable agonist [Ac-Cys$^4$, D-Phe$^7$, Cys$^{10}$] α-MSH (4-13) (described in Cody et al., 1985, J. Med. Chem. 28, 583-588; incorporated herein by reference in its entirety). Briefly, [Ac-Cys$^4$, D-Phe$^7$, Cys$^{10}$]

α-MSH (4-13) amide, having the cysteines connected by a disulfide bridge, was obtained from Peninsula Laboratories, CA. Lyophilized powder was dissolved in water at 1 mg/ml, which was diluted in PBS to 10 μg/mL. During the experiments, mice were maintained on a normal 12 h/12 h light/dark cycle with food and water ad libitum. Mice were fed standard laboratory rodent diet (#5001).

Figures 4A, 4B:
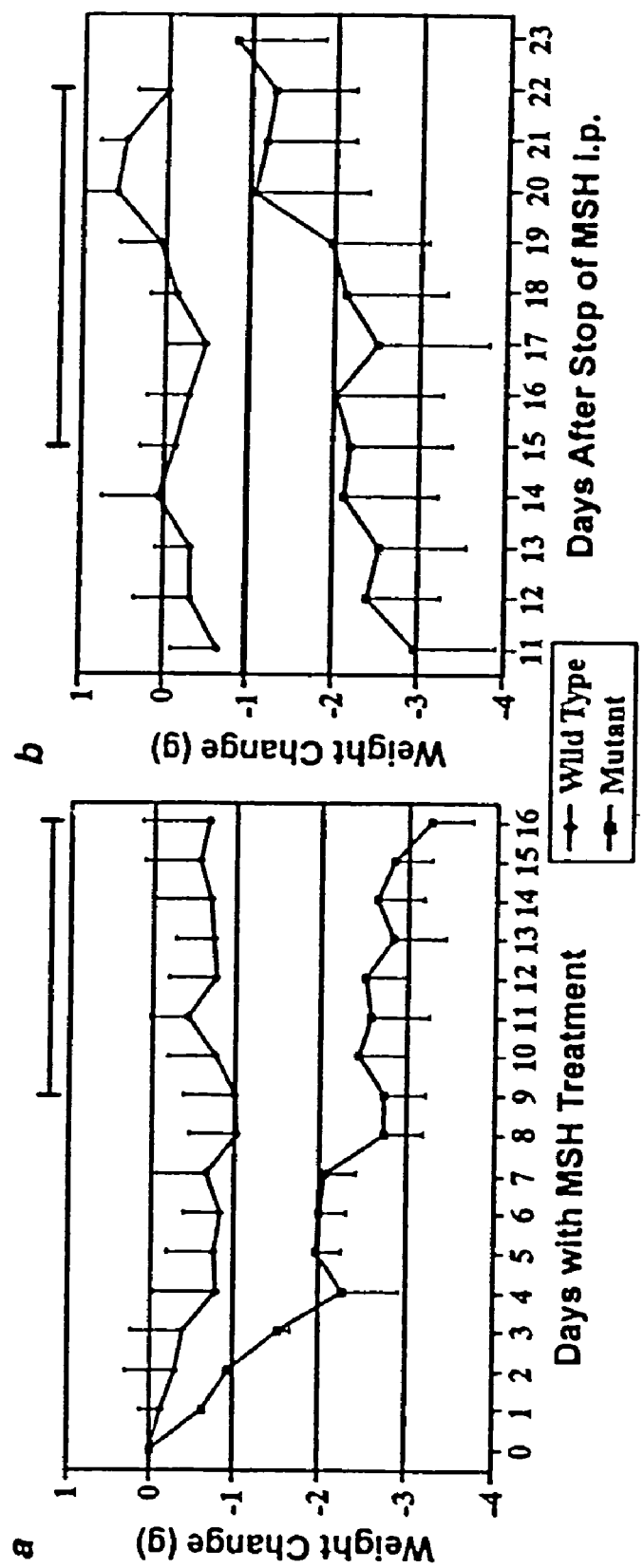
FIG. 4A is a line graph showing the change in body weight from the pretreatment weight for POMC homozygous mutant and wildtype female mice treated with an α-MSH analog once a day.
FIG. 4B is a line graph showing the change in body weight for days 11 to 23 after termination of α-MSH analog treatment.

Daily intraperitoneal injections of one microgram (~1 nmol) of this MSH-agonist (0.1 ml in PBS delivered one to two hours before the onset of darkness) led to a significant weight loss (38% of excess weight within one week, and 46% of excess weight by 2 weeks) in mutant female mice ($p<0.1$ at day 8, $p<0.05$ at day 16), but caused no significant weight loss in wildtype littermates (FIG. 4A) FIG. 4A shows the mean change in body weight from the pretreatment weight in grams for groups of three mice (POMC homozygous mutant and wildtype female mice) for the 16-day period of treatment. When the MSH injections were stopped, mutant mice started to gain weight after about 10 days, and reached close to their pretreatment weight after another two weeks (FIG. 4B).

Figure 4D:
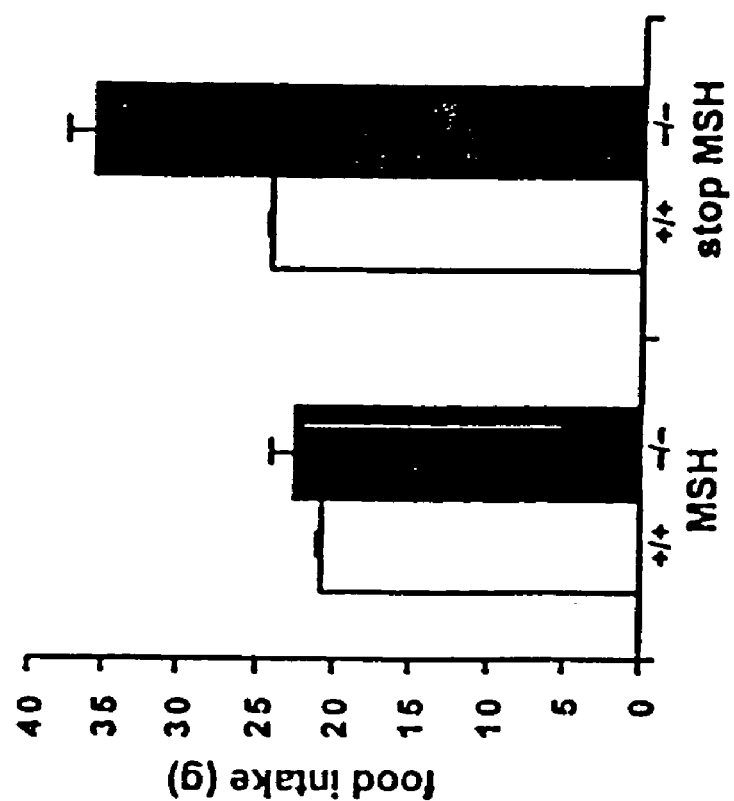
FIG. 4D is a bar graph illustrating the food intake over the second week of MSH analog treatment as compared to over the third week after termination of treatment for POMC homozygous mutant and wildtype female mice treated with an α-MSH analog once a day.
Figure 4C:
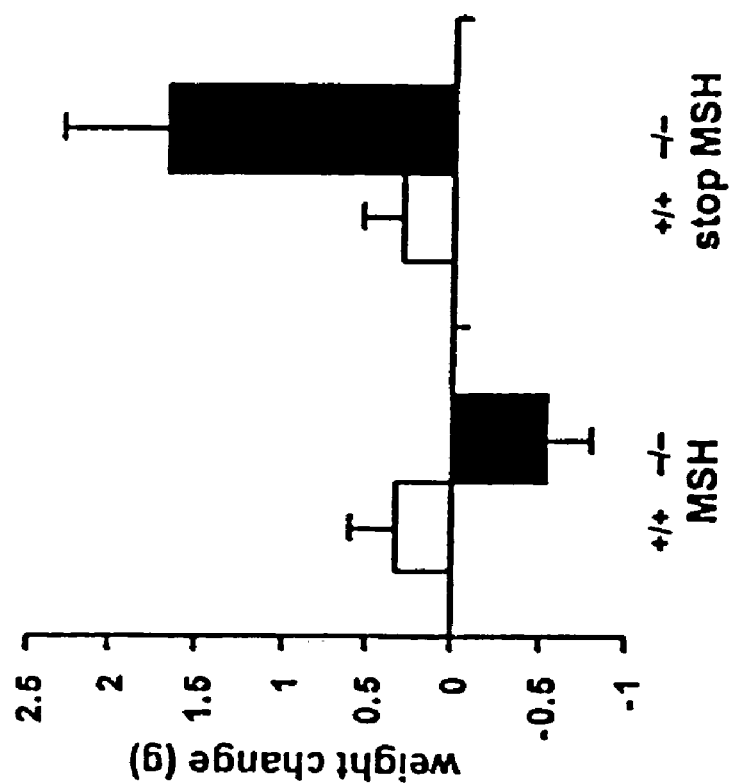
FIG. 4C is a bar graph illustrating the change in body weight over the second week of MSH treatment as compared to over the third week after termination of treatment for POMC homozygous mutant and wildtype female mice treated with an α-MSH analog once a day.

In order to see whether the α-MSH analog has an effect on food intake, we compared weight change and food intake in these mice for one week (see bars in FIGS. 4A and 4B) under MSH analog treatment and after MSH analog treatment was stopped (FIGS. 4C and 4D). During one week under MSH analog treatment mutant mice lost 0.5 g, while wildtype littermates gained 0.3 g; the food intake during this time was equivalent in both groups (20.7 g in wildtypes, and 22.7 g in mutants). After MSH analog treatment had been stopped for two weeks, mutant mice now gained 1.7 g in one week, while wildtype littermates kept their overall weight gain of 0.3 g; food intake now differed significantly between the two groups, with mutants taking up 11.5 g more than wildtypes (35.7 g versus 24.2 g; $p<0.005$). These results show that lack of α-MSH correlates with food intake, although this experiment did not distinguish whether MSH influences body weight primarily through food intake or in combination with a direct effect of melanocortins on adipocytes (inhibition of free fatty acid uptake or stimulation of lipolysis).

An effect of MSH could also be seen on coat pigmentation. The coats of mice treated with MSH for two weeks lost their yellowish tinge (data not shown). Yellow coat pigmentation gradually reappeared after MSH treatment was terminated (data not shown).

Example 3

The following example provides evidence that the major component of weight regulation through the melanocortinergic pathway is not through central, appetite regulating effects.

Figure 5A:
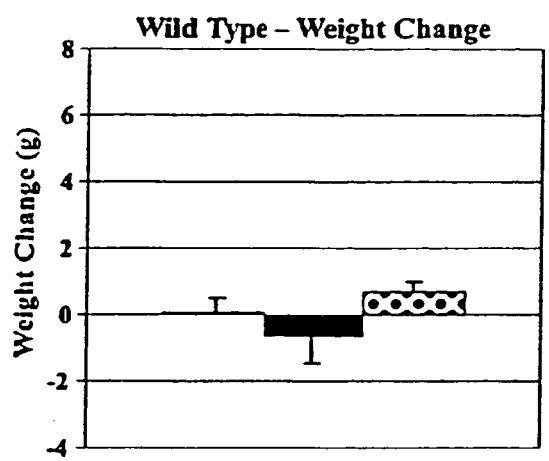
FIG. 5A is a bar graph illustrating body weight change in wildtype mice under conditions of standard diet, standard diet and α-MSH analog treatment, or high fat diet.
Figure 5B:
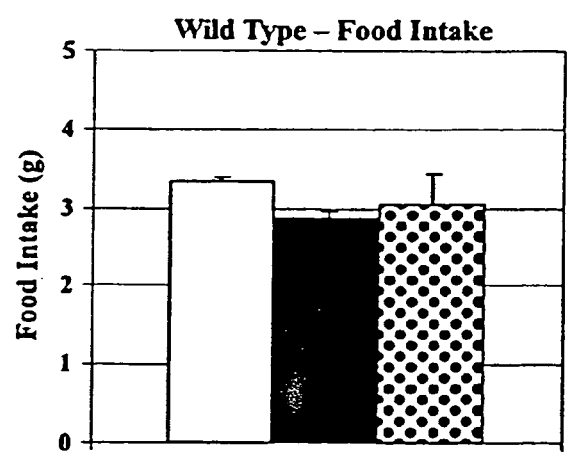
FIG. 5B is a bar graph illustrating food intake in wildtype mice under conditions of standard diet, standard diet and α-MSH analog treatment, or high fat diet.
Figure 5C:
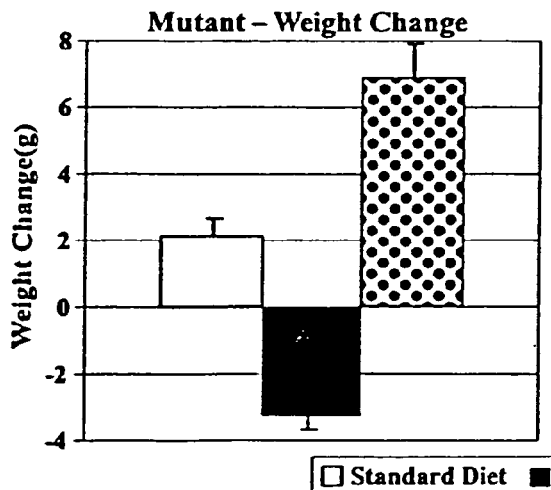
FIG. 5C is a bar graph illustrating body weight change in POMC mutant mice under conditions of standard diet, standard diet and α-MSH analog treatment, or high fat diet.
Figure 5D:
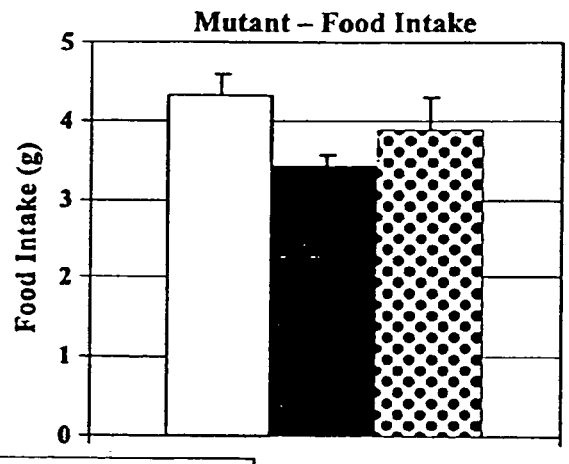
FIG. 5D is a bar graph illustrating food intake in POMC mutant mice under conditions of standard diet, standard diet and α-MSH analog treatment, or high fat diet.

To consider further the question of central, appetite regulating effects of melanocortins versus peripheral (possibly lipolytic or free fatty acid uptake) effects, weight change and food intake in wildtype and POMC null mutant mice (3 female mice per group) under three experimental conditions were measured (FIGS. 5A-5D): (1) standard mouse diet, no treatment; (2) standard mouse diet, MSH analog intraperitoneally (1 or 2 μg, once daily); and (3) high fat diet (#5020), no treatment. With respect to weight regulation, wildtype mice are completely capable of maintaining their body weight constant under those varying conditions (FIG. 5A). Mutant mice lacking POMC peptides gain weight with standard diet, lose excess weight when treated with MSH analog peripherally, and gain more than double the weight with high-fat diet as they gain with standard diet (FIG. 5C). Table 1 shows the statistical significance of the comparisons between genotype, diet, and MSH analog treatment with respect to weight change and food intake. P values were determined by ANOVA. If the major component of weight regulation through the melanocortinergic pathway was the regulation of feeding behavior, the observed changes in body weight in POMC null mutant mice should be paralleled by a similar pattern in food uptake. This, however, was not observed (FIGS. 5B and 5D and Table 1). Rather, the following observations were made: (1) compared to wildtype mice when fed a standard diet, POMC mutant mice are hyperphagic, and they gain weight, yet with MSH analog treatment, they lose weight despite still being hyperphagic; (2) MSH analog treatment decreases food intake in both wildtype and mutant mice, yet only mutant mice lose significant weight; (3) when fed a high fat diet, food intake is unchanged in mutant and wildtype mice compared to feeding on standard diet, as well as compared between mutant and wildtype mice, yet mutant mice gain significant weight, both compared to standard diet and compared to wildtype mice.

TABLE 1

| Comparisons | | weight change | P value | food intake | P value |
|---|---|---|---|---|---|
| wildtype mice | standard diet v. standard diet & MSH analog treatment | — | >0.05 | ↓ | <0.05 |
| | standard diet v. high fat diet | — | >0.05 | — | >0.05 |
| mutant mice | standard diet v. standard diet & MSH analog treatment | ↓ | <0.005 | ↓ | <0.05 |
| | standard diet v. high fat diet | ↑ | <0.05 | — | >0.05 |
| standard diet | wildtype v. mutant | ↑ | <0.05 | ↑ | <0.05 |
| standard diet & MSH analog treatment | wildtype v. mutant | ↓ | <0.05 | ↑ | <0.05 |
| high fat diet | wildtype v. mutant | ↑ | <0.0005 | — | >0.05 |

In experiments assaying transient regulation of feeding behavior, 3 nmol MSH agonist were needed to see a significant effect on food intake when applied intracerebroventricularly; and 100 nmol of agonist were needed when administered intraperitoneally (Kastin et al., ibid.). This is 100 times more than was applied in the present experiments, assaying weight change. Furthermore, the level of MSH agonist that was given peripherally in these experiments is approximately that of the endogenous melanocortin in a normal mouse.

The weight losses and gains of POMC mutant mice in the present experiments cannot be explained solely by their feeding behavior. Rather, these data are consistent with both central and peripheral actions of melanocortins. POMC-deficient mice show both increased food intake and disregulation of metabolism (fat storage/release). Treatment with peripheral melanocortin agonist results in significant weight loss in mutant obese, but not in wildtype, non-obese mice. This may be either a direct effect of melanocortins on adipocytes (inhibition of free fatty acid uptake and/or stimulation of lipolysis) or an indirect effect mediated by another mechanism.

The adult-onset obesity resulting from overexpression of agouti signaling protein in $A^y$ mice (Lu et al., ibid.), or from overexpression of agouti related protein (AGRT or agouti related transcript, ART) in transgenic mice (Graham et al., ibid. and Ollmann et al., ibid.), are generally interpreted as consequences of antagonism of α-MSH on hypothalamic MC4-R. However, without being bound by theory, the present inventors believe that the competition for binding sites with α-MSH may also be in the periphery, given the present results taken together with data which shows that agouti stimulates adipogenesis (Jones et al., 1996, *Am. J. Physiol.* 270:E192-196) and antagonizes melanocortin-mediated lipolysis (Xue et al., 1998, *Faseb J.* 12:1391-1396) directly in adipocytes. Another observation underlying the importance of peripheral mechanisms of weight regulation is that of leptin treatment in the obese mouse, which leads to a loss in body weight not accounted for by a simple decrease of food intake (Levin et al., 1996, *Proc. Natl. Acad. Sci. USA* 93:1726-1730). The lipolytic effects of melanocortins in rabbits have been described (Kastin et al., 1975, *Pharmacol. Biochem. Behav.* 3:121-126 and Richter et al., 1987, *Neuropeptides* 9:59-74). Melanocortins circulate in the periphery and their receptors are found in peripheral tissues; specifically, melanocortin receptors are found on adipocytes (Boston et al., 1996, *Endocrinology* 137:2043-2050).

Example 4

The following example illustrates the effect of α-MSH analog treatment in leptin-deficient obese mice.

Figure 6:
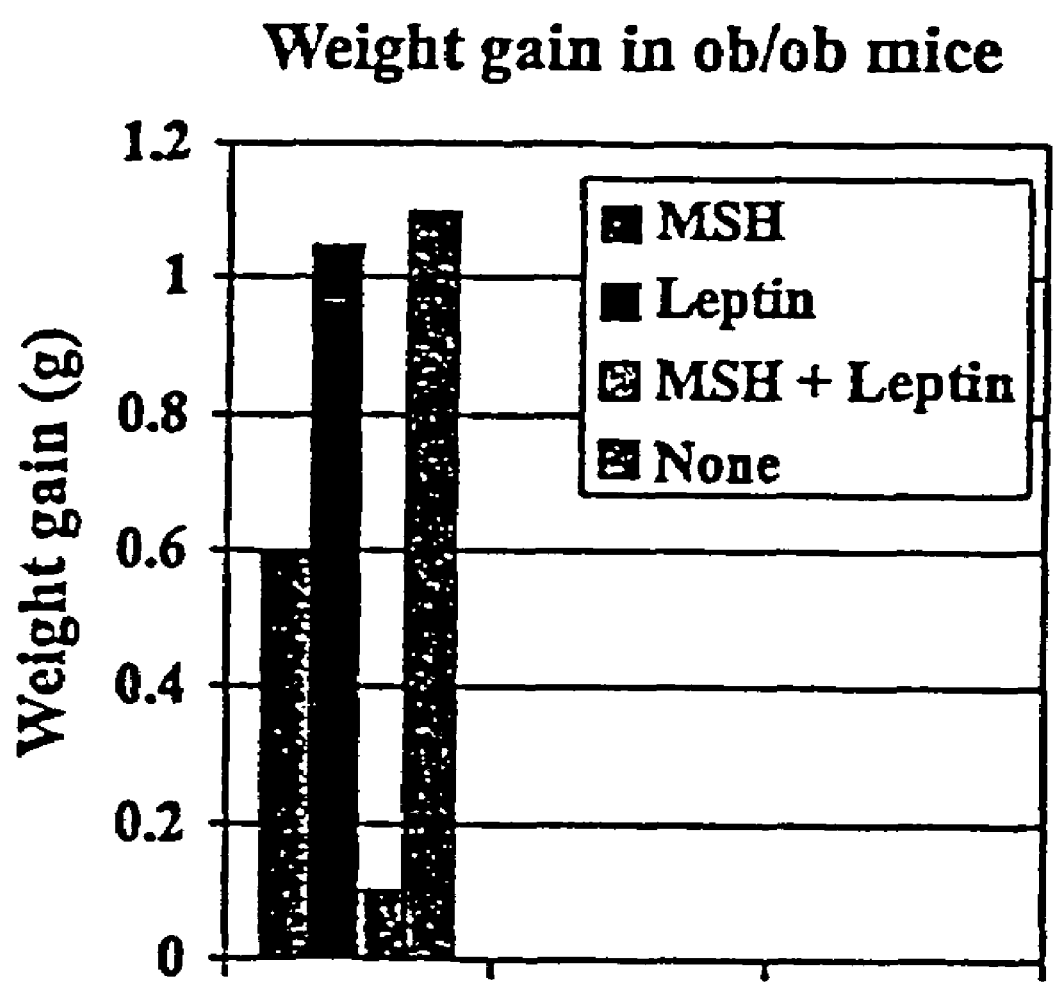
FIG. 6 is a bar graph showing body weight change in obese mice (lep$^{ob/ob}$) treated with leptin, an α-MSH analog, or a combination of the two.

To assess a more general effect of peripheral melanocortin on adipocytes, another genetic form of obesity, in lep$^{ob/ob}$ mice, was treated with the α-MSH analog. In this experiment, the mice received leptin or the α-MSH analog alone, and in combination. Briefly, obese lep$^{ob/ob}$ mice at age 2 months (2 per group) received daily either: (1) 3 μg of α-MSH analog (described in Examples 2 and 3 above); (2) 3 μg of recombinant mouse leptin; (3) 3 μg of α-MSH analog and 3 μg of recombinant mouse leptin in combination; or (4) saline. The compounds were delivered intraperitoneally once daily, 1-2 hours before the onset of darkness. FIG. 6 shows the total weight change over a period of 10 days.

FIG. 6 shows that while the doses of leptin used in this experiment had little effect on preventing further weight gain compared to untreated controls, the α-MSH analog slowed weight gain by almost half. The combination of leptin and MSH had a synergistic effect in that it prevented weight gain almost completely. As in the POMC obesity model described in Example 3, in this obesity model the differences in weight gain do not simply correlate with food intake (data not shown).

Example 5

The following example demonstrates that administration of leptin to obese lep$^{ob/ob}$ mice induces almost normal levels of circulating MSH, that peripherally administered MSH analog decreases weight gain in obese lep$^{ob/ob}$ mice, and that peripherally administered MSH analog increases thermal homeostasis in obese lep$^{ob/ob}$ mice.

Leptin, the product of the ob gene in mouse, is produced by adipocytes. It circulates to the hypothalamus where it binds to cells expressing the leptin receptor, the product of the db gene in mouse. This leptin binding leads, directly or indirectly, to the secretion of melanocyte stimulating hormone (MSH), which in turn binds to neurons expressing the melanocortin 4 receptor (MC4-R). These neurons then suppress appetite. This outline is based on the phenotypes of spontaneous and induced mouse mutants as well as on homologous mutations in humans. Interpretations are in agreement as to leptin being the signal from the fat stores to the central nervous system, and further with respect to an integration of signals with the net result of appetite regulation. However, without being bound by theory, the present inventors believe that there are significant aspects of the phenotypes of these mutants that suggest a greater complexity of body weight homeostasis, specifically the integration of appetite and metabolism. The present inventors believe that there is a factor which comes from the central nervous system to the periphery which mediates this integration. There are several reasons which have led the present inventors to believe that MSH is this factor.

First, the pomc/pomc mutant, which was produced by the present inventors and which is described herein, completely lacks MSH, and shows phenotypes suggestive of altered lipid metabolism. When the fat content of the diet increases, the mice paradoxically eat more and gain weight much more rapidly. This weight gain, which occurs in excess of food intake, argues for a pathologically "increased metabolic efficiency". When these mutants are treated by peripheral administration of an α-MSH analog as demonstrated in the examples above, the mice lose weight, but more than anticipated from the decrease in food intake, again consistent with an increased "metabolic efficiency".

Second, leptin deficient mice (ob/ob) show an "increased metabolic efficiency" which precedes the onset of obesity. These mutants show: (1) weight gain when pair-fed with normal controls; (2) longer survival in a fast than normal mice of equal initial weight; and (3) decreased ability to maintain body temperature at 4° C. Taken together, these data suggest is that the ob/ob mice have adjusted their metabolism to conform to their known fat stores, that is, in the absence of leptin, they sense no fat stores. The mechanism for such an adjustment is unknown at present.

In order to further address the issues related to body weight homeostasis, especially the possibility of the integration of appetite and "metabolic efficiency" through the POMC pathway, the present experiments were designed.

Figure 7:
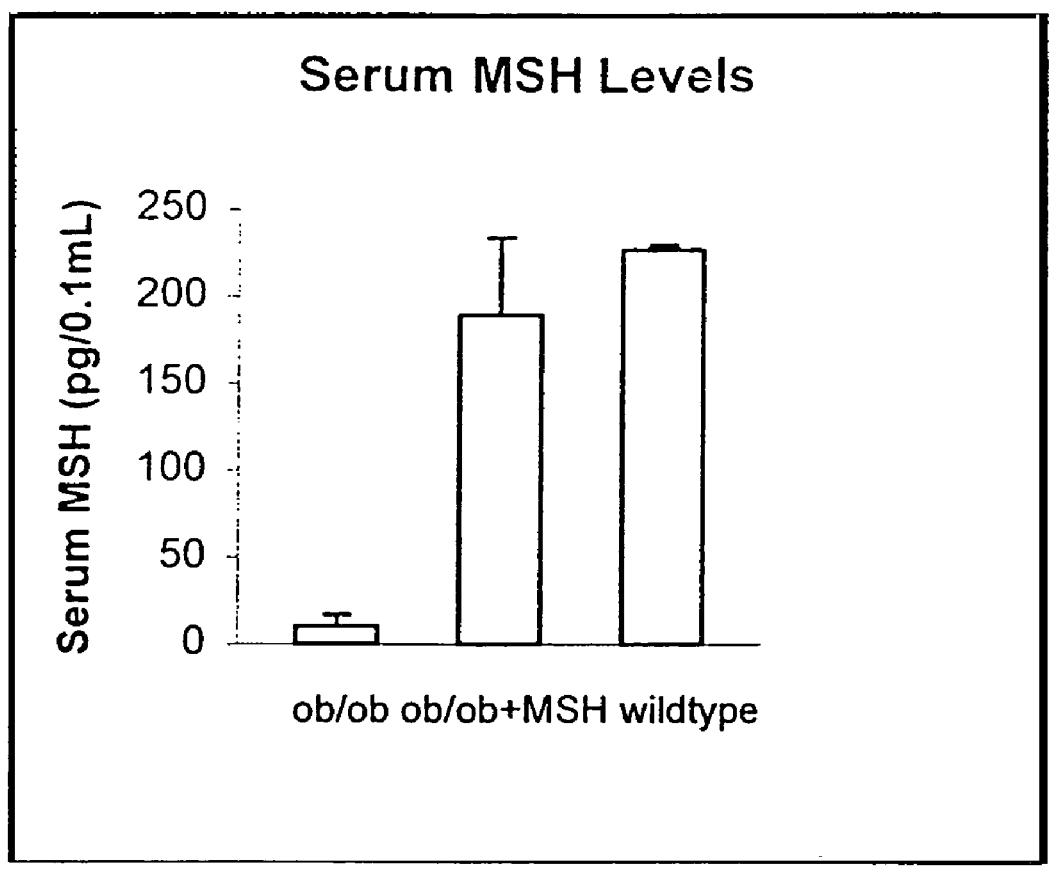
FIG. 7 is a bar graph showing serum MSH levels in obese mice (lep$^{ob/ob}$) before and after treatment with leptin.

An inductive role for leptin in the secretion of MSH is suggested by the low levels of circulating MSH in ob/ob mutants, by the expression of leptin receptors on POMC expressing neurons of the hypothalamus, by the correlation of hypothalamic POMC mRNA with leptin levels in fasting wildtype mice and in ob/ob as well as leptin-reconstituted ob/ob mice, and by the ability of MSH administered intracerebroventricularly to suppress transiently the hyperphagia in ob/ob mutant mice. To test the inductive ability of leptin on circulating MSH levels, ob/ob mutants (ob/ob mutant mice (C57BL/6J-Lep$^{ob}$) and congenic controls were purchased from the Jackson Laboratory, Bar Harbor, Me.) were treated with leptin (7 microgram/day) or with vehicle alone (Murine recombinant leptin was kindly provided by Dr. A. F. Parlow through the National Hormone and Pituitary Program (NHPP); hormones were diluted to 70 micrograms per milliliter in PBS; mice were injected intraperitoneally with 0.1 mL). Two hours after the tenth daily injection, blood samples were drawn from the retro-orbital sinus and analyzed for MSH levels by RIA following the manufacturer's instructions (Peninsula Laboratories, Belmont, Calif.). While circulating MSH in vehicle treated ob/ob mutants were similar to the very low levels reported previously, the MSH levels in leptin treated ob/ob mutants approached those found in normal control mice (FIG. 7).

Figure 8:
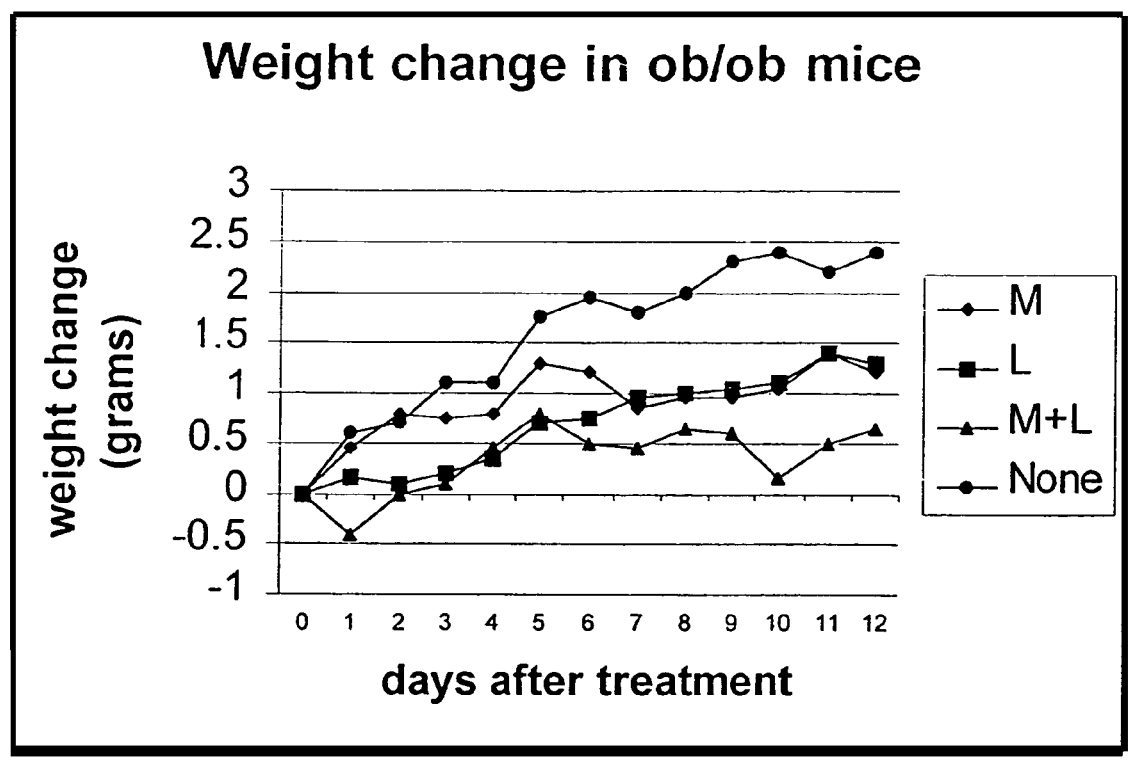
FIG. 8 is a line graph illustrating weight change in obese mice (lep$^{ob/ob}$) after treatment with leptin, an α-MSH analog, a combination of the two.
Figure 9:
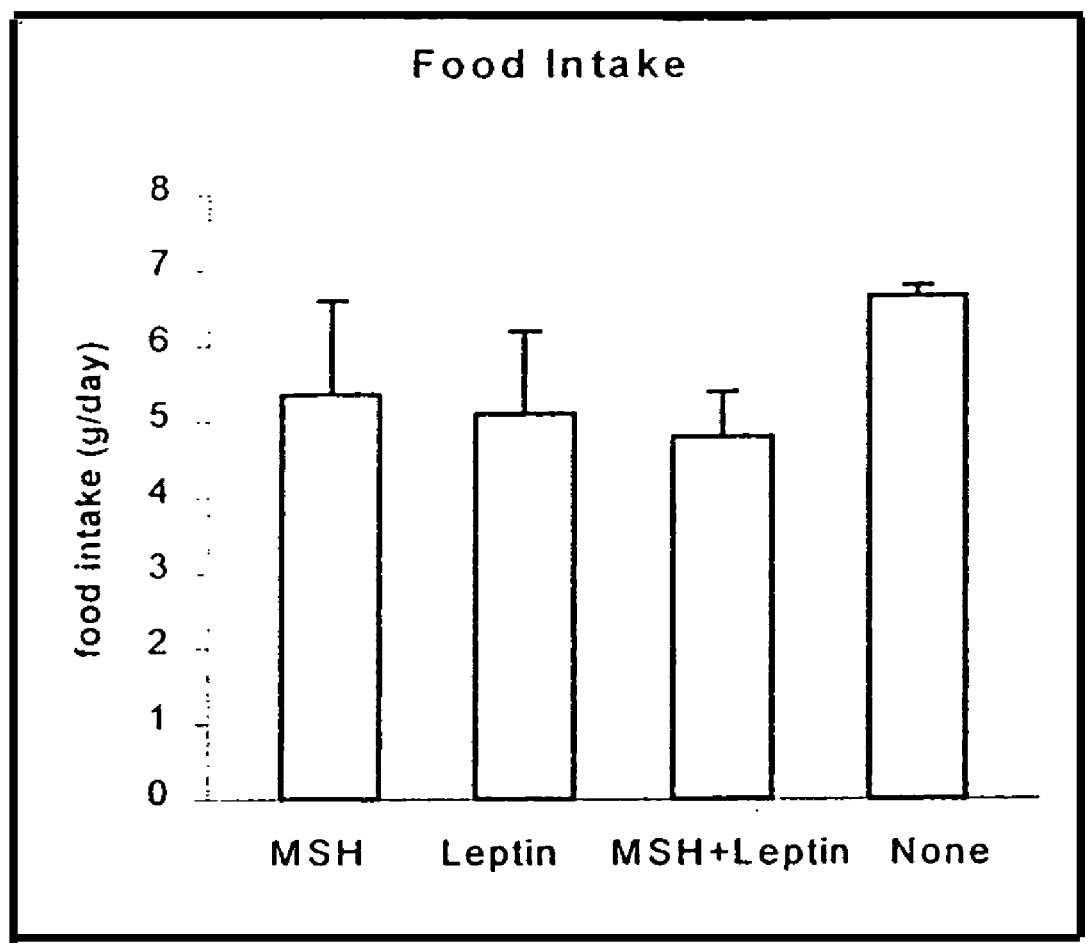
FIG. 9 is a bar graph demonstrating the effect on food intake in obese mice (lep$^{ob/ob}$) after treatment with leptin, an α-MSH analog, a combination of the two.

Leptin deficient (ob/ob) mutants show both hyperphagia and "increased metabolic efficiency" as witnessed by their ability to gain weight even when pair-fed with normal congenic controls. To determine the effects of leptin and MSH on food intake and weight gain, four sets of ob/ob mutants were treated with leptin, an MSH analog, both together, or vehicle alone. The MSH analog [Ac-Cys$^4$, D-Phe$^7$, Cys$^{10}$] α-MSH (4-13) was purchased from Peninsula Laboratories (Belmont, Calif.). Mice were treated with daily injections of 7 micrograms of each, both or neither. The results are shown in FIG. 8. FIG. 8 shows that both leptin treatment and MSH analog treatment effectively decreased weight gain. Surprisingly, the effect of the MSH analog was greater on weight gain than on food intake, indicating a reversal of the "increased metabolic efficiency" of the ob/ob mutant mice (FIGS. 8 and 9).

Figure 10:
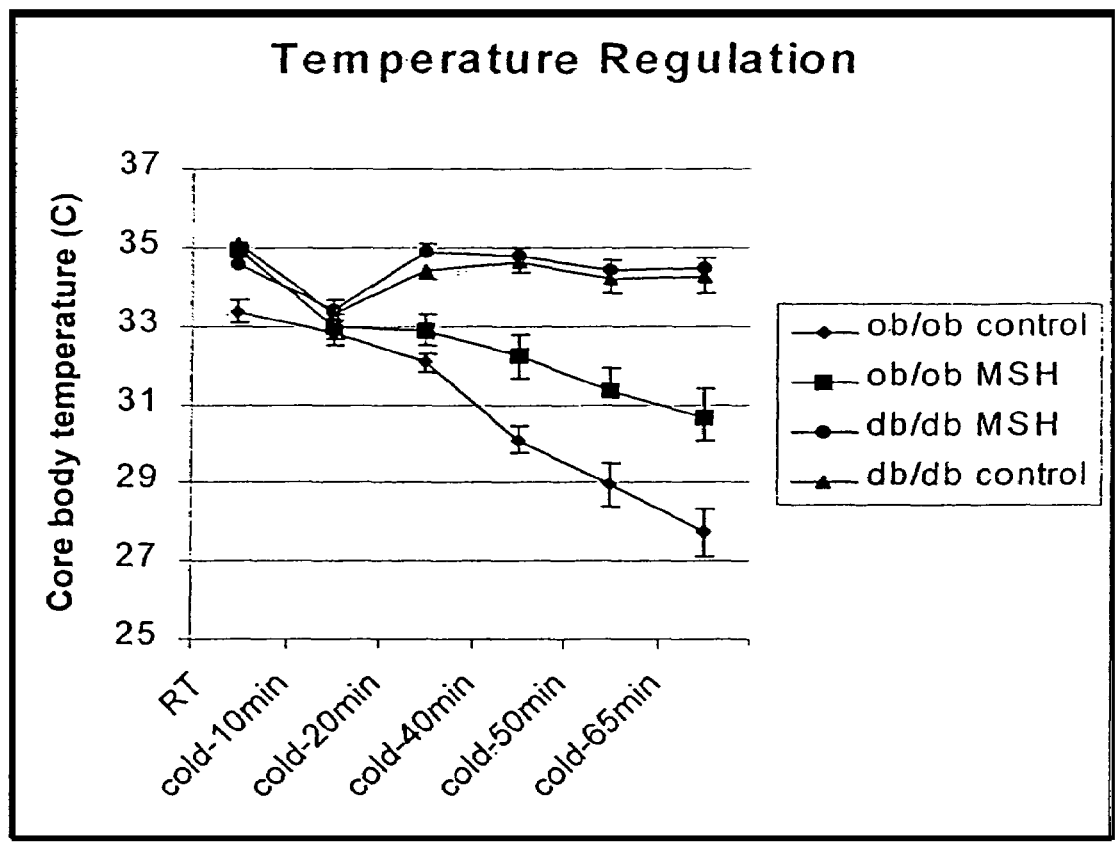
FIG. 10 is a line graph showing the effect of administration of an α-MSH analog on body temperature regulation in obese mice (lep$^{ob/ob}$), and in db/db mice.

In 1977, the decreased ability of ob/ob mutants to maintain body temperature at 4° C. was noted. This preceded the onset of obesity in these mice. In view of the evidence that MSH regulates adipocyte metabolism, the present inventors hypothesized that the low levels of circulating MSH in leptin deficient (ob/ob) mutants was responsible for the impaired thermal regulation. To test this, ob/ob mutants were injected with 7 micrograms of MSH analog or vehicle only as described above. The mice were left without food for 5 hours and then exposed to 4° C. for 65 minutes. Their core temperatures were measured periodically by transfer to a coldroom (4° C.) where core temperatures were measured using a digital thermometer fitted with a rectal probe (Atkins Technical Inc., Gainesville, Fla.). As seen in FIG. 10, the mice treated with the MSH analog maintained their core temperature much better than did the vehicle treated control ob/ob mutants. As the mice had no opportunity to eat between injection of the MSH analog and the cold challenge, food intake cannot be responsible for the altered thermal regulation.

In summary, these experiments have shown: (1) that injection of leptin (7 micrograms) induces almost normal levels of circulating MSH in ob/ob mutants; (2) that peripherally administered MSH analog decreases weight gain in ob/ob mutants; and (3) that peripherally administered MSH analog increases thermal homeostasis in ob/ob mutants.

In view of these results, the present inventors, without being bound by theory, propose the following modifications to the leptin-POMC scheme presented above. First, the present inventors have demonstrated that MSH mediates both a decrease in appetite (via a central mechanism) and a decrease in "metabolic efficiency" (via a peripheral mechanism). These responses are complementary responses to sufficient fat stores. Absent of sufficient fat stores, an organism may be expected both to eat more and to expend less energy. Like the ob/ob mutants, the pomc/pomc mutants show an "increased metabolic efficiency" which can be reversed by peripherally administered MSH analog, as described in the present invention. The direct effect of MSH on appetite suppression is assumed to be mediated through MC4R expressing neurons, while the decrease in "metabolic efficiency" is postulated to be mediated by peripheral cells expressing melanocortin receptors, especially adipocytes.

The decreased ability to thermoregulate of ob/ob mutants reflects their inability to mobilize fat without the signal (MSH) from the center to the periphery to do so; this MSH signal is dependent on a leptin signal indicating sufficient fat stores. Decreased thermoregulation can be alleviated either by exogenous leptin, which in turn increases circulating MSH, or by direct administration of exogenous MSH.

Again without being bound by theory, the present inventors believe that the presence of melanocortin receptors on adipocytes and the ability of MSH at physiological levels to affect metabolism are consistent with a direct effect of MSH in the periphery. Indeed, the differences between leptin treated and MSH analog treated ob/ob mice are consistent with two effects of MSH, one central (appetite suppressing) and one peripheral (metabolic). In addition, the inability of peripheral MSH analog to supplement the weight reducing effect in ob/ob mice of a leptin dose sufficient to induce normal MSH levels is consistent with the ability of leptin, under normal circumstances, to induce levels of central and peripheral MSH balanced for appetite and metabolism. Whenever this is not the case (e.g. ob/ob, and pomc/pomc mutants) peripheral administration of an MSH analog can change the "metabolic efficiency".

While various embodiments of the present invention have been described in detail, it is apparent that modifications and adaptations of those embodiments will occur to those skilled in the art. It is to be expressly understood, however, that such modifications and adaptations are within the scope of the present invention.

We claim:

1. A method to decrease the body weight or reduce weight gain, comprising the step of administering to the peripheral tissue of an animal in need thereof a therapeutic composition comprising a therapeutically effective amount of about 40 micrograms to about 1 mg of an α-MSH analog compound [Ac-Cys$^4$,D-Phe$^7$,Cys$^{10}$] α-MSH (4-13) per kg body weight of the animal wherein the therapeutically effective amount is insufficient to cause a statistically significant change in the appetite of the animal after administration of the compound as compared to before administration of the compound.

2. The method of claim 1, wherein the α-MSH analog compound has the following characteristics: (1) an ability to bind to a melanocortin receptor that is expressed in peripheral tissues, and (2) biological activity selected from the group consisting of: stimulation of lipolysis and inhibition of the uptake of fatty acids by adipocytes.

3. The method of claim 1, wherein the α-MSH analog compound binds to a melanocortin receptor expressed in the peripheral tissues with a higher affinity than to melanocortin-4 receptors (MC-4R).

4. The method of claim 1, wherein the α-MSH analog compound does not bind to MC-4R receptors under physiological conditions.

5. The method of claim 1, wherein the administration of the therapeutic composition minimizes delivery of said compound to the central nervous system of the animal.

6. The method of claim 1, wherein the therapeutic composition is directly delivered to systemic circulation.

7. The method of claim 1, wherein the therapeutic composition is delivered by parenteral administration.

8. The method of claim 1, wherein the therapeutic composition comprises from about 0.1% to about 90% weight of the α-MSH analog compound.

9. The method of claim 1, wherein the therapeutic composition comprises from about 0.1% to about 1% weight of the α-MSH analog compound.

10. The method of claim 1, further comprising the steps of:
measuring the weight of the animal before administering the therapeutic-composition to obtain a first weight measurement,
administering the therapeutic composition at a time of treatment, and
measuring the weight of the animal after administering the therapeutic-composition to obtain a second weight measurement,
wherein the second weight measurement is obtained after a weight treatment effective interval.

11. The method of claim 10, wherein the second weight measurement is less than the first weight measurement.

12. The method of claim 10, wherein the weight treatment effective interval is about 7-10 days.

13. The method of claim 10, wherein the weight treatment effective interval is about one month.

14. The method of claim 10, wherein the animal is a human.

15. The method of claim 1, further comprising the steps of:
measuring the serum leptin level of the animal before administering the therapeutic composition to obtain a first leptin measurement, and
administering the therapeutic composition at a time of treatment.

16. The method of claim 15, wherein the first leptin measurement is less than about 50 ng/mL.

17. The method of claim 15, wherein the first leptin measurement is less than about 10 ng/mL.

18. The method of claim 1, further comprising the step of:
measuring the serum leptin level of the animal after administering the therapeutic composition to obtain a second leptin measurement, wherein the second leptin measurement is obtained after a leptin treatment effective interval.

19. The method of claim 18, wherein the second leptin measurement is at least 1% lower than the first leptin measurement, and the leptin treatment effective interval is about 7-10 days.

* * * * *